United States Patent
Wong et al.

(10) Patent No.: US 8,389,569 B2
(45) Date of Patent: Mar. 5, 2013

(54) POLYSPIRANE COMPOUNDS, APPLICATION THEREOF IN THE TREATMENT OF MALARIA OR TOXOPLASMOSIS AND METHOD FOR PREPARING SAME

(75) Inventors: Yung-Sing Wong, Saint Martin-d'Heres (FR); Marine Aimée Peuchmaur, Apprieu (FR); Eric Marechal, Grenoble (FR); Cyrille Botte, Grenoble (FR); Henri Joseph Vial, Montpellier (FR); Nadia Saidani, Nantes (FR)

(73) Assignee: Universite Joseph Fourier, Grenoble (FR)

( * ) Notice: Subject to any disclaimer, the term of this patent is extended or adjusted under 35 U.S.C. 154(b) by 330 days.

(21) Appl. No.: 12/681,485

(22) PCT Filed: Oct. 2, 2008

(86) PCT No.: PCT/FR2008/001378
§ 371 (c)(1),
(2), (4) Date: Jul. 19, 2010

(87) PCT Pub. No.: WO2009/077677
PCT Pub. Date: Jun. 25, 2009

(65) Prior Publication Data
US 2010/0298422 A1    Nov. 25, 2010

(30) Foreign Application Priority Data

Oct. 3, 2007 (FR) .................................. 07 06929

(51) Int. Cl.
*A61K 31/352* (2006.01)
*A61P 33/02* (2006.01)
*C07D 493/20* (2006.01)
*C07D 493/22* (2006.01)

(52) U.S. Cl. .................. 514/455; 514/453; 549/344
(58) Field of Classification Search .................. 514/455, 514/453; 549/344
See application file for complete search history.

(56) References Cited

PUBLICATIONS

Marine Peuchmaur et al., "Studies towards the synthesis of Acul eat in C", SYNLETT, Oct. 19, 2007, pp. 2902-2906, XP002483975.
Jorg Heilmann et al.:,"Anti protozoal activity and cytotoxicity of novel1,7-dioxadispiro(5.1.5.2)pentadeca-9,12-dien-11-one derivatives from *Amomum aculeatum*", Helvetica Chimica Acta., 2000, pp. 2939-2945, vol. 83, XP002483976.
International Search Report in Corresponding Application PCT/FR2008/001378 dated Oct. 23, 2009.

*Primary Examiner* — Sreeni Padmanabhan
*Assistant Examiner* — Sahar Javanmard
(74) *Attorney, Agent, or Firm* — Young & Thompson

(57) ABSTRACT

Novel polyspirane compounds used in the treatment of diseases involving parasites that belong to the phylum of apicomplexae, and a method for preparing the same.

24 Claims, 11 Drawing Sheets

POLYSPIRANE COMPOUNDS, APPLICATION THEREOF IN THE TREATMENT OF MALARIA OR TOXOPLASMOSIS AND METHOD FOR PREPARING SAME

The present invention relates to novel polyspirane compounds, their use in the treatment of malaria or toxoplasmosis and their preparation method.

The Apicomplexa phylum consists of several thousand species of single-cell parasites responsible for major infectious diseases, including malaria (caused by parasites of the genus *Plasmodium*), toxoplasmosis (*Toxoplasma gondii*), piroplasmosis (*Babesia*), neosporosis (*Neospora*) etc.

Malaria is the most widespread parasitic disease in the world. All the countries in Europe, where it is not endemic, have so-called "imported malaria".

There are more than a hundred species of *Plasmodium*, only four of which parasitize humans: *Plasmodium malariae, Plasmodium vivax, Plasmodium ovale* and *Plasmodium falciparum*, which is by far the most virulent (80% of fatal cases). The infection is carried by a female mosquito of the genus *Anopheles* (*Anopheles gambiae*).

During the 1950s and 1960s, the intensive use of insecticides, such as dichlorodiphenyltrichloroethane (DDT), made it possible to considerably reduce the endemic areas.

This strategy was however abandoned in 1969: in addition to the environmental risks linked to public health, the intensive use of insecticides promoted the appearance of resistant strains of mosquito.

In terms of treatment and prophylaxis (Wiesner J., Ortmann R., Jomaa H., Schlitzer M., New antimalarial drugs. *Angew. Chem. Int. Ed.* 2003, 42, 5274-5293; Biagini G. A., O'Neill P. M., Bray P. G., Ward S. A., Current drug development portfolio for antimalarial therapies. *Curr. Opin. Pharm.* 2005, 5, 473-478), from the $18^{th}$ century onwards, in Latin America, Peruvian bark (*Cinchona*) was used in the treatment of fevers, but it was not until 1820 that the active molecule was isolated: quinine (FIG. 1). In 1891, the first synthetic molecule was used in the treatment of humans for this disease: this was methylene blue. The years of research which followed resulted in the synthesis of numerous compounds, such as pamaquine, mepacrine and chloroquine (1946). However, the first cases of resistance (Hyde J. E., Drug-resistant malaria. *Trends in parasitology* 2005, 21, 494-498) to chloroquine appeared rapidly, due to its excessive use and probably insufficient doses. The Second World War and the Vietnam War gave a new momentum to research into original active molecules resulting in the development in particular of proguanil, then pyrimethamine and mefloquine. Finally, in 1972, artemisinin, a sesquiterpene endoperoxide lactone, was isolated from the aerial parts of annual wormwood *Artemisia annua*, a plant used in China in the treatment of fevers since 340 CE.

The failures of the new medicaments against malaria occurred at an alarming rate, for example, resistance to mefloquine appeared only 5 years after its introduction as a prophylactic treatment in certain parts of Thailand, while resistance to atovaquone was even more rapid, appearing the same year as it was launched (Biagini G. A., O'Neill P. M., Bray P. G., Ward S. A., Current drug development portfolio for antimalarial therapies. *Curr. Opin. Pharm.* 2005, 5, 473-478).

Artemisinin and its derivatives are currently the only compounds which have not given rise to any resistance on the part of the parasite.

The WHO (http://www.who.int/topics/malaria/fr/, $10^{th}$ Apr. 2007) therefore recommends a use of these molecules in combination with other compounds in order to avoid the appearance of new resistance phenomena. However, these molecules have drawbacks, in particular their very low solubility.

As specific or cross-resistance phenomena are developing more and more rapidly in the parasite (Hyde J. E., Drug-resistant malaria. *Trends in parasitology* 2005, 21, 494-498), it is essential to find novel molecules having both original structures and acting on new biological targets.

Just like malaria, toxoplasmosis is a parasitic disease the agent of which is a protozoa with a curved shape, *Toxoplasma gondii*. Present all over the world, toxoplasmosis (Montoya J. G., Liesenfeld O., Toxoplasmosis. *Lancet* 2004, 363, 1965-1976) is the most common parasitic infection in warm-blooded animals, mammals and birds.

Toxoplasmosis is also a disease with three participants: the parasite (*Toxoplasma gondii*, the only species known to date), the human being (the intermediate host) and the feline, generally a domestic or wild cat (the ultimate host). The development cycle of *Toxoplasma gondii* can be indirect, passing through one or more intermediate hosts, but it can also be direct, i.e. without an intermediate host.

Toxoplasmosis is generally asymptomatic; despite the fact that the parasite *Toxoplasma gondii* essentially presents as an opportunistic pathogen which can cause serious diseases in immunodeficient patients, cerebral encephalitis or other psychiatric complications (disorientation, anxiety, depression, psychosis etc.), or in the foetus.

In a standard fashion, when toxoplasmosis affects immunocompetent individuals, no treatment is used unless the symptoms prove to be intense or persistent: existing treatments in fact aim only to suppress the proliferation of the parasite, during the acute phase, until immunity is acquired. There is at present no treatment against chronic toxoplasmosis since no medicament is capable of eliminating the tissue cysts. Finally, there are very few molecules on the market (FIG. 2):

sulphonamides. These are active against *Toxoplasma gondii*, and among them, the most used are sulphadiazine and sulphamerazine. The mode of action of these compounds is identical on most microorganisms: they compete with para-aminobenzoic acid (PABA, ex-vitamin B10) and thus inhibit the synthesis of nucleic acids.

pyrimethamine. Used in the treatment of malaria, this antifolinic agent is also active against *Toxoplasma gondii*.

Sulphadiazine and pyrimethamine act in synergy and therefore constitute the treatment of choice against the human parasite: only the trophozoites are affected by this dual therapy. However, numerous side effects (allergic reactions affecting 5 to 15% of the patients) can result from this chemotherapy. This is the case for example with thrombocytopenia and leukopenia: in order to remedy these problems, a folinic acid (leucoverin) can be administered simultaneously.

Other alternative therapies are also used (pyrimethamine in combination with the sulphones, tetracyclines or macrolides, such as spiramycin), but they remain less effective. Despite this, controversies (Kravetz J. D., Federman D. G., Toxoplasmosis in pregnancy. *Am. J. Med.* 2005, 118, 212-216; The SYROCOT (Systematic Review on Congenital Toxoplasmosis) study group, Effectiveness of prenatal treatment for congenital toxoplasmosis: a meta-analysis of individual patient's data. Lancet 2007, 369, 115-122) persist concerning the efficacy of existing therapies or chemoprophylaxes, in particular for neonatal treatments.

As current treatments have numerous drawbacks and are ineffective against the encysted forms of toxoplasmosis, there is a need to find medicaments which are both less toxic and active against the chronic stages of the parasite.

A priori, no resistance phenomenon (Petersen E., Toxoplasmosis. *Semin. Fetal. Neonatal Med.* 2007, 12, 214-223) has been detected to date, despite drug pressure on humans. It has been possible to induce cases of resistance of *T. gondii* to sulphonamides in the laboratory, however the risks seem low.

The natural aculeatins (FIG. 3) were isolated by Heilman and his team in 2000 (J. Heilmann, S. Mayr, R. Brun, T. Rali, O, Sticher, Antiprotozoal activity and cytotoxicity of novel 1,7-dioxadispiro[5.1.5.2]-pentadeca-9,12-dien-11-one derivatives from *Amomum aculeatum. Helv. Chim. Acta* 2000, 83, 2939-2945; J. Heilmann, R. Brun, S. Mayr, T. Rali, O, Sticher, Minor cytotoxic and antibacterial compounds from the rhizomes of *Amomum aculeatum. Phytochemistry* 2001, 57, 1281-1285): these are molecules having a complex three-dimensional structure which have average anticancer and antiprotozoal (in particular antimalarial) properties.

One of the purposes of the present invention is to provide novel polyspirane compounds for the preparation of a medicament intended for the prevention or treatment of pathologies involving parasites belonging to the Apicomplexa phylum.

Another purpose of the invention is to provide pharmaceutical compositions containing at least one polyspirane compound for the prevention or treatment of pathologies such as malaria or toxoplasmosis.

Another purpose of the invention is to provide a process for the preparation of the polyspirane compounds.

As a result, the present invention relates to the use of at least one polyspirane compound, or of the physiologically acceptable salts thereof, of Formula (I) below:

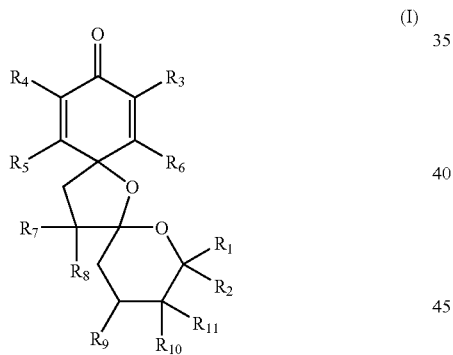

in which:
$R_1$ represents hydrogen and $R_2$ represents a-$CH_2COX$—R' group, in which X=N, O, C;
when X=O, R' represents a linear or branched, saturated or unsaturated alkyl of 1 to 20 carbon atoms or a cycloalkyl of 3 to 8 carbon atoms;
when X=$CH_2$, R' represents hydrogen, a linear or branched, saturated or unsaturated alkyl of 1 to 20 carbon atoms or a cycloalkyl of 3 to 8 carbon atoms;
when X=N, N can be monosubstituted by R' or disubstituted by R' and R'' which represent, independently of each other, hydrogen or a linear or branched, saturated or unsaturated alkyl of 1 to 20 carbon atoms or a cycloalkyl of 3 to 8 carbon atoms;
$R_9$ represents:
an OH group,
an O-allyl group, an O-benzyl group, an O—CO-alkyl group, an O—$COCH_2CO$-alkyl group, said alkyl residue being saturated or unsaturated, linear or branched with 1 to 20 carbon atoms, or an O—CO-cycloalkyl group comprising 3 to 8 carbon atoms,
or,
$R_1$ and $R_2$ together represent a G-1 group:

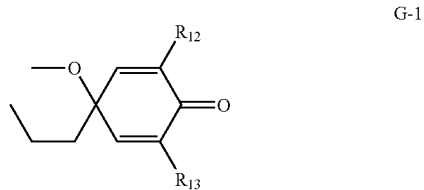

$R_{12}$ and $R_{13}$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, a halogen atom such as chlorine, fluorine, bromine and iodine;
$R_9$ represents:
an OH group,
a linear or branched, saturated or unsaturated alkyl group of 1 to 20 carbon atoms, a cycloalkyl group of 3 to 8 carbon atoms,
an S(O)—R'' group in which R'' is a linear or branched, saturated or unsaturated alkyl of 1 to 20 carbon atoms or a cycloalkyl group of 3 to 8 carbon atoms,
an O-alkyl group, an O—CO-alkyl group, an O—$COCH_2CO$-alkyl group, said alkyl residue being saturated or unsaturated, linear or branched with 1 to 20 carbon atoms, an O-cycloalkyl group of 3 to 8 carbon atoms, an O—$CH_2$—$CH_2$—$N(CH_3)_2$ group; an O—$CH_2$—CCH group,
a

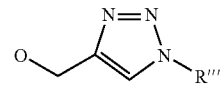

group in which R''' is a linear or branched, saturated or unsaturated alkyl of 1 to 20 carbon atoms,
an N(R'')(R''') group, R'' and R''' being as defined above, whatever $R_1$ and $R_2$ may be:
$R_3$, $R_4$, $R_5$, $R_6$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated O-alkyl group of 1 to 6 carbon atoms, an O-cycloalkyl group of 3 to 8 carbon atoms, a halogen atom such as chlorine, fluorine, bromine and iodine;
$R_7$ and $R_8$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, a linear or branched, saturated or unsaturated NH-alkyl group of 1 to 6 carbon atoms, an NH-cycloalkyl group of 3 to 8 carbon atoms, an NHCO—R group, in which R can be a linear or branched, saturated or unsaturated alkyl group of 1 to 6 carbon atoms, a cycloalkyl group of 3 to 8 carbon atoms,
$R_{10}$ and $R_{11}$ represent independently of each other hydrogen, a hydroxyl group, an O-alkyl group, the alkyl residue being saturated or unsaturated, linear or branched with 1 to 8 carbon atoms, an O-cycloalkyl group of 3 to 8 carbon atoms, a tertiary amine;

for the preparation of a medicament intended for the prevention or treatment of pathologies involving the parasites belonging to the Apicomplexa phylum.

A spirane compound is a compound having two rings connected by the same carbon atom. The term "polyspirane" consequently designates a molecule in which there are several rings which are connected in twos by the same carbon atom.

The compounds of the general formula (I), when $R_1$ represents hydrogen and $R_2$ represents a —CH$_2$COX—R' group, are dispirane compounds in which two carbon atoms ($C_6$ and $C_8$) of the heterocycle with five atoms (B) are connected to two other rings (A) and (C) (formula (II)):

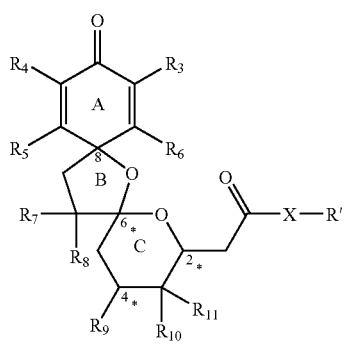

(II)

Said dispirane compounds have at least three asymmetric centres, represented by an asterisk at the level of the carbon atoms $C_2$, $C_4$ and $C_6$ of the ring (C).

The present invention consequently also relates to:
the mixture of all the diastereoisomers,
the mixture of the pairs of syn diastereoisomers [(2S,4R,6R) and (2R,4S,6S)] compounds 10 and [(2S,4R,6S) and (2R,4S,6R)] compounds 11:

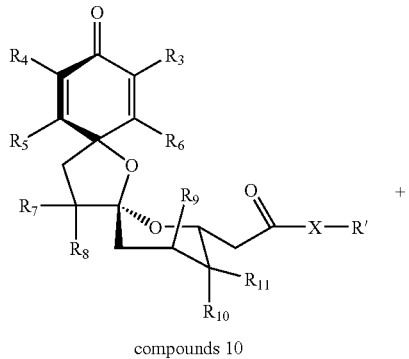

compounds 10

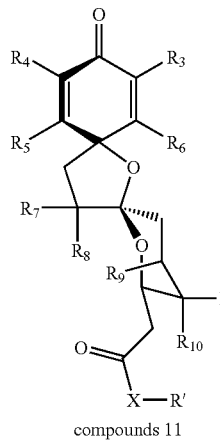

(II-syn)

compounds 11 the mixture of the pairs of anti diastereoisomers [(2S,4S,6R) and (2R,4R,6S)] compounds 12 and [(2S,4S,6S) and (2R,4R,6R)] compounds 13:

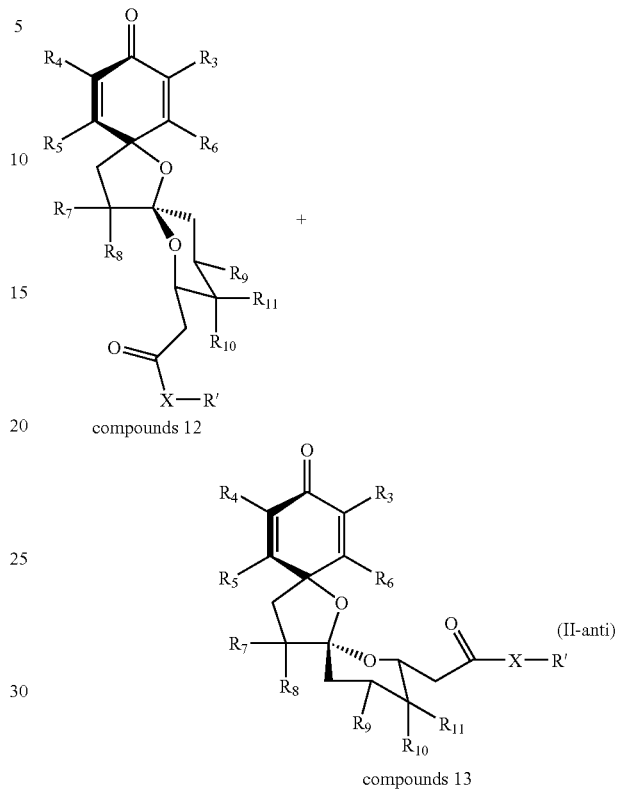

compounds 12

(II-anti)

compounds 13 the racemic syn mixture [(2S,4R,6R) and (2R,4S,6S)] compounds 10,
the racemic syn mixture [(2S,4R,6S) and (2R,4S,6R)] compounds 11,
the racemic anti mixture [(2S,4S,6R) and (2R,4R,6S)] compounds 12,
or the racemic anti mixture [(2S,4S,6S) and (2R,4R,6R)] compounds 13.

The compounds of general formula (I), when $R_1$ and $R_2$ together represent a G-1 group are tetraspirane compounds in which two carbon atoms ($C_8$ and $C_{10}$) of the heterocycle with six atoms (C) are connected to two other rings (B) and (D), themselves each having a carbon atom, C6 (B) and C12 (D), connected to the ring (A) and (E) respectively (Formula (III)):

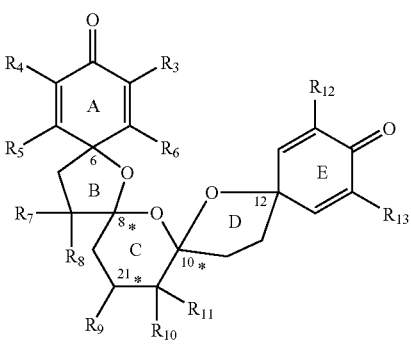

(III)

Similarly, said tetraspirane compounds have at least three asymmetric centres, represented by an asterisk at the level of the carbon atoms $C_8$, $C_{10}$ and $C_{21}$:

As for the dispirane compounds, the present invention consequently also relates to:

the mixture of all the diastereoisomers, the mixture of the pairs of syn diastereoisomers [(8R,10S, 21S) and (8S,10R, 21R)] and [(8S,10S,21S) and (8R, 10R,21R)], or the mixture of the meso compounds (8R,10R,21S) and (8S,10R,21S), the racemic syn mixture [(8R,10S,21S) and (8S,10R, 21R)], the racemic syn mixture [(8S,10S,21S) and (8R,10R, 21R)].

the meso compound (8R,10R,21S), or the meso compound (8S,10S,21R),

The compounds of formulae (III) when $R_7$ and $R_8$, $R_{10}$ and $R_{11}$ represent hydrogen have a plane of symmetry, in the case where the compound is meso (i.e. 8R, 10R,21S), at the level of the ring bearing the residue $R_9$, consequently only the following compounds concerned by the invention exist in this type of structure:

the mixture of a pair of syn diastereoisomers [(8R,10S, 21S) and (8S,10R, 21R)] compounds 16 and the meso compound [(8R,10R,21S)] compounds 16:

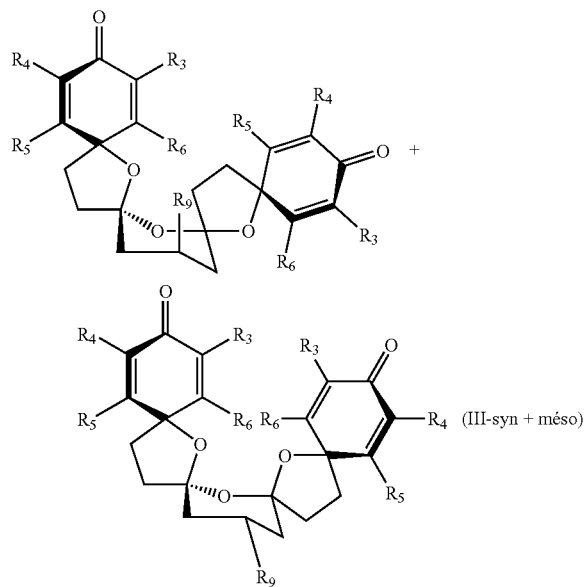

the racemic syn mixture [(8R,10S,21S) and (8S,10R, 21R)], the meso compound [(8R,10R,21S)].

The expression "physiologically acceptable salts" means that the compounds of Formula I, defined above, when they have a radical $R_7$ and/or $R_8$ and/or $R_9$ representing an amine, can exist in the form of quaternary ammonium by reaction of an inorganic acid, an organic acid or an alkyl halide, on the amine.

Examples of inorganic acids making it possible to obtain pharmacologically acceptable salts include, without being limited thereto, hydrochloric acid, hydrobromic acid, nitric acid, carbonic acid, formic acid, monohydrogen carbonic acid, phosphoric acid, monohydrogen phosphoric acid, dihydrogen phosphoric acid, perchloric acid, sulphuric acid, monohydrogen sulphuric acid, hydriodic acid.

Examples of organic acids making it possible to obtain pharmacologically acceptable salts include, but are not limited to, acetic acid, lactic acid, propionic acid, butyric acid, isobutyric acid, palmic acid, maleic acid, glutamic acid, hydroxymaleic acid, malonic acid, benzoic acid, succinic acid, glycolic acid, suberic acid, fumaric acid, mandelic acid, phthalic acid, salicylic acid, benzenesulphonic acid, p-toluenesulphonic acid, citric acid, tartaric acid, methanesulphonic acid, hydroxynaphthoic acid.

The salts of amino acids, such as the arginates and their equivalents are also included as well as the salts of organic acids such as glucuronic acid or galacturonic acid and their equivalents (see, for example, Berge et al., "Pharmaceutical Salts", *Journal of Pharmaceutical Science*, 1977, 66, 1-19).

The alkyl halides making it possible to obtain pharmacologically acceptable salts include, but are not limited to, alkyl bromide, iodide, fluoride or chloride, in which said alkyl residue is saturated or unsaturated, linear or branched, with 1 to 20 carbon atoms, or an O-cycloalkyl group of 3 to 8 carbon atoms.

The term "apicomplexes" denotes parasites having a characteristic combination of organelles called an apical complex.

According to another embodiment, the present invention relates to the use of at least one polyspirane compound, of general formula (II) below:

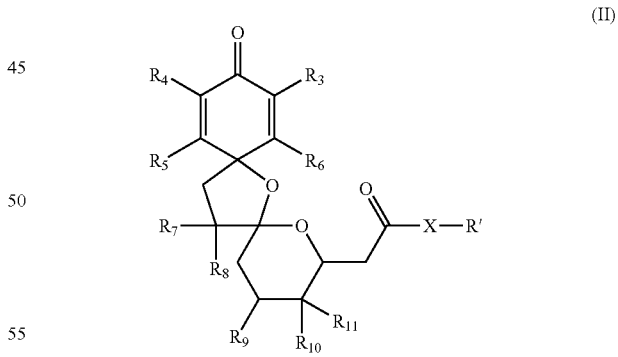

in which $R_3$ to $R_8$, $R_{10}$ to $R_{11}$, X and R' are as defined above, and $R_9$ represents an OH group, an O-allyl group, an O-benzyl group, an O—CO-alkyl group, an O—COCH$_2$—CO-alkyl group, said alkyl residue being saturated or unsaturated, linear or branched with 1 to 20 carbon atoms, or an O—CO-cycloalkyl group comprising 3 to 8 carbon atoms.

In a preferred embodiment, the present invention relates to the use of at least one polyspirane compound, of general formula (III) below:

(III)

in which $R_3$ to $R_8$ and $R_{10}$ to $R_{13}$ are as defined above,
$R_9$ represents:
an OH group,
a linear or branched, saturated or unsaturated alkyl group of 1 to 20 carbon atoms, a cycloalkyl group of 3 to 8 carbon atoms,
an S(O)—R'' group in which R'' is a linear or branched, saturated or unsaturated alkyl of 1 to 20 carbon atoms or a cycloalkyl group of 3 to 8 carbon atoms,
an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group; an O—CH$_2$—CCH group,
an group in which R''' is a linear or branched, saturated or unsaturated alkyl of 1 to 20 carbon atoms,
an N(R'')(R''') group, R'' and R''' being as defined above,
According to a preferred embodiment, said parasites defined above are species of *Plasmodium*, in particular *Plasmodium malariae*, *Plasmodium vivax*, *Plasmodium ovale* and *Plasmodium falciparum*, particularly *Plasmodium falciparum*.

*Plasmodium* is a genus of parasitic protozoa, comprising several species.

*P. falciparum* is the most dangerous of these malaria-causing parasites as it results in the highest mortality rate. Moreover, it represents 80% of all human malarial infections and 90% of deaths.

According to another preferred embodiment, said parasites are of the genus *Toxoplasma* and in particular of the species *Toxoplasma gondii*.

The *Toxoplasma* is a genus of parasitic protozoa of which *Toxoplasma gondii* is one of the species. The ultimate host of the parasite of the species *Toxoplasma gondii* is the cat, although the parasite can be carried by a wide variety of warm-blooded animals including humans.

According to yet another preferred embodiment, said disorders are malaria or toxoplasmosis.

The different species of *Plasmodium* cause malaria in humans. The parasite is transmitted to the human by an *Anopheles* bite (mosquito of warm, swampy regions) and infects the erythrocytes and the cells of the liver during the parasite's life cycle.

The species *Toxoplasma gondii* causes toxoplasmosis in humans, a disease which is normally benign but which can cause severe and even fatal diseases in a foetus whose mother has contracted the disease for the first time during pregnancy.

According to another aspect, the invention relates to a polyspirane compound of formula (I) below:

(I)

in which:
$R_1$ represents hydrogen and $R_2$ represents a —CH$_2$COX—R' group, in which X=N, O, C;
when X=O, R' represents a linear or branched, saturated or unsaturated alkyl of 1 to 20 carbon atoms or a cycloalkyl of 3 to 8 carbon atoms;
when X=CH$_2$, R' represents hydrogen, a linear or branched, saturated or unsaturated alkyl of 1 to 20 carbon atoms or a cycloalkyl of 3 to 8 carbon atoms;
when X=N, N can be monosubstituted by R' or disubstituted by R' and R'' which represent, independently of each other, hydrogen or a linear or branched, saturated or unsaturated alkyl of 1 to 20 carbon atoms or a cycloalkyl of 3 to 8 carbon atoms;
$R_9$ represents:
an OH group,
an O-allyl group, an O-benzyl group, an O—CO-alkyl group, an O—COCH$_2$CO— alkyl group, said alkyl residue being saturated or unsaturated, linear or branched with 1 to 20 carbon atoms, or an OCO-cycloalkyl group of 3 to 8 carbon atoms,
or,
$R_1$ and $R_2$ together represent a G-1 group:

G-1

$R_{12}$ and $R_{13}$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, a halogen atom such as chlorine, fluorine, bromine and iodine;

$R_9$ represents:
- an OH group,
- a linear or branched, saturated or unsaturated alkyl group of 1 to 20 carbon atoms, a cycloalkyl group of 3 to 8 carbon atoms,
- an S(O)—R" group in which R" is a linear or branched, saturated or unsaturated alkyl of 1 to 20 carbon atoms or a cycloalkyl group of 3 to 8 carbon atoms,
- an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, a O—CH$_2$—CH$_2$—N(CH$_3$)$_2$ group; an O—CH$_2$—CCH group,
- a

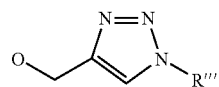

group in which R'" is a linear or branched, saturated or unsaturated alkyl of 1 to 20 carbon atoms,
- an N(R")(R'") group, R" and R'" being as defined above, whatever $R_1$ and $R_2$ may be:

$R_3$, $R_4$, $R_5$, $R_6$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, a halogen atom such as chlorine, fluorine, bromine and iodine;

$R_7$ and $R_8$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, a linear or branched, saturated or unsaturated NH-alkyl group of 1 to 6 carbon atoms, an NH-cycloalkyl group of 3 to 8 carbon atoms, an NHCO—R group, in which R can be a linear or branched, saturated or unsaturated alkyl group of 1 to 6 carbon atoms, a cycloalkyl group of 3 to 8 carbon atoms, $R_{10}$ and $R_{11}$ represent independently of each other hydrogen, a hydroxyl group, an O-alkyl group, the alkyl residue being saturated or unsaturated, linear or branched with 1 to 8 carbon atoms, an O-cycloalkyl group of 3 to 8 carbon atoms, a tertiary amine.

In a preferred embodiment, the polyspirane compound defined above is of general formula (II) below:

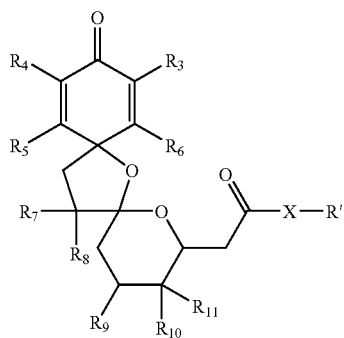

(II)

in which $R_3$ to $R_8$, $R_{10}$ to $R_{11}$, X and $R_9$ are as defined above and $R_9$ represents an OH group, an O-allyl group, an O-benzyl group, an O—CO-alkyl group, said alkyl being saturated or unsaturated, linear or branched with 1 to 20 carbon atoms, or an O—CO-cycloalkyl group comprising 3 to 8 carbon atoms.

According to another embodiment, the polyspirane compound defined above is of general formula (III) below:

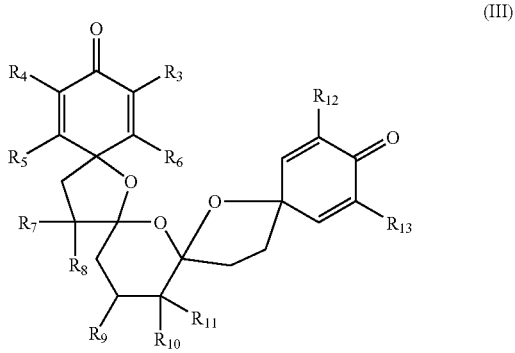

(III)

in which $R_3$ to $R_8$ and $R_{10}$ to $R_{13}$ are as defined above when $R_1$ and $R_2$ form together a G-1 group, and $R_9$ represents:
- an OH group,
- a linear or branched, saturated or unsaturated alkyl group of 1 to 20 carbon atoms, a cycloalkyl group of 3 to 8 carbon atoms,
- an S(O)—R" group in which R" is a linear or branched, saturated or unsaturated alkyl of 1 to 20 carbon atoms or a cycloalkyl group of 3 to 8 carbon atoms,
- an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group; an O—CH$_2$—CCH group,
- a

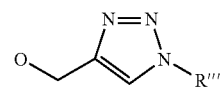

group in which R'" is a linear or branched, saturated or unsaturated alkyl of 1 to 20 carbon atoms,
- an N(R")(R'") group, R" and R'" being as defined above, According to a preferred embodiment, the substituents $R_3$ to $R_8$ and $R_{10}$ to $R_{11}$ of the polyspirane compound of general formula (II), defined above, represent hydrogen, the substituent $R_9$ represents OH, X=O and the substituent R' is a linear, saturated alkyl with 3 carbon atoms, 10 carbon atoms or 18 carbon atoms.

The compound with 3 carbon atoms can correspond to the mixture of the diastereoisomers (2S,4R,6R) and (2R,4S,6S) 10a and (2S,4R,6S)- and (2R,4S,6R) 11a or to the racemic mixture 10a or 11a, or to one of the enantiomers (2S,4R,6R) or (2R,4S,6S) or (2S,4R,6S) or also (2R,4S,6R).

The compounds 10a and 11a are of the following formula:

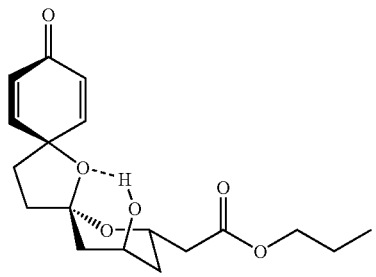
10a

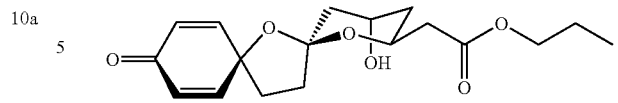
11a

The compound with 10 carbon atoms corresponds to the mixture of the diastereoisomers (2S,4R,6R) and (2R,4S,6S) 10b and (2S,4R,6S)- and (2R,4S,6R) 11b or to the racemic mixture 10b or 11b, or to one of the enantiomers (2S,4R,6R) or (2R,4S,6S) or (2S,4R,6S) or also (2R,4S,6R).

The compounds 10b and 11b are of the following formula:

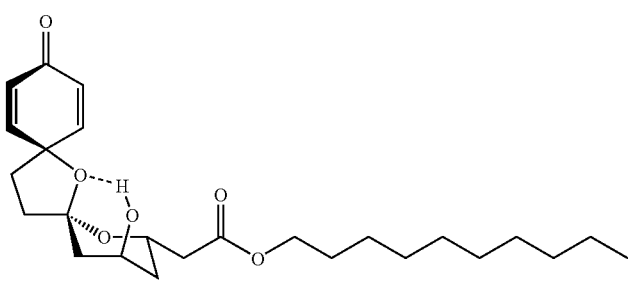
10b

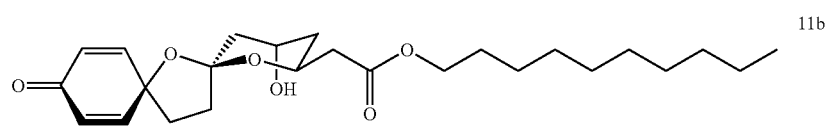
11b

The compound with 18 carbon atoms corresponds to the mixture of the diastereoisomers (2S,4R,6R) and (2R,4S,6S) 10c and (2S,4R,6S)- and (2R,4S,6R) 11c or to the racemic mixture 10c or 11c, or to one of the enantiomers (2S,4R,6R) or (2R,4S,6S) or (2S,4R,6S) or also (2R,4S,6R).

The compounds 10c and 11c are of the following formula:

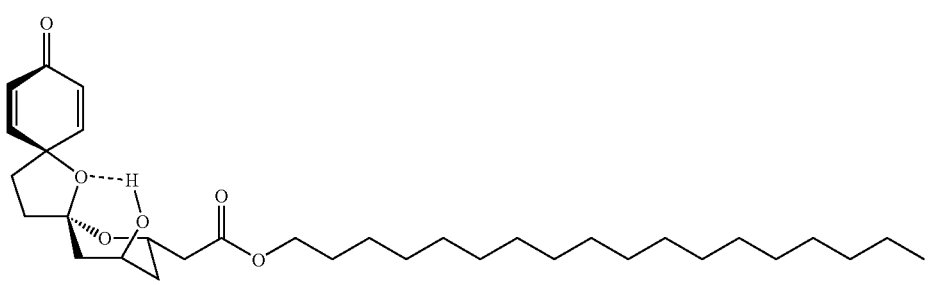
10c

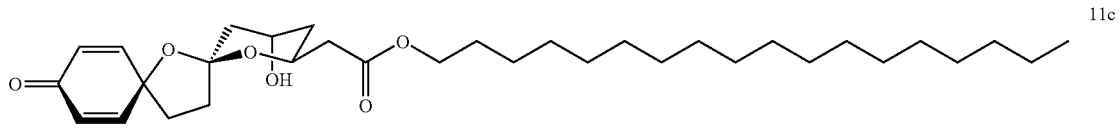
11c

According to a preferred embodiment, the substituents $R_3$ to $R_8$ and $R_{10}$ to $R_{13}$ of the polyspirane compound of general formula (III), defined above, represent hydrogen and the substituent $R_9$ is an OH, O—CO-alkyl group, in which the alkyl is linear and has 7 carbon atoms, 14 carbon atoms or 16 carbon atoms or an alkyl group in which the alkyl is a 2-oxo linear alkyl and has 15 carbon atoms.

The compound in which $R_9$ is an OH group corresponds to the mixture of the diastereoisomers 4a and 4b:

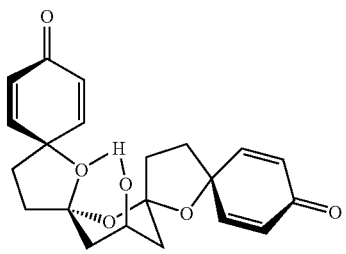

4a

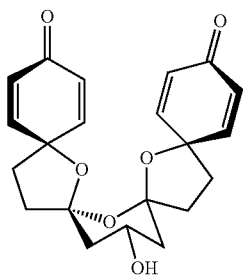

4b

The compound in which $R_9$ is an O—CO-alkyl group, with 7 carbon atoms, corresponds to the mixture of the diastereoisomers 16a and 16b:

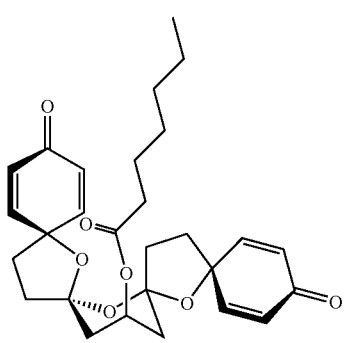

16a

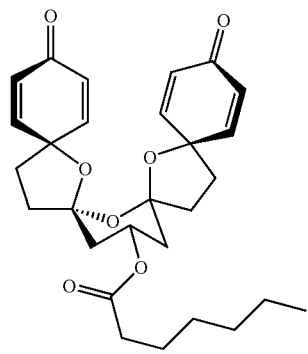

16b

The compound in which $R_9$ is an O—CO-alkyl group, with 14 carbon atoms, corresponds to the mixture of the diastereoisomers 16c and 16d:

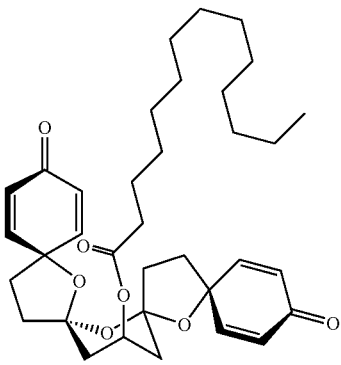

16c

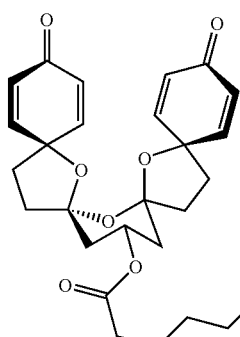

16d

The compound in which $R_9$ is an O—CO-alkyl group, with 16 carbon atoms, corresponds to the racemic mixture 16e:

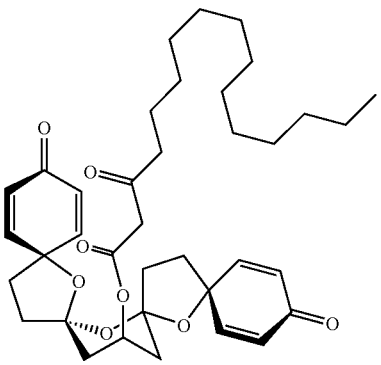

16e

The compound in which R$_9$ is an alkyl group, with 15 carbon atoms, corresponds to the mixture of the diastereoisomers 23c and 23d:

23c

23d

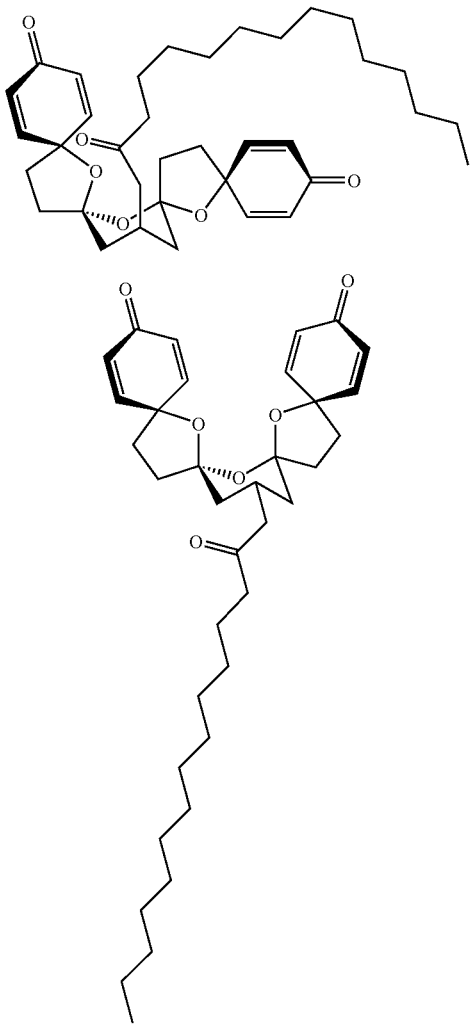

According to another preferred embodiment, the polyspirane compound of general formula (III), defined above, is constituted by a mixture of enantiomers (8R,10S,21S) and (8S,10R,21R).

The mixture of enantiomers (8R,10S,21S) and (8S,10R, 21R) correspond to the compounds 4a, or 16a, or 16c, or 16e or 23c represented above.

In another more preferred embodiment, the polyspirane compound of general formula (III), defined above, is constituted by the meso compound (8R,10R,21S), in a mixture with one of the enantiomers (8R,10S,21S) or (8S,10R,21R).

In another even more preferred embodiment, the polyspirane compound of general formula (III), defined above, is constituted by the meso compound (8R,10R,21S), or by the enantiomer (8R,10S,21S) or also by the enantiomer (8S,10R, 21R).

The meso compound (8R,10R,21S) corresponds to the compounds 4b, or 16b, or 16d or 23d represented above.

According to another aspect, the invention relates to a pharmaceutical composition comprising as active ingredient at least one polyspirane compound of general formula (I), in combination with a pharmaceutically acceptable excipient.

In a preferred embodiment, said pharmaceutical composition is presented in a form which can be administered by oral route at a rate of 0.1 mg/kg/d to 100 mg/kg/d of active ingredient, preferentially from 0.5 mg/kg/d to 10 mg/kg/d and more preferentially from 1 mg/kg/d to 5 mg/kg/d.

According to yet another aspect, the invention relates to a method for preparing the compounds of formula (I):

comprising a stage of phenolic oxidation with an oxidizing agent such as PIFA or PIDA, and in particular PIFA, of a compound of formula (I-Z) below:

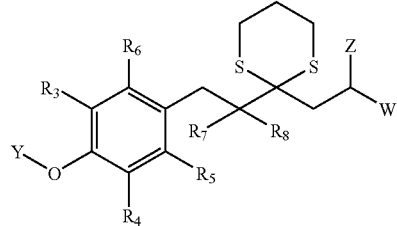

(I-Z)

in which:
either W represents a group of formula (II-W) below:

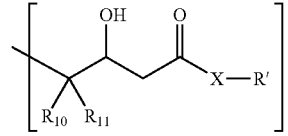

(II-W)

and X=O or N,
Y represents hydrogen,
and Z represents:
  an OH group,
R$_3$ to R$_8$, R$_{10}$, R$_{11}$, X, R' and R''' being as defined above,
in order to obtain a compound of general formula (II) in which X=O or N and R$_9$ represents an OH group,
  and then optionally comprising a stage of acylation or of alkylation in order to obtain a compound of general formula (II) in which R$_9$ is an O—CO-alkyl group, an O-allyl group, an O-benzyl group, an O—COCH$_2$CO-alkyl group, said alkyl residue being saturated or unsaturated, linear or branched with 1 to 20 carbon atoms, or an O—CO-cycloalkyl group comprising 3 to 8 carbon atoms,
or W represents a group of formula (II'-W) below:

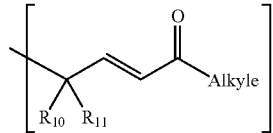

(II'-W)

said alkyl being saturated or unsaturated, linear or branched with 1 to 17 carbon atoms or a cycloalkyl of 3 to 8 carbon atoms, and X=C;
Y represents a (Pr$_3$)Si— group,
and Z represents a (Pr$_3$)Si—O— group,
in order to obtain a compound of general formula (II) in which X=C and R$_9$ represents an OH group, and then optionally comprising a stage of acylation or of alkylation in order to obtain a compound of general formula (II) in which $R_9$ is an O—CO-alkyl group, an O-allyl group, an O-benzyl group, an O—COCH$_2$CO-alkyl group, said alkyl residue being saturated or unsaturated, linear or branched with 1 to 20 carbon atoms, or an O—CO-cycloalkyl group comprising 3 to 8 carbon atoms, or W represents a III-W group:

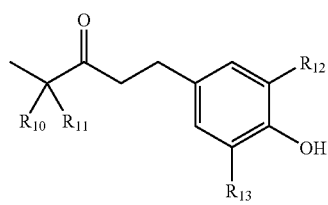

(III-W)

and Z represents:

an OH group, a linear or branched, saturated or unsaturated alkyl group of 1 to 20 carbon atoms, a cycloalkyl group of 3 to 8 carbon atoms, an S—R" group in which R" is a linear or branched, saturated or unsaturated alkyl of 1 to 20 carbon atoms or a cycloalkyl group of 3 to 8 carbon atoms, an O-alkyl group, the alkyl being saturated or unsaturated, linear or branched with 1 to 20 carbon atoms, an O-cycloalkyl group of 3 to 8 carbon atoms, an O—CH$_2$—CH$_2$—N(CH$_3$)$_2$ group; an O—CH$_2$—CCH group, an N(R")(R'") group, R" and R'" being as defined above, $R_3$ to $R_8$ and $R_{10}$ to $R_{13}$ being as defined above, in order to obtain a compound of general formula (III) in which $R_9$ represents:

an OH group, a linear or branched, saturated or unsaturated alkyl group of 1 to 20 carbon atoms, a cycloalkyl group of 3 to 8 carbon atoms, an S(O)—R" group in which R" is a linear or branched, saturated or unsaturated alkyl of 1 to 20 carbon atoms or a cycloalkyl group of 3 to 8 carbon atoms, an O-alkyl group, the alkyl being saturated or unsaturated, linear or branched with 1 to 20 carbon atoms, an O-cycloalkyl group of 3 to 8 carbon atoms, an O—CH$_2$—CH$_2$—N(CH$_3$)$_2$ group; an O—CH$_2$—CCH group, an N(R")(R'") group, R" and R'" being as defined above, and, when Z is an OH group (compound (III-1)), optionally comprising a stage of acylation or of alkylation in order to obtain a compound of general formula (III) in which $R_9$ is an O-alkyl group, an O-cycloalkyl group, an O—CO-alkyl group, an O—COCH$_2$CO-alkyl group, an O—CH$_2$—CH$_2$—N(CH$_3$)$_2$ group; an O—CH$_2$—CCH group, and/or, when Z represents an —O—CH$_2$—CCH group, optionally comprising an addition reaction with $N_3$—R'" in order to obtain a compound of general formula (III) in which $R_9$ is a group

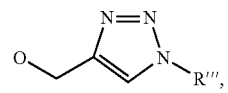

R'" being as defined above.

PIFA (phenyliodonium bis(trifluoroacetate) and PIDA (phenyliodonium diacetate) are both commercial reagents.

The reaction is carried out at ambient temperature in a mixture of solvent such as acetone and water.

FIG. 4 summarizes the different possibilities for obtaining the compounds (II), in which X═O, N or X═C, or compounds (III).

The intermediate (I-Z) thus makes it possible to obtain all the compounds of the invention, as a function of Z and of W.

When the residue $R_9$ of the compounds of formula (II) is an OH group, it is possible to alkylate or acylate said compounds under slightly basic conditions, such as dimethylaminopyridine (DMAP) by reaction with an anhydride, an acid chloride in the case of acylation or an allyl or benzyl halide in the case of alkylation, in a solvent, in particular dichloromethane, in order to obtain compounds of formula (II) in which $R_9$ is an O-allyl group, an O-benzyl group, an O—CO-alkyl group, an O—COCH$_2$CO-alkyl group, or an O—CO-cycloalkyl group.

As a result, these said compounds are obtained in two stages, by phenolic oxidation of the compounds of formula I-Z in which Z═OH, then alkylation or acylation of the compounds of formula (II) obtained in which $R_9$ is an OH group.

According to a preferred embodiment, the method of preparation, defined above, of the compounds of formula (II) in which X═O, N comprises the following stages:

Reaction of an aldehyde of formula (IV) below:

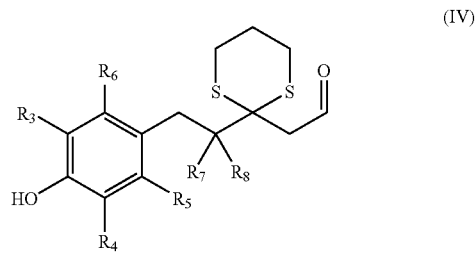

(IV)

$R_3$ to $R_8$ being as defined above, with a compound of formula (VII) below:

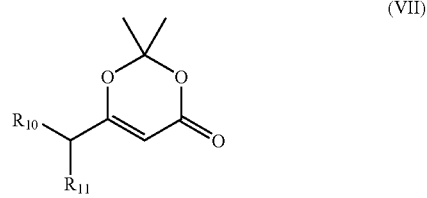

(VII)

in order to obtain the compound of formula (V) below:

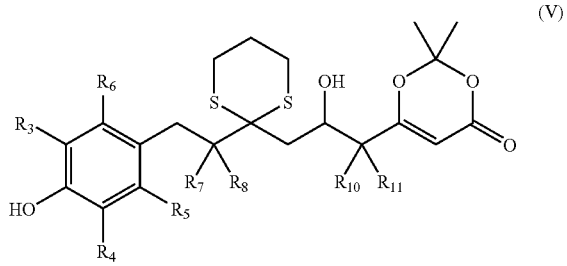

(V)

$R_3$ to $R_8$ and $R_{10}$ to $R_{11}$ being as defined above, reaction of the obtained compound (V) with a compound R'—X—H, (X=O) or (R')(R")—X—H(X=N), R' and R" being as defined above, then reduction with a reducing agent, in particular NaBH$_4$ or NaBH$_4$ and Et$_3$B, or Me$_4$NBH(OAc)$_3$, in order to obtain a compound of formula (I-Z) in which W represents the (II-W) group;

phenolic oxidation of compound (I-Z) obtained with an oxidizing agent such as PIFA and PIDA, in particular PIFA, in order to obtain a compound II in which $R_9$ is OH;

optionally, acylation or alkylation reaction of compound II in which $R_9$ is OH, in order to obtain a compound of general formula II in which $R_9$ represents an O-allyl group, an O-benzyl group, an O—CO-alkyl group, or an O—CO-cycloalkyl group as defined above.

FIG. 5 shows the above method in detail.

The reaction of the aldehyde of formula (IV) with a compound of formula (VII) is carried out under standard basic conditions by means of a base such as LDA (lithium diisopropylamidide) prepared by reaction of n-butyllithium with diisopropylamine, in a polar solvent such as THF at a temperature of −78° C.

The opening of the 1,3-dioxin-4-one ring by an alcohol or an amine is carried out under standard conditions by heating a solvent such as toluene under reflux.

The control of the stereochemistry can be carried out at the reduction stage as a function of the reducing agent used:

the use of a reducing agent such as NaBH$_4$ and Et$_3$B leads to compound (I-Z) in which the diol obtained is a racemic mixture of syn configuration, the use of a reducing agent such as Me$_4$NBH(OAc)$_3$ leads to compound (I-Z) in which the diol obtained is a racemic mixture of anti configuration, According to another embodiment, the method of preparation, defined above, of the compounds of formula (II) in which X=C comprises the following stages:

Reaction of an ester of formula (VIII) below:

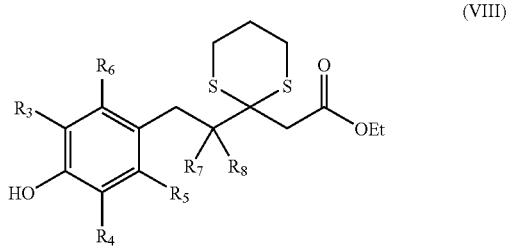

(VIII)

$R_3$ to $R_8$ being as defined above, with a tert-butyl acetate of formula

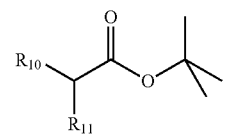

in the presence of a base such as LDA, in order to obtain the compound of formula (IX) below:

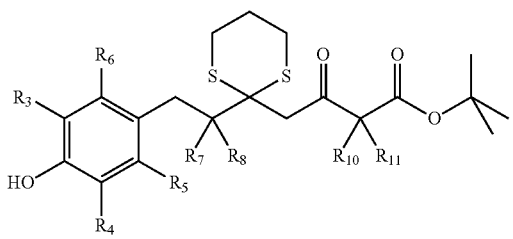

(IX)

$R_3$ to $R_8$ being as defined above, reduction of compound (IX) obtained then reaction with tri-propylsilane chloride in order to produce the compound of formula (X) below:

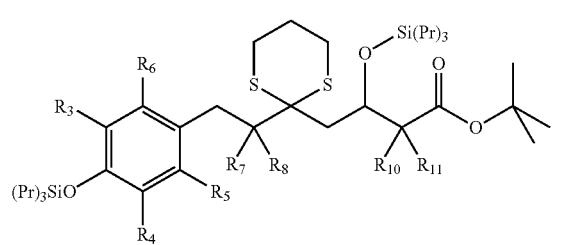

(X)

reduction of compound (X) obtained with a reducing agent such as DIBAL-H in order to produce the compound of formula (XI) below:

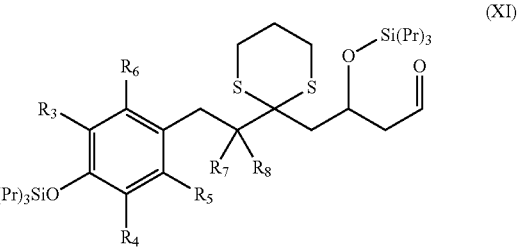

(XI)

Wittig reaction on the obtained compound (XI) in order to obtain a compound of formula (I-Z) in which W represents the (II'-W) group and Y=(Pr)$_3$Si—;

phenolic oxidation of compound (I-Z) obtained with an oxidizing agent such as PIFA and PIDA, in particular PIFA in order to obtain a compound (II) in which $R_9$ is OH and X=C;

optionally, acylation or alkylation reaction of compound (II) in which $R_9$ is OH and X=C, in order to obtain a compound of general formula (II) in which X=C and $R_9$ represents an O-allyl group, an O-benzyl group, an O—CO-alkyl group, or an O—CO-cycloalkyl group as defined above.

FIG. 6 shows the detailed method of preparation of the compounds of formula (II) in which X=C;

The reaction of the ester of formula (VIII) with a tert-butyl acetate is carried out under standard basic conditions by means of a base such as LDA (lithium diisopropylamidide) prepared by reaction of n-butyllithium with diisopropylamine, in a polar solvent such as THF at a temperature of −78° C.

The reduction of the obtained compound (IX) is carried out by means of a reducing agent such as $NaBH_4$ in a polar protic solvent such as methanol at 0° C. The alcohol function as well as the phenol of the obtained compound (X) are subsequently protected by a protective group of the alcohol and phenol functions, in particular by reaction of tri-n-propylsilane chloride in a solvent such as dimethylformamide.

The reduction of the ester function of compound (X) is carried out by a reducing agent such as DIBAL-H (diisobutylaluminium hydride) in a solvent such as toluene at −78° C.

The desired compounds of formula (I-Z) in which W represents the group (II'-W) and Y=$(Pr)_3Si$— are obtained by Wittig reaction on compound (XI).

The Wittig reagents (triphenylphosphine salts) are either commercial, or easily available by techniques known to a person skilled in the art. The Wittig reaction is carried out in a solvent such as dichloromethane at ambient temperature.

According to a preferred embodiment, compound (I-Z) of the method of preparation, defined above, of the compounds of formula (III), is obtained by addition of a nucleophilic by Michael-type addition to a compound of formula (III-3):

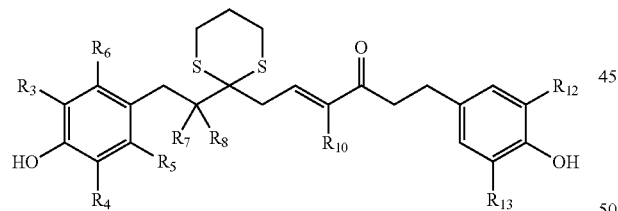

(III-3)

W representing the III-W group and Z representing:
a linear or branched, saturated or unsaturated alkyl group of 1 to 20 carbon atoms, a cycloalkyl group of 3 to 8 carbon atoms,
an S—R" group in which R" is a linear or branched, saturated or unsaturated alkyl of 1 to 20 carbon atoms or a cycloalkyl group of 3 to 8 carbon atoms,
an O-alkyl group as defined above, an O-cycloalkyl group of 3 to 8 carbon atoms, an O—$CH_2$—$CH_2$—$N(CH_3)_2$ group; an O—$CH_2$—CCH group,
an N(R")(R''') group, R" and R''' being as defined above,
said compound (III-3) being obtained by dehydration of a compound (I-Z) in which Z=OH of formula (III-1) below:

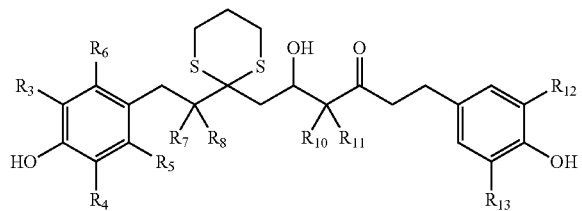

(III-1)

in which $R_{11}$ represents hydrogen.
$R_3$ to $R_8$, $R_{10}$ to $R_{13}$, R" and R''' being as defined above.

FIG. 7 (frame of black lines) shows the detailed method of preparation of the compounds of formula (I-Z) (Z being different from OH).

The compound (I-Z) in which Z=OH is therefore a key intermediate allowing access to the compounds (III-3) as well as direct access to the compounds of formula III in which $R_9$ represents OH.

The dehydration reaction of the compounds of formula (III-1) is carried out by heating under reflux in a solvent such as acetonitrile in the presence of an acid, in particular para-toluene sulphonic acid.

The different additions of nucleophiles by Michael-type addition are carried out according to the techniques well known to a person skilled in the art:
addition of the alkyl groups via a organocuprate (Cluzeau J., Lubell W. D. Conformationally constrained dipeptide surrogates with aromatic side-chains: synthesis of 4-aryl indolizidin-9-one amino acids by conjugate addition to a common a,g-diaminoazelate enone intermediate *J. Org. Chem.* 2004, 69, 1504-1512),
addition of the thiols (Fehr C., Galindo J. Aldols by Michael addition: application of the retro-Michael addition to the slow release of enones *Helv. Chim. Acta* 2005, 88, 2005),
addition of the alcohols (Stewart I. C., Bergman R. G., Toste F. D. Phosphine-catalyzed hydration and hydroalkoxylation of activated olefins: use of a strong nucleophile to generate a strong base *J. Am. Chem. Soc.* 2003, 125, 8696-8697),
addition of the amines (Bartoli G., Bartolacci M., Giuliani A., Marcantoni E., Massaccesi M., Torregiani E Improved heteroatom nucleophilic addition of electron-poor alkenes promoted by $CeCl_3.7\times H_2O/NaI$ system supported on Alumina in solvent-free conditions *J. Org. Chem.* 2004, 70, 169-174).

According to another embodiment, compound (I-Z), in the case where Z is an OH group of the method of preparation, defined above, of a compound of formula (III), is obtained by reaction of an aldehyde of formula (IV) below:

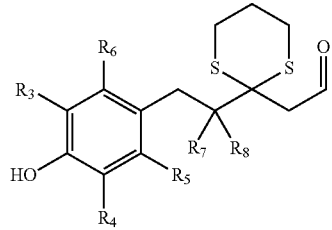

(IV)

$R_3$ to $R_8$ being as defined above,
with a compound of formula (VI) below:

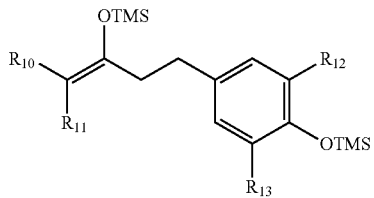

$R_{10}$ to $R_{13}$ being as defined above.

FIG. 7 (frame of thick grey lines) shows the detailed method of preparation of the compounds of formula (I-Z) in which Z represents an OH group.

The compounds of formula (VI) are prepared by the conventional techniques of chemistry and in particular by reaction of LDA in THF at −78° C. then addition of a silane such as trimethylsilane chloride.

The desired (I-Z) compounds are obtained by reaction of the compounds of formula (IV) with the compounds of formula (VI) in an aprotic solvent such as dichloromethane in the presence of $BF_3.OEt_2$ at −78° C. After isolation of the intermediate products thus obtained, the deprotection of the trimethylsilylanes is carried out by reaction of tetrabutylammonium fluoride (TBAF) in an aprotic solvent such as dichloromethane.

According to a preferred embodiment, the method of preparation defined above, of the compounds of formula (III) in which $R_9$ represents:
an OH group,
an O-alkyl group, an O—CO-alkyl group, an O—COCH$_2$CO-alkyl group, said alkyl being saturated or unsaturated, linear or branched with 1 to 20 carbon atoms, an O—CO-cycloalkyl group of 3 to 8 carbon atoms, comprises the following stages:
reaction of an aldehyde of formula (IV) below:

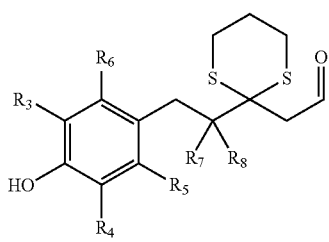

$R_3$ to $R_8$ being as defined above,
with a compound of formula (VI) below:

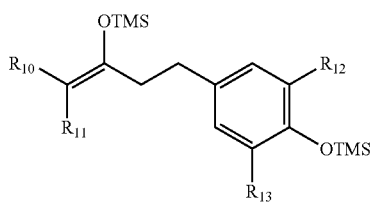

$R_{10}$ to $R_{13}$ being as defined above,
in order to obtain, after treatment with TBAF, a compound (I-Z) in which Z=OH of formula (III-1) below:

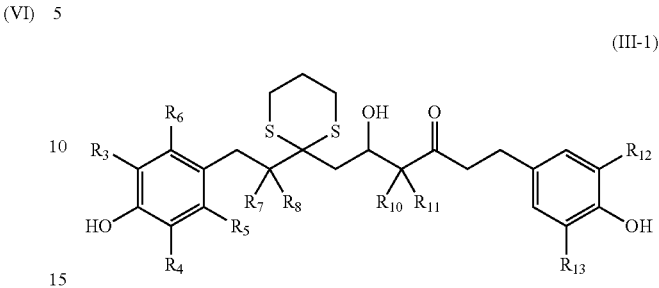

phenolic oxidation with an oxidizing agent such as PIFA and PIDA, in particular PIFA, of the obtained compound (III-1), in order to obtain a compound (III) in which $R_9$ is OH,
optionally, acylation or alkylation reaction of the obtained compound (III), in which $R_9$ is an OH group, in order to obtain a desired compound of formula (III) in which $R_9$ is an O-allyl group, an O-benzyl group, an O—CO-alkyl group, an O—COCH$_2$CO-alkyl group, or an O—CO-cycloalkyl group.

FIG. 8 shows the detailed method of preparation of the compounds of formula (III) in which $R_9$ is an OH group, or $R_9$ is an O-allyl group, an O-benzyl group, an O—CO-alkyl group, an O—COCH$_2$CO-alkyl group, or an O—CO-cycloalkyl group.

According to an even more preferred embodiment, the method of preparation, defined above, of the compounds of formula (III) where $R_9$ is an alkyl group as defined above, comprises the following stages:
addition of a CuXRa nucleophile by Michael-type addition, Ra representing an alkyl group as defined above, on compound (III-3) above obtained in order to produce compound (I-Z) in which Z=Ra of formula (III-4) below:

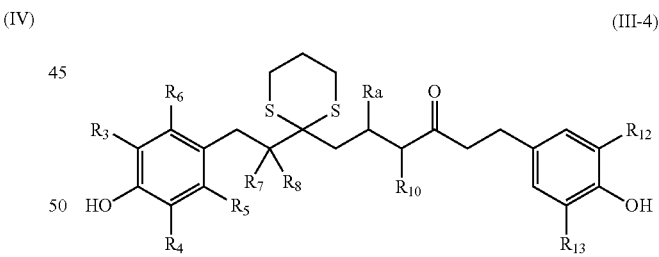

in which $R_3$ to $R_8$, $R_{10}$, $R_{12}$ and $R_{13}$ are as defined above and Ra represents an alkyl group as defined above.
phenolic oxidation with an oxidizing agent such as PIFA and PIDA, in particular PIFA, of the obtained compound (III-4), in order to obtain a compound (III) in which $R_9$ is an alkyl group as defined above.

According to an even more preferred embodiment, the method of preparation, defined above, of the compounds of formula (III) in which $R_9$ is an N(R")(R'") group, R" and R'" being as defined above, comprises the following stages:
addition of an HN(R")(R'") nucleophile by hetero-Michael type addition to compound (III-3) obtained above in order to produce compound (I-Z) in which Z=N(R")(R'") of formula (III-5) below:

(III-5)

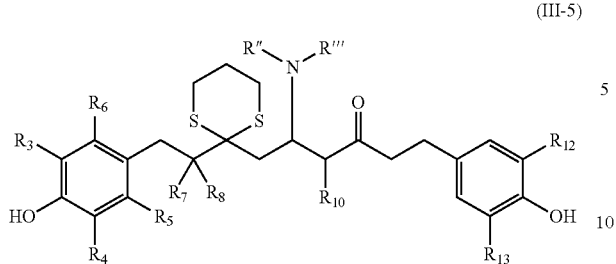

in which $R_3$ to $R_8$, $R_{10}$, $R_{12}$ and $R_{13}$ are as defined above, phenolic oxidation with an oxidizing agent such as PIFA and PIDA, in particular PIFA, of the obtained compound (III-5), in order to obtain a compound (III) in which $R_9$ is an N(R")(R''') group as defined above.

According to another embodiment, the method of preparation, defined above, of the compounds of formula (III) in which $R_9$ is an S(O)—R" group, R" being as defined above, comprises the following stages:

addition of an R"SH nucleophile by hetero-Michael type addition, R" being as defined above, to compound (III-3) obtained above in order to produce compound (I-Z) in which Z=SR" of formula (III-6) below:

(III-6)

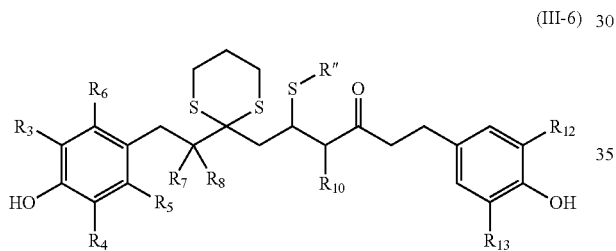

in which $R_3$ to $R_8$, $R_{10}$, $R_{12}$, $R_{13}$ and R" are as defined above.

phenolic oxidation with an oxidizing agent such as PIFA and PIDA, in particular PIFA, of the obtained compound (III-6), in order to obtain a compound (III) in which $R_9$ is an —S(O)R" group, R" being as defined above.

According to a preferred embodiment, the method of preparation, defined above, of the compounds of formula (III) in which $R_9$ is an O-alkyl group as defined above, an O—CH$_2$—CH$_2$—N(CH$_3$)$_2$ group; an O—CH$_2$—CCH group, an

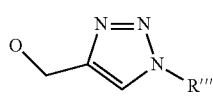

group, R''' being as defined above comprises the following stages:

addition of an ROH nucleophile by hetero-Michael type addition, R being an alkyl as defined above, an —CH$_2$—CH$_2$—N(CH$_3$)$_2$ group; an —CH$_2$—CCH group, to compound (III-3) obtained above in order to produce compound (I-Z) in which Z=OR of formula (III-2) below:

(III-2)

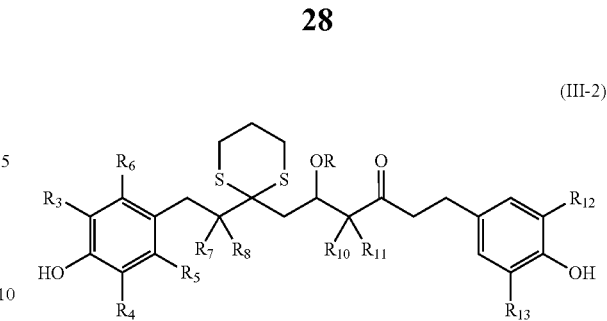

in which $R_3$ to $R_8$ and $R_{10}$, $R_{12}$ and $R_{13}$ are as defined above, $R_{11}$ represents hydrogen, phenolic oxidation with an oxidizing agent such as PIFA and PIDA, in particular PIFA, of the obtained compound (III-2), in order to obtain a compound (III) in which $R_9$ is an O-alkyl group as defined above, an O—CH$_2$—CH$_2$—N(CH$_3$)$_2$ group; an O—CH$_2$—CCH group, optionally, addition reaction of compound (III) obtained above in which $R_9$ is an O—CH$_2$—CCH group, with N$_3$—R''' in order to obtain the desired compound of formula (III) in which $R_9$ is an

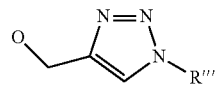

group, R''' being as defined above.

FIG. 9 shows the detailed method of preparation of the compounds of formula (III) in which $R_9$ is an alkyl group, an NR"R''' group, an S(O)R" group, an O-alkyl group, an O—CH$_2$—CH$_2$—N(CH$_3$)$_2$ group; an O—CH$_2$—CCH group or an

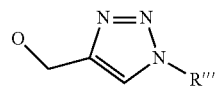

group, R''' being as defined above.

The compounds of general formula (III) in which $R_9$ is an

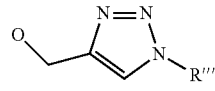

group are obtained by adding an (N$_3$—R''') azide in the presence of copper sulphate and sodium ascorbate. (Kolb H. C., Finn M. G., Sharpless K. B. Click chemistry: diverse chemical function from a few good reactions *Angew Chem. Int. Ed.* 2001, 40, 2004-2021; Bock V. D., Hiemstra H., van Maarseveen J. H. Cu$^I$-catalysed alkyne-azide "Click" cycloaddition from a mechanistic and synthetic perspective *Eur. J. Org. Chem.* 2006, 51-68).

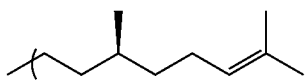

- 2M: monensin

Figure 1:
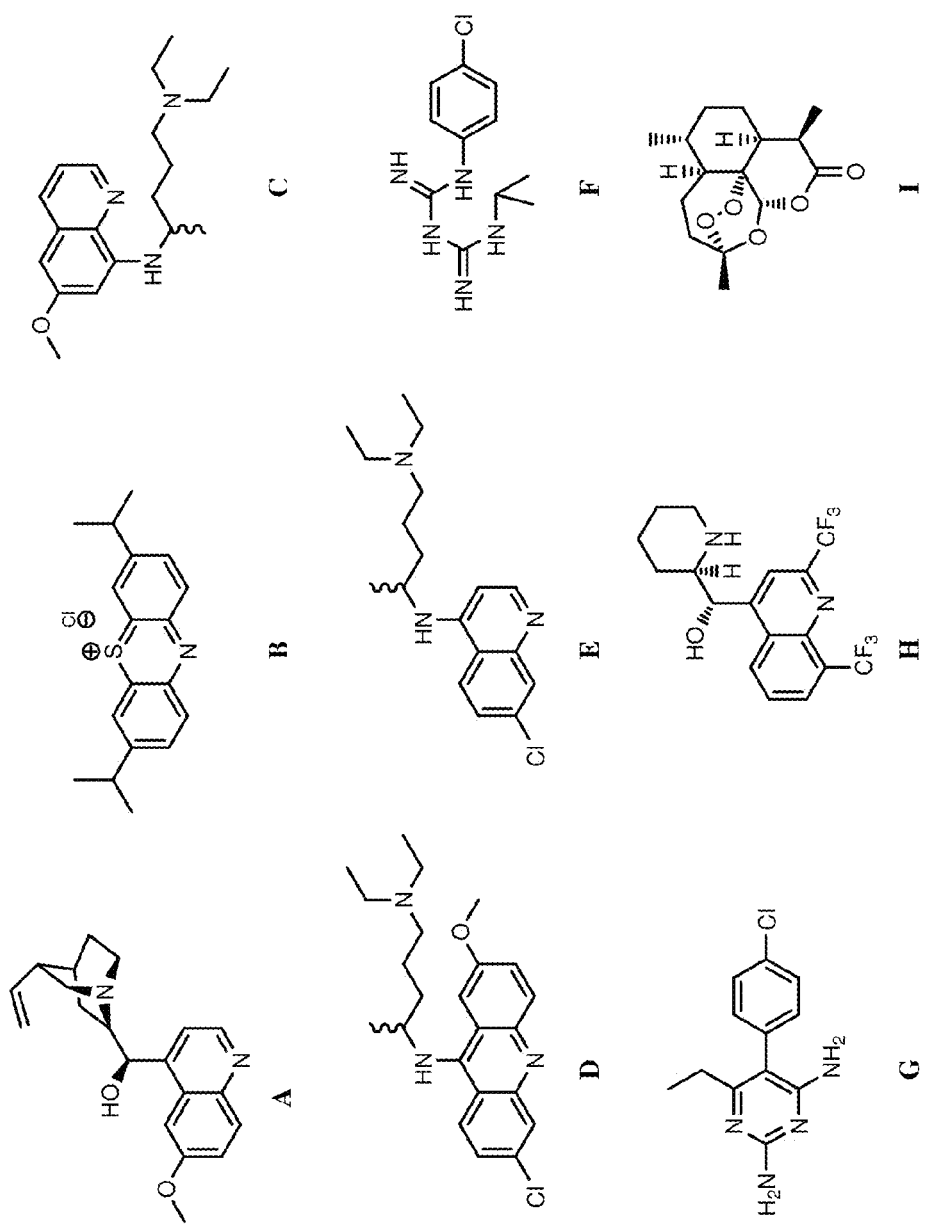
FIG. 1A to 1I shows previously used antimalarial molecules:
- 1A: quinine
- 1B: methylene blue
- 1C: pamaquine
- 1D: mepacrine
- 1E: chloroquine
- 1F: proguanil
- 1G: pyrimethamine
- 1H: mefloquine
- 1I: artemisinin
Figure 2:
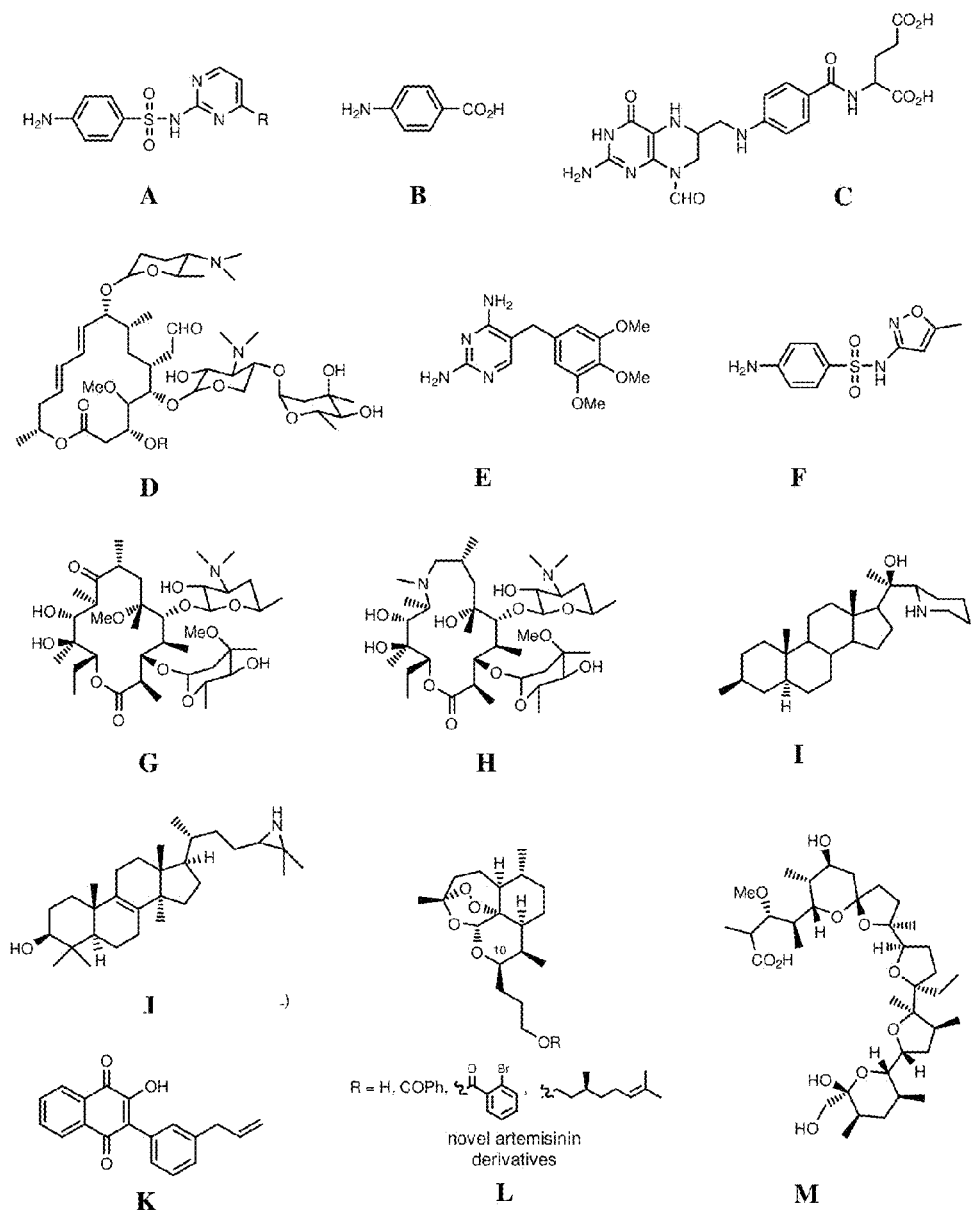
FIG. 2A to 2M shows molecules used or undergoing investigation for the treatment of toxoplasmosis:
- 2A: R=H, sulphadiazine; R=Me, sulphamerazine
- 2B: PABA
- 2C: folinic acid
- 2D: R=H, spiramicine I; R=COMe, spiramicine II, R=H, spiramicine III
- 2E: trimethropine
- 2F: sulphamethoxazole
- 2G: clarithromycin
- 2H: azithromycin
- 2I: 22,26-azasterol (AZA)
- 2J: 24,25 (R,S)-epiminolanosterol (EIL)
- 2K: PHNQ-6
- 2L: R=H, COPh, COPh(2-Br)
Figure 3:
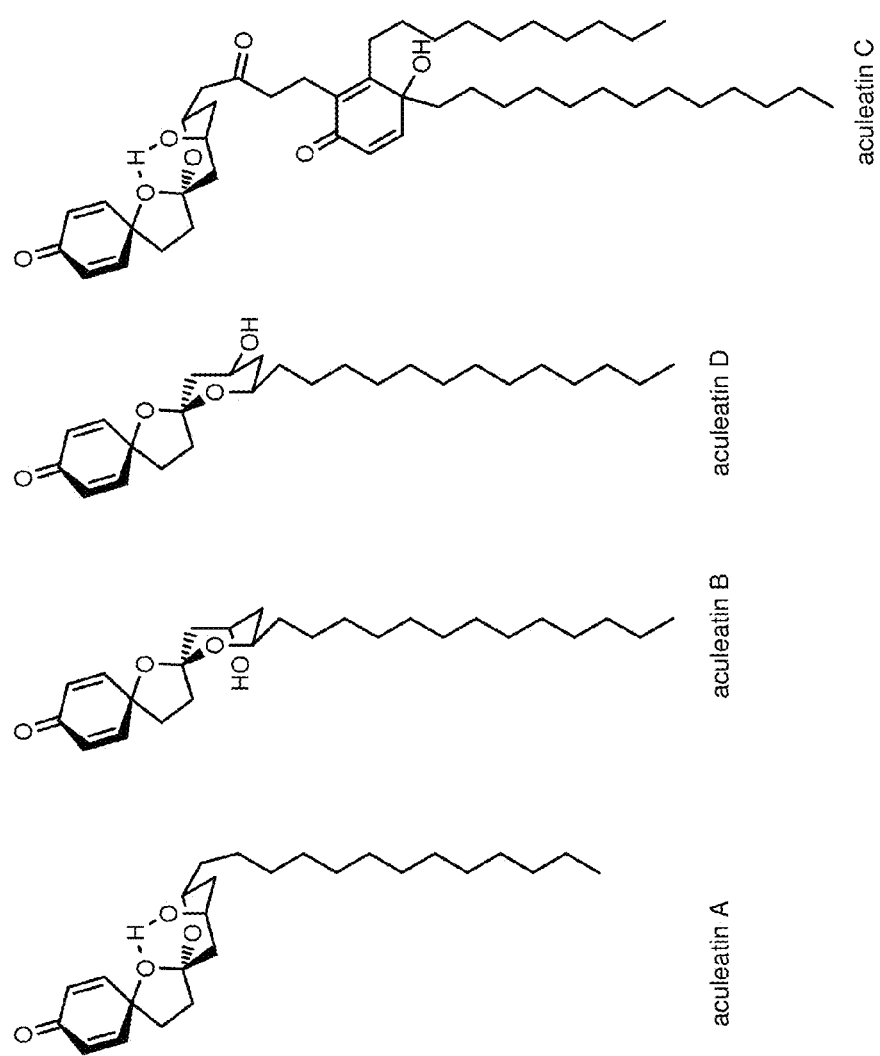

FIG. 3 shows the structure of the aculeatines A, B, C and D.

Figure 4:
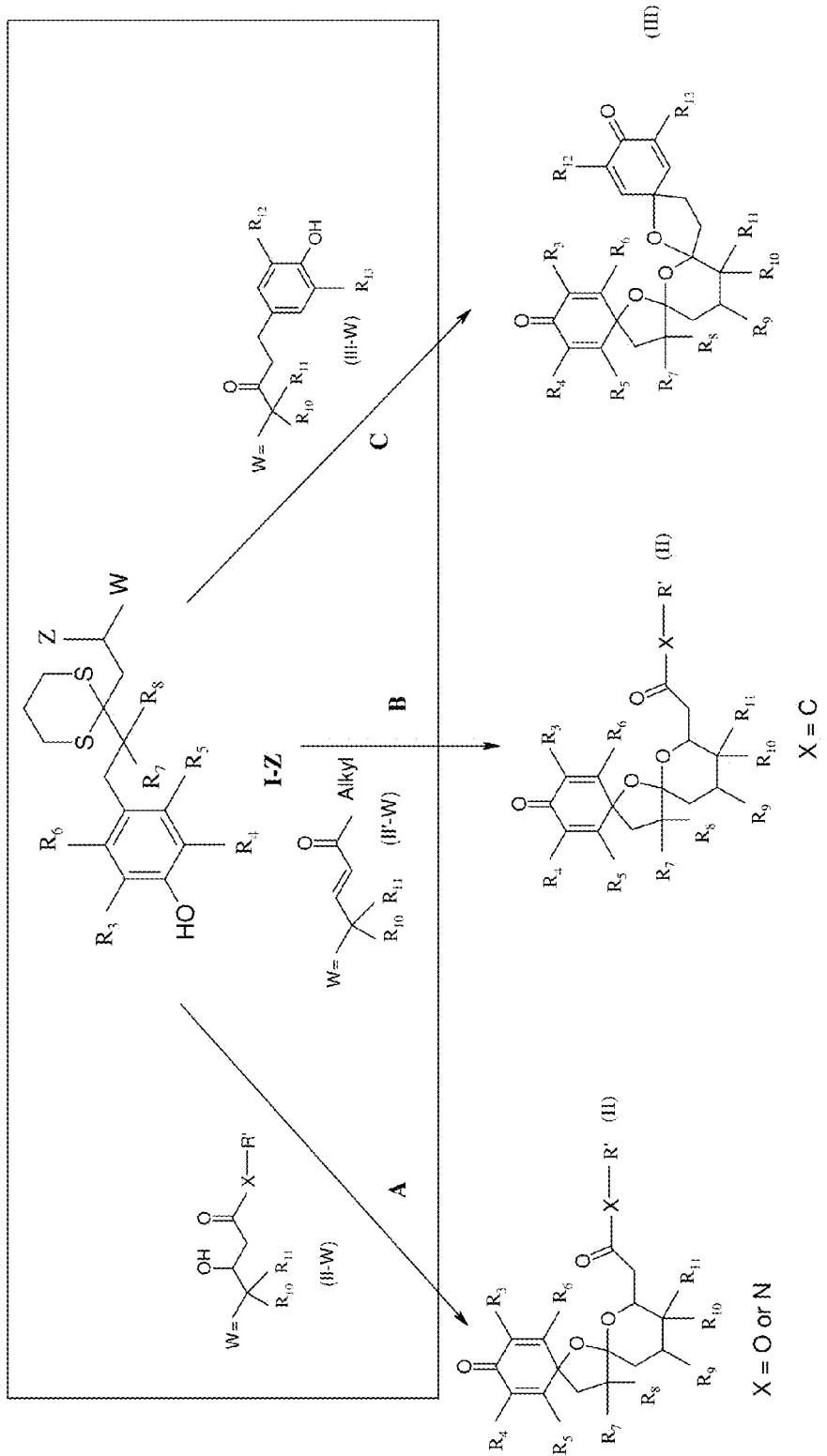

FIG. 4 shows the different possibilities for obtaining the compounds of the invention:
A: obtaining the compounds (II), in which X=O, N by phenolic oxidation,
B: obtaining the compounds (II) in which X=C, by phenolic oxidation,
C: obtaining the compounds (III), by phenolic oxidation.

Figure 5:
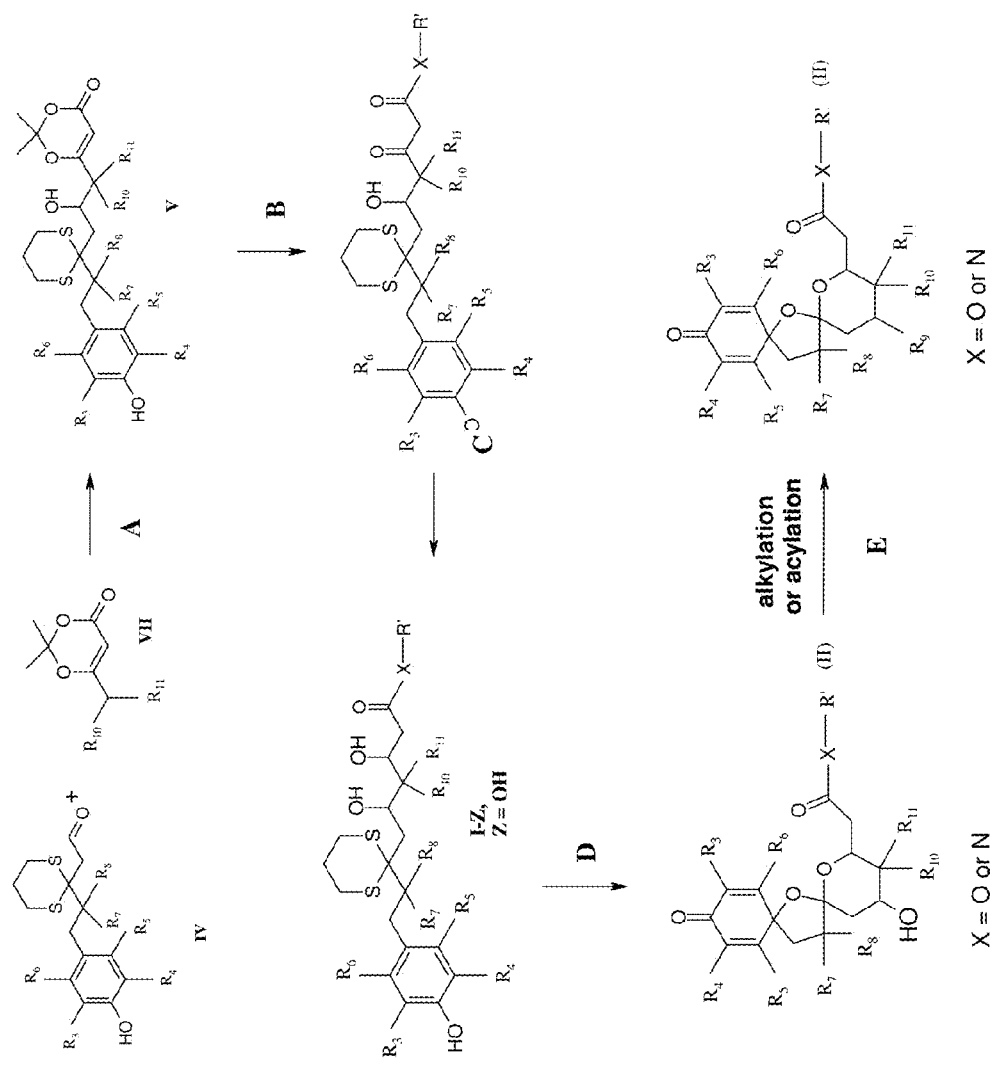

FIG. 5 shows the process of synthesis of the compounds of formula (II) in which X=O or N:
A: addition of compound (VII) to compound (IV) by treatment with LDA in THF at −78° C.,
B and C: addition of an amine or an alcohol to compound (V) by heating under reflux in toluene then reduction of the ketone function of the compound obtained by NaBH$_4$, NaBH$_4$ and Et$_3$B, or Me$_4$NBH(OAc)$_3$,
D: phenolic oxidation by an oxidizing agent such as PIFA or PIDA, at ambient temperature in a mixture of solvents such as acetone and water.
E: optionally, acylation reaction in dichloromethane by reaction with an anhydride, an acid chloride or alkylation with an allyl or benzyl chloride in a solvent, in particular dichloromethane.

Figure 6:
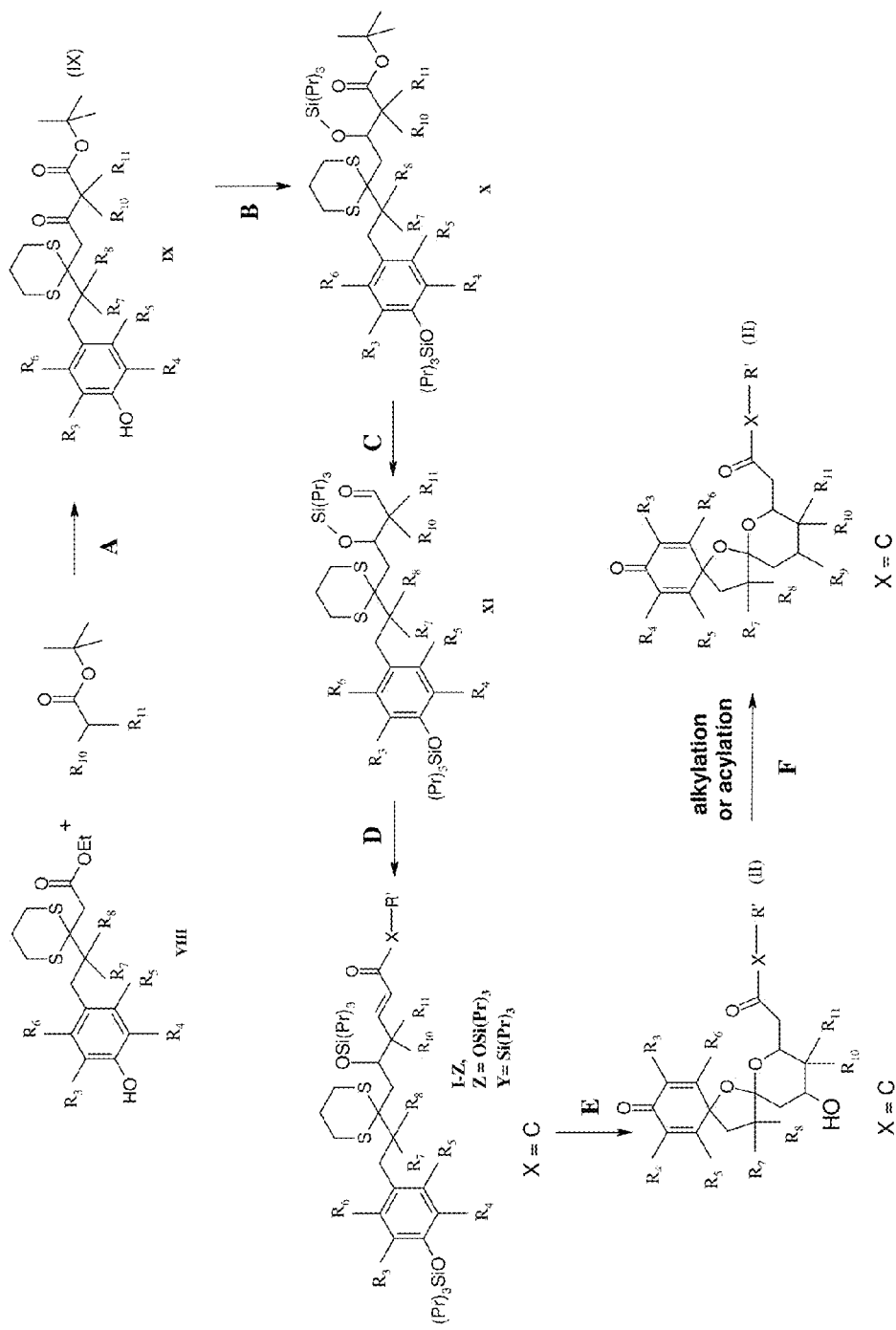

FIG. 6 represents the method of synthesis of the compounds of formula (II) in which X=C:
A: addition of a tert-butyl acetate to compound (VIII) by treatment with LDA in THF at −78° C.,
B: reduction of the ketone function of compound (IX) by NaBH$_4$ in methanol at 0° C. then protection of the alcohol and phenol function by a protective group, in particular tripropylsilane chloride.

C: reduction of the ester function by DIBAL-H in toluene at −78° C.,
D: Wittig reaction of compound (XI) in dichloromethane at ambient temperature with a triphenylphosphine salt,
E: phenolic oxidation by an oxidizing agent such as PIFA or PIDA, at ambient temperature in a mixture of solvents such as acetone and water.

Figure 7:
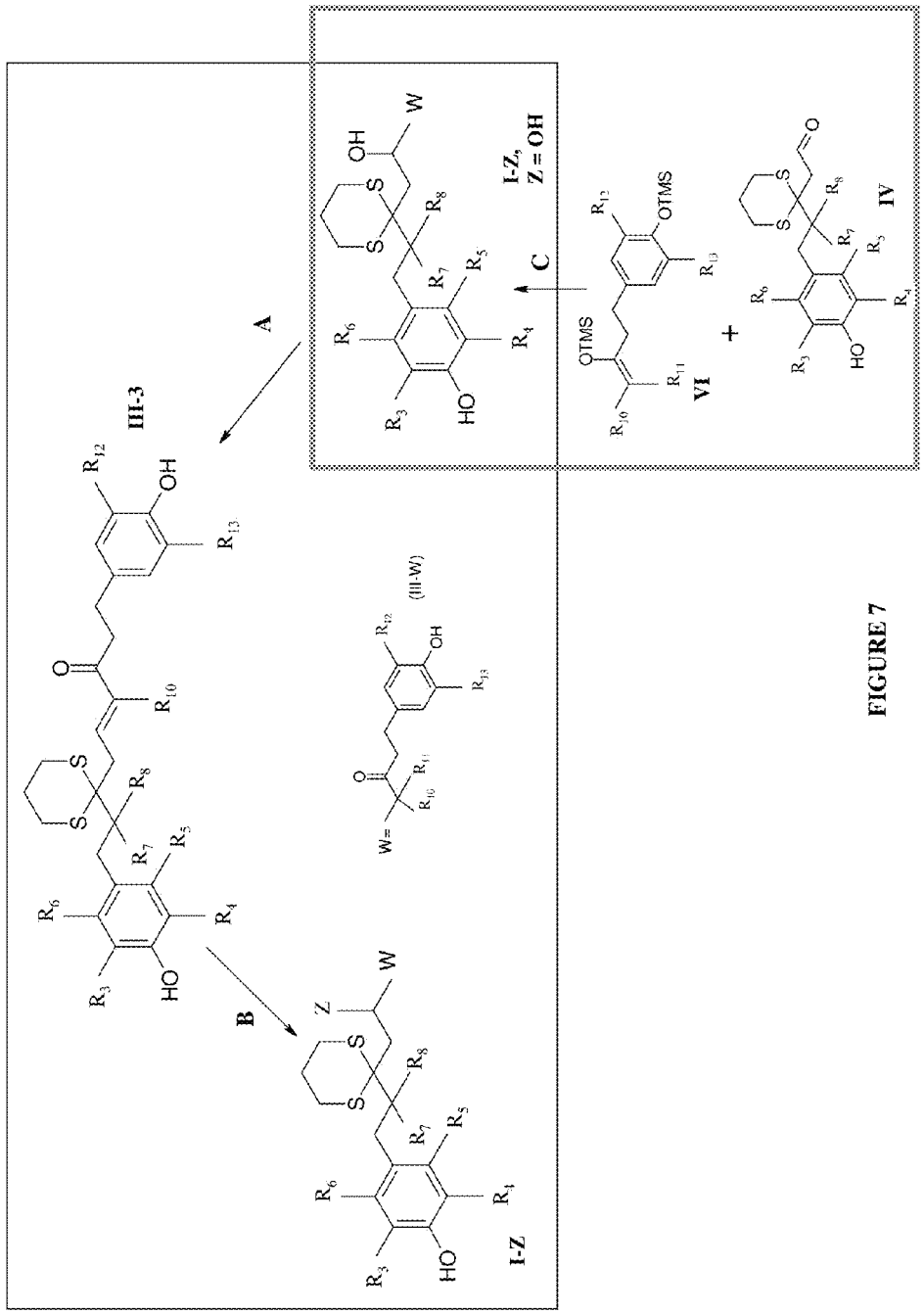

FIG. 7 shows:
frame of black lines: the method for preparing the compounds of formula (I-Z) (Z being different from OH) from the key intermediate (I-Z) in which Z=OH:
A: dehydration of compound (I-Z) (Z=OH) by heating under reflux in a solvent such as acetonitrile in the presence of an acid, in particular para-toluene sulphonic acid,
B: addition reaction of a (CuX-alkyl, HS—R″, HO-alkyl, or HN(R″)(R‴)) nucleophile by Michael-type addition to the compound of formula (III-3).

frame of thick grey lines: the method for preparing the compounds of formula (I-Z) in which Z represents an OH group:
C: addition reaction of a compound of formula (VI) on a compound of formula (IV) in an aprotic solvent such as dichloromethane in the presence of BF$_3$.OEt$_2$ at −78° C. After isolation of the intermediate products thus obtained, the deprotection of the trimethylsilylanes is carried out by reaction of tetrabutylammonium fluoride (TBAF) in an aprotic solvent such as dichloromethane.

Figure 8:
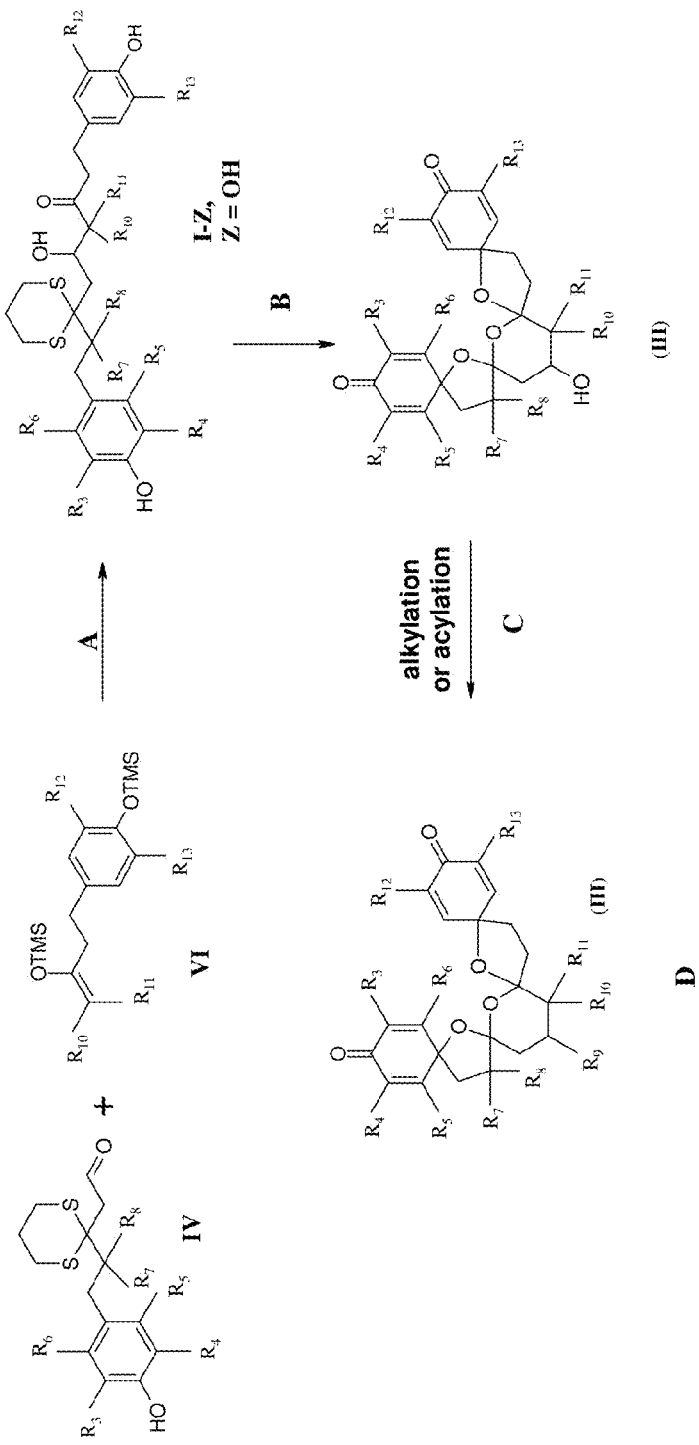

FIG. 8 shows the method for preparing the compounds of formula (III) in which R$_9$ is an OH group, or R$_9$ is an O-allyl group, an O-benzyl group, an O—CO-alkyl group, an O—COCH$_2$CO-alkyl group, or R$_9$ is an O—CO-cycloalkyl group:
A: addition of compound (VI) to the aldehyde (IV) in THF at −78° C.,
B: phenolic oxidation by an oxidizing agent such as PIFA or PIDA, at ambient temperature in a mixture of solvents such as acetone and water,
C: optionally, acylation reaction in dichloromethane by reaction with an anhydride, an acid chloride or alkylation with an allyl or benzyl chloride in a solvent, in particular dichloromethane.

Figure 9:
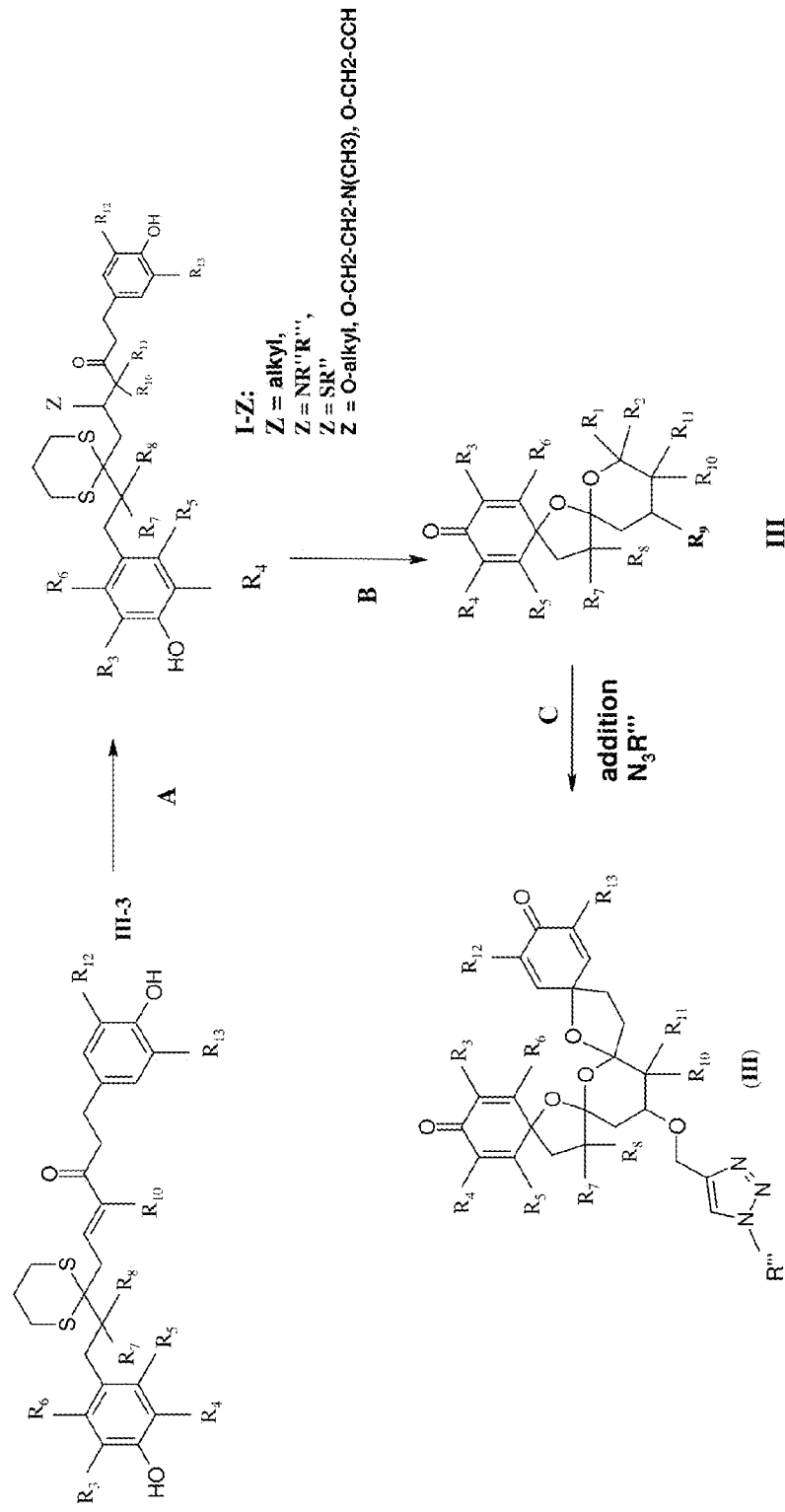

FIG. 9 shows the method for preparing the compounds of formula (III) in which R$_9$ is an alkyl group, an NR″R‴ group, an S(O)R″ group, an O-alkyl group, an O—CH$_2$—CH$_2$—N(CH$_3$)$_2$ group; an O—CH$_2$—CCH group or an

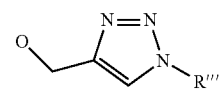

group.
A: addition of a nucleophile (CuX-alkyl, HS—R″, HO-alkyl, or HN(R″)(R‴) nucleophile.
B: phenolic oxidation by an oxidizing agent such as PIFA or PIDA, at ambient temperature in a mixture of solvents such as acetone and water,
C: optionally, addition of an (N$_3$—R‴) azide in the presence of copper sulphate and sodium ascorbate.

Figure 10:
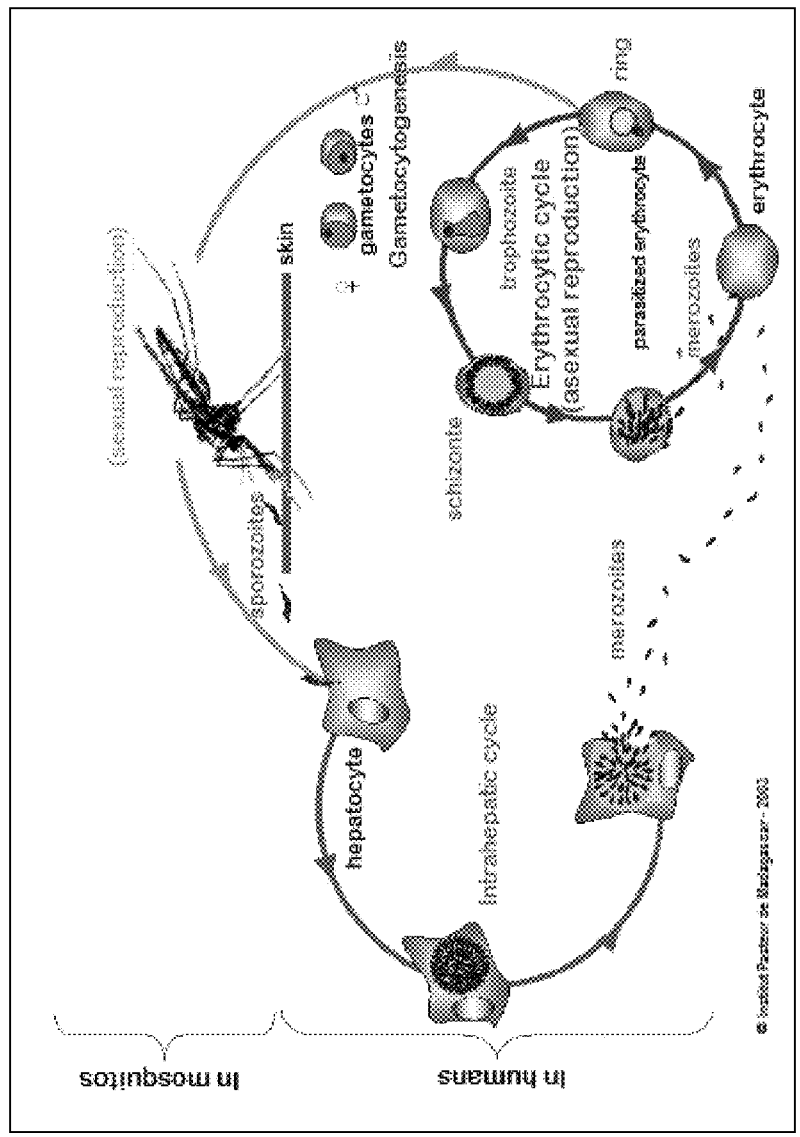

FIG. 10 shows the different biological cycles of *Plasmodium* Spp.

Figure 11:
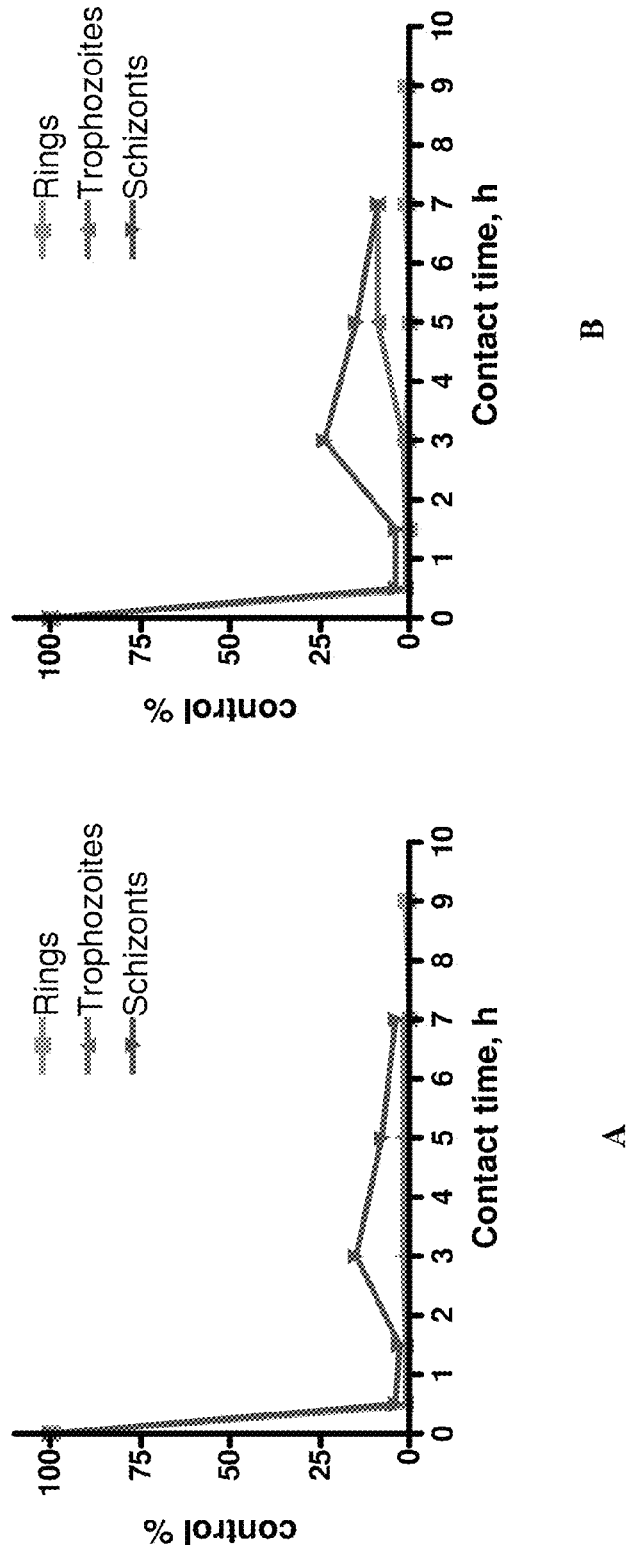

FIG. 11 shows the results obtained with the compounds of the invention on the different blood stages (rings, trophozoites and schizontes) of the development of the parasite:
A: compound 16c
B: compound 16d

EXPERIMENTAL PART

I) Synthesis of the Compounds 3-(4-benzyloxyphenyl)propionic acid (2)

A solution of 3-(4-hydroxyphenyl)propionic acid (20.0 g, 0.12 mol) and benzyl bromide (21.5 mL, 0.18 mol) in 155 mL of THF is added, at ambient temperature to a 1N aqueous solution of soda (301 mL). The phase transfer catalyst, Bu$_4$NHSO$_4$ (155 mg, 0.45 mmol), is finally added. The reaction medium is stirred overnight before being heated for 1 h at 80° C. After cooling down, 150 mL of a 1N aqueous solution of HCl is added slowly. After extraction with CH$_2$Cl$_2$, the organic phases are dried over MgSO$_4$, filtered and concentrated under vacuum. Purification is carried out on silica gel (CH$_2$Cl$_2$ up to CH$_2$Cl$_2$/MeOH 95:5) in order to produce compound 2 (30.4 g, 0.12 mol, 99%) in the form of a white solid.

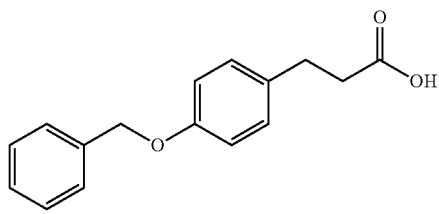

2

$C_{16}H_{16}O_3$
M=256.3 g.mol$^{-1}$
NMR $^1$H (400 MHz, CDCl$_3$): δ=2.63 (t, J=7.7 Hz, 2H); 2.88 (t, J=7.7 Hz, 2H); 5.02 (s, 2H); 6.90 (d, J=8.6 Hz, 2H); 7.11 (d, J=8.6 Hz, 2H); 7.28-7.44 (m, 5H).
NMR $^{13}$C (100 MHz, CDCl$_3$): δ=29.9; 36.1; 70.2; 115.1; 127.7; 128.1; 128.8; 129.4; 132.7; 137.2; 157.5; 179.6.
HRMS (ESI+): m/z calculated for $C_{16}H_{16}O_3$Na 279.0997, found 279.0999.

ethyl 5-(4-Benzyloxyphenyl)-3-oxopentanoate (3)

Oxalyl chloride (20.4 mL, 0.24 mol). is added, dropwise, under argon and at −78° C. to a solution of the acid 2 (30.41 g, 0.12 mol) in 300 mL of anhydrous.CH$_2$Cl$_2$. In the case where the reaction does not start by itself, 2 drops of DMF are added. After stirring for 3 h at ambient temperature, the reaction medium is concentrated under vacuum in order to produce a yellow oil. Simultaneously, anhydrous pyridine (19.2 mL, 0.24 mol) is added, dropwise, under argon and at 0° C. to a solution of Meldrum's acid (17.10 g, 0.12 mol) in 115 mL of anhydrous CH$_2$Cl$_2$. After stirring for 1 hour at 0° C., the acyl chloride obtained previously in solution in 55 mL of anhydrous CH$_2$Cl$_2$ is added slowly. The reaction medium is added over 16 h at 0° C. then for 2 h at ambient temperature before being quenched by the addition of a 1N aqueous solution of HCl. After extraction with CH$_2$Cl$_2$, the organic phases are dried over MgSO$_4$, filtered and concentrated under vacuum. The orange oil thus obtained, in solution in 180 mL of absolute ethanol, is taken to reflux for 2.5 h. The reaction medium is then concentrated under vacuum. Purification is carried out on silica gel (cyclohexane/AcOEt 9:1) in order to produce compound 3 (23.74 g, 0.07 mol, 61%) in the form of a colourless oil.

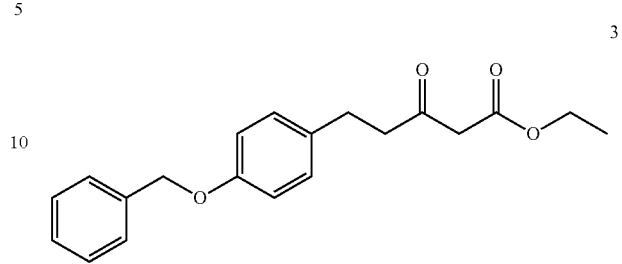

3

$C_{20}H_{22}O_4$
M=326.4 g.mol$^{-1}$
NMR $^1$H (400 MHz, CDCl$_3$): δ=1.26 (t, J=7.2 Hz, 3H); 2.79-2.92 (m, 4H); 3.41 (s, 2H); 4.17 (q, J=7.2 Hz, 2H); 5.03 (s, 2H); 6.89 (d, J=8.4 Hz, 2H); 7.09 (d, J=8.4 Hz, 2H); 7.28-7.45 (m, 5H).
NMR $^{13}$C (100 MHz, CDCl$_3$): δ=14.2; 28.7; 44.8; 49.6; 61.5; 70.1; 115.0; 127.6; 128.0; 128.7; 129.4; 133.0; 137.2; 157.4; 167.2; 202.1.
Elementary analysis: calculated for $C_{20}H_{22}O_4$: C, 73.60; H, 6.79. found: C, 73.88; H, 6.99.

ethyl 5-(4-Hydroxyphenyl)-3-oxopentanoate (4)

2.0 g of 10% Pd/C is added, at ambient temperature, to a solution of the protected phenol 3 (23.74 g, 0.07 mol) in 320 mL of AcOEt. The reaction medium is stirred overnight under an atmosphere of H$_2$ then it is filtered on Celite®, washed with AcOEt. The filtrate is then concentrated under vacuum in order to produce the expected product 4 (17.02 g, 0.07 mol, 99%) in the form of a colourless oil. The crude product is used in the following stage without other purification.

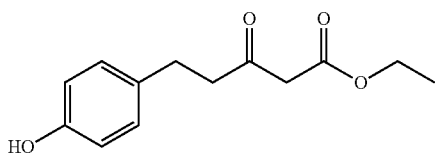

4

$C_{13}H_{16}O_4$
M=236.3 g.mol$^{-1}$
NMR $^1$H (400 MHz, CDCl$_3$): δ=1.26 (t, J=7.1 Hz, 3H); 2.80-2.86 (m, 4H); 3.43 (s, 2H); 4.18 (q, J=7.1 Hz, 2H); 6.75 (d, J=8.4 Hz, 2H); 7.01 (d, J=8.4 Hz, 2H).
NMR $^{13}$C (100 MHz, CDCl$_3$): δ=14.2; 28.8; 45.0; 49.6; 61.8; 115.6; 129.6; 132.4; 154.4; 167.6; 202.8.
Mass (IE): m/z (%) 236 [M]$^+$ (94), 190 (42), 164 (66), 147 (92), 108 (100).
HRMS (IE): m/z calculated for $C_{13}H_{16}O_4$ 236.1049, found 236.1070.

{2-[2-(4-Hydroxyphenyl)-ethyl]-[1,3]-dithian-2-yl}-ethyl acetate (4')

10.1 mL of BF$_3$.OEt$_2$ is added, dropwise, under argon and at ambient temperature to a solution of β-ketoester 4 (17.02 g, 0.07 mol) and 1,3-propanedithiol (7.30 mL, 0.07 mol) in 90 mL of anhydrous CH$_2$Cl$_2$. After stirring overnight, the reaction medium is quenched by the addition of 90 mL of a 1N aqueous solution of NaOH. After extraction with $CH_2Cl_2$, the organic phases are dried over $MgSO_4$, filtered and concentrated under vacuum. Purification is carried out on silica gel (cyclohexane/AcOEt 85:15) in order to produce compound 4' (18.64 g, 0.06 mol, 79%) in the form of a colourless oil.

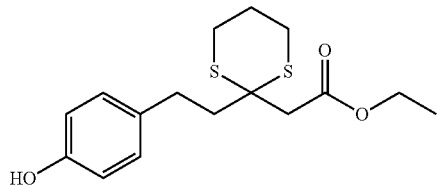

4'

$C_{16}H_{22}O_3S_2$
M=326.5 g.mol$^{-1}$
NMR $^1$H (400 MHz, CDCl$_3$): δ=1.29 (t, J=7.2 Hz, 3H); 1.84-1.96 (m, 1H); 2.05-2.14 (m, 1H); 2.30-2.36 (m, 2H); 2.73-2.84 (m, 4H); 3.04 (ddd, J=14.0, 10.8, 4.8 Hz, 2H); 3.12 (s, 2H); 4.18 (q, J=7.2 Hz, 2H); 6.76 (d, J=8.8 Hz, 2H); 7.07 (d, J=8.8 Hz, 2H).
NMR $^{13}$C (100 MHz, CDCl$_3$): δ=14.4; 25.1; 26.6; 27.1; 41.9; 43.0; 50.2; 61.1; 115.5; 129.8; 133.6; 154.2; 169.4.
Mass (IE): m/z (%) 326 [M]$^+$ (37), 251 (10), 239 (20), 219 (85), 205 (42), 145 (52), 107 (100).
HRMS (IE): m/z calculated for $C_{16}H_{22}O_3S_2$ 326.1010, found 326.1034.

Alternative Synthesis Route for Compound 4'

3-(4 Hydroxy-phenyl)-propionic acid ethyl ester (4'-1)

4 drops of concentrated HCl are added, under stirring, to a solution of commercial 3-(4 Hydroxy-phenyl)-propionic acid (13.08 g; 78.79 mmol) in 100 mL of ethanol. The reaction medium is heated to reflux in a bath at 145° C. overnight. The ethanol is evaporated off and ethyl acetate is added. The organic phase is washed with a saturated NaHCO$_3$ solution and with a NaCl solution. After drying over MgSO$_4$ and evaporation, an oil is obtained. This latter is distilled by Kugelrohr (150-175° C.; 1.2 mmbar). A transparent oil which crystallizes is obtained in order to produce the expected compound 4'-1 (13.8 g; 71.1 mmol; 90%) in the form of a white solid.

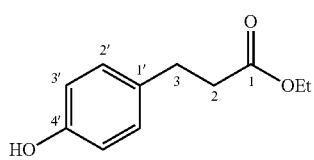

4'-1

$C_{11}H_{14}O_3$
M=194 g.mol$^{-1}$
$R_f$=0.31 (1:4 ethyl acetate/cyclohexane)
UV: 278, 224, 199 nm.
IR $v_{max}$ (film, cm$^{-1}$): 3391, 2983, 1709, 1615, 1517, 1447, 1374, 1225, 1036.
$^1$H NMR (400 MHz, CDCl$_3$): δ=1.22 (t, J=7.2 Hz, 3H, —OCH$_2$CH$_3$), 2.59 (t, J=7.9 Hz, 2H, 2×H3), 2.86 (t, J=7.9 Hz, 2H, 2×H2), 4.12 (q, J=7.2 Hz, 2H, —OCH$_2$CH$_3$), 6.75 (d, J=8.5 Hz, 2H, 2×H2'), 7.01 (d, J=8.5 Hz, 2H, 2×H3').
$^{13}$C NMR (100 MHz, CDCl$_3$): δ=14.2 (—OCH$_2$CH$_3$), 30.21 (C3), 36.5 (C2), 60.9 (—OCH$_2$CH$_3$), 115.5 (2×C2'), 129.4 (2×C3'), 132.1 (C1'), 154.5 (C4'), 174.2 (C1).
LRMS (ESI+): m/z (%) 217 (26) [M+Na]$^+$, 107 (100).

tert-butyl 5-(4-Hydroxyphenyl)-3-oxopentanoate (4'-2)

Diisopropyl amine (4.65 mL; 33.0 mmol; 5 equiv.) in anhydrous THF (25 mL) is placed in a 100 mL flask under a nitrogen atmosphere. The solution is cooled down to −20° C. and n-BuLi at 2.5 M in hexane (13.5 mL; 33.0 mmol; 5 equiv.) is added dropwise. The solution is then stirred for 15 min at 0° C. then cooled down to −78° C. The t-butyl acetate (2.74 mL; 33.0 mmol; 5 equiv.) is injected dropwise. After 30 min, the ester 4'-1 (1.29 g; 6.6 mmol), in anhydrous THF (15 mL), is injected dropwise by a syringe. The reaction mixture is stirred for 30 min at −78° C., then for a further 30 min at 0° C. The reaction is stopped by the addition of 15 mL of acetic acid. The solution is washed with 50 mL of a saturated solution of K$_2$CO$_3$. The product is extracted with 3×100 mL of ethyl acetate, dried with MgSO$_4$ and the solvent is then evaporated off. After column chromatography (AcOEt/cyclohexane 1:3), the product 4'-2 (1.36 g; 78%) is isolated in the form of a yellow oil.

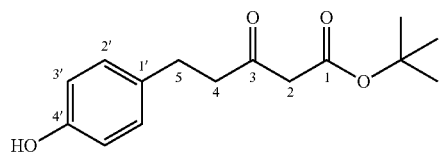

4'-2

$C_{15}H_{20}O_4$
M=264 g.mol$^{-1}$
$R_f$=0.23 (1:3 ethyl acetate/cyclohexane)
IR $v_{max}$ (film, cm$^{-1}$): 3457, 3403, 3331, 2978, 2932, 1738, 1713, 1614, 1597, 1516, 1454, 1368, 1323, 1263, 1161, 1080, 951, 831, 768 cm$^{-1}$.
UV: 286, 280, 224, 205 nm.
$^1$H NMR (300 MHz, CDCl$_3$): δ=1.47 (s, 9H, —OC(CH$_3$)$_3$), 2.78-2.82 (m, 4H, 2×H4, 2×H5), 3.34 (s, 2H, 2×H2), 6.75 (d, J=8.3 Hz, 2H, 2×H3'), 6.99 (d, J=8.3 Hz, 2H, 2×H2').
$^{13}$C NMR (75 MHz, CDCl$_3$): δ=27.8 (—OC(CH$_3$)$_3$), 28.5 (C5), 44.7 (C4), 50.6 (C2), 81.6 (—OC(CH$_3$)$_3$), 115.3 (2×C3'), 129.2 (2×C2'), 131.9 (C4'), 154.3 (C1'), 166.7 (C1).
LRMS (DCI, NH$_3$+isobutane): m/z (%) 282 (6) [M+NH$_4$]$^+$, 265 (5) [M+H]$^+$, 226 (39), 209 (43), 107 (100).

{2-[2-(4-Hydroxyphenyl)-ethyl]-[1,3]-dithian-2-yl}-ethyl acetate (4')

The ester 4'-2 (1.118 g, 4.23 mmol) in anhydrous CH$_2$Cl$_2$ (11 mL), 1.3 propanedithiol (456 mg, 4.23 mmol) and 0.82 mL of BF$_3$OEt$_2$, are added under argon and at ambient temperature into a 100 mL flask. After stiffing for 2 h (maximum duration not to be exceeded, in order not to obtain an unwanted product), the reaction is stopped by the addition of 8 mL of 1N NaOH. The medium is reacidified by 8 mL of 1N HCl. After extraction with CH$_2$Cl$_2$ then with AcOEt, the organic phases are dried over MgSO$_4$, filtered and concentrated under vacuum.

The product is used directly for the following stage

The acid obtained above is introduced into a flask with 40 mL of ethanol as well as 10 drops of concentrated HCL. The reaction mixture is stirred and heated to reflux in a bath at 145° C. for 2 nights. After evaporation and column chromatography (AcOEt/cyclohexane 1.5:8.5), the ester 4' (0.709 g) is isolated in the form of a colourless oil, with a yield of 51.3% from the molecule 4'-2.

{2-[2-(4-Hydroxyphenyl)-ethyl]-[1,3]-dithian-2-yl}-acethaldehyde (1)

A commercial 1.5 M solution of DIBAL-H in toluene (14.2 mL, 21.3 mmol) is added dropwise, under argon and at −78° C., to a solution of the ester 4' (3.32 g, 10.2 mmol) in 80 mL of anhydrous toluene. After stirring for 20 min at this temperature, the reaction medium is quenched by the addition of 17 mL of MeOH. After returning to ambient temperature (1 h), a 1N aqueous solution of NaOH is added. After extraction with AcOEt, the organic phases are dried over MgSO$_4$, filtered and concentrated under vacuum. Purification is carried out on silica gel (cyclohexane/AcOEt 8:2) in order to produce the aldehyde 1 (2.09 g, 7.4 mmol, 73%) in the form of a white solid.

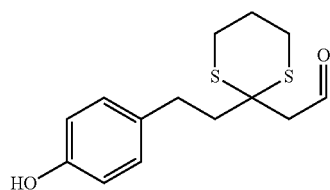

1

$C_1H_{18}O_2S_2$
M=282.4 g.mol$^{-1}$

NMR $^1$H (400 MHz, CDCl$_3$): δ=1.92-2.18 (m, 2H); 2.22-2.30 (m, 2H); 2.72-2.80 (m, 2H); 2.85-2.93 (m, 4H); 2.94 (d, J=2.6 Hz, 2H); 6.77 (d, J=8.4 Hz, 2H); 7.04 (d, J=8.4 Hz, 2H); 9.82 (t, J=2.6 Hz, 1H).
NMR $^{13}$C (100 MHz, CDCl$_3$): δ=24.7; 26.3; 30.0; 42.7; 49.3; 50.5; 115.6; 129.7; 133.2; 154.2; 200.5.
Mass (IE): m/z (%) 282 [M]$^+$ (8), 264 [M−H$_2$O]$^+$ (8), 207 (5), 175 (21), 107 (100).
Elementary analysis: calculated for $C_{14}H_{18}O_2S_2$: C, 59.54; H, 6.42. found: C, 59.32; H, 6.51.

Example 1

Preparation of 6-(2-Hydroxy-3-{2-[2-(4-hydroxyphenyl)-ethyl]-[1,3]-dithian-2-yl}-propyl)-2,2-dimethyl-[1,3]-dioxin-4-one (5)

The aldehyde 1 used in this preparation has the following structure:

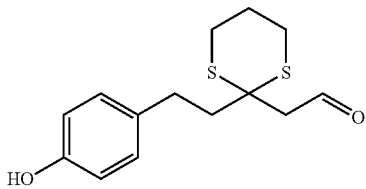

1

0.7 mL of a 1M solution of n-BuLi in hexane are added dropwise, under argon and at 0° C., to a solution of diisopropylamine (0.25 mL, 1.77 mmol) in 5 mL of anhydrous THF. After stirring for 20 min at 0° C., 2,2,6-trimethyl-1,3-dioxin-4-one (210 mg, 1.49 mmol) is added slowly at −78° C. to the reaction medium. After stirring for 45 min at this temperature, the aldehyde 1 (200 mg, 0.71 mmol) is added to the medium. After stirring for 40 min at −78° C., the reaction medium is left to return to ambient temperature, then the reaction is quenched by the addition of a saturated aqueous solution of NH$_4$Cl (up to a pH of approximately 7). After extraction with ether, the organic phases are dried over MgSO$_4$, filtered and concentrated under vacuum. Purification is carried out on silica gel (cyclohexane/AcOEt 6:4) in order to produce the expected compound (240 mg, 0.57 mmol, 80%) in the form of a white lacquer.

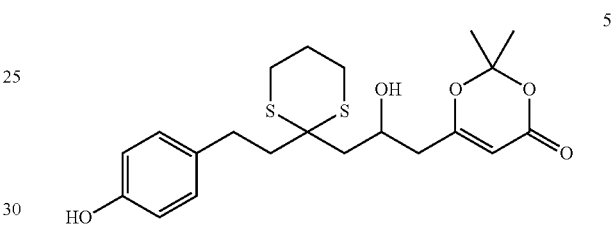

5

$C_{24}H_{28}O_5S_2$
M=424.6 g.mol$^{-1}$

NMR $^1$H (400 MHz, CDCl$_3$): δ=1.69 (s, 3H, —CH$_3$); 1.70 (s, 3H, —CH$_3$); 1.90-2.06 (m, 3H); 2.11-2.20 (m, 1H); 2.25-2.46 (m, 4H); 2.65-2.82 (m, 6H); 4.28-4.33 (m, 1H); 5.35 (s, 1H); 6.79 (d, J=8.4 Hz, 2H); 7.05 (d, J=8.4 Hz, 2H).
NMR $^{13}$C (100 MHz, CDCl$_3$): δ=24.7 (2C); 25.4; 26.1; 26.3; 29.7; 41.8; 42.1; 44.6; 51.7; 65.8; 95.3; 106.8; 115.5; 129.5; 133.1; 154.2; 161.4; 168.8.
Mass (ESI+): m/z (%) 463 [M+K]$^+$ (6), 447 [M+Na]$^+$ (56), 389 [M−C$_3$H$_6$O+Na]$^+$ (100).
HRMS (ESI+): m/z calculated for $C_{21}H_{28}O_5NaS_2$ 447.1276, found 447.1270.

Example 2

Preparation of propyl (5R)- and (5S)-5-Hydroxy-6-{2-[2-(4-hydroxyphenyl)-ethyl]-[1,3]dithian-2-yl}-3-oxohexanoate (6a)

Commercial 1-propanol (142 mg, 2.36 mmol) is added to a solution of phenolic derivative 5 (500 mg, 1.18 mmol) in 15 mL of anhydrous toluene. The reaction medium is taken to 110° C. for 9 h before of being concentrated under vacuum. Purification is carried out on silica gel (cyclohexane/AcOEt 6:4) in order to produce the racemic mixture of the expected β-ketoester (233 mg, 0.55 mmol, 46%) in the form of a colourless oil. This product is in fact a mixture of two compounds in equilibrium: the β-ketoester and its corresponding enolic form in a ratio of 91:9.

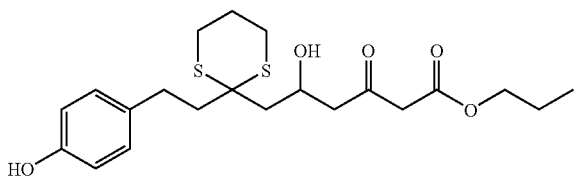

6a

C$_{21}$H$_{30}$O$_5$S$_2$
M=426.6 g.mol$^{-1}$

NMR $^1$H (400 MHz, CDCl$_3$): δ=0.94 (t, J=7.4 Hz, 3H); 1.61-1.72 (m, 2H); 1.86-2.05 (m, 3H); 2.13-2.30 (m, 2H); 2.34 (dd, J=15.2, 8.8 Hz, 1H); 2.65 (dd, J=16.8, 4.8 Hz, 1H); 2.69-2.98 (m, 7H); 3.51 (d, J=1.6 Hz, 2H); 4.10 (t, J=6.8 Hz, 2H); 4.46-4.54 (m, 1H); 6.75 (d, J=8.4 Hz, 2H); 7.04 (d, J=8.4 Hz, 2H).

NMR $^{13}$C (100 MHz, CDCl$_3$): δ=10.4; 21.9; 25.0; 26.1; 26.4; 29.6; 41.9; 43.9; 50.0; 50.3; 51.9; 65.2; 67.3; 115.5; 129.6; 133.3; 154.3; 167.5; 202.4.

Mass (ESI+): m/z (%) 449 [M+Na]$^+$ (25), 409 [M+H—H$_2$O]$^+$ (8).

HRMS (IE): m/z calculated for C$_{21}$H$_{30}$O$_5$S$_2$ 426.1535, found 426.1574.

Example 3

Preparation of propyl (3R,5S)- and (3S,5R)-3,5-Dihydroxy-6-{2-[2-(4hydroxyphenyl)-ethyl]-[1,3]-dithian-2-yl}-hexanoate (8a)

1.0 mL of a commercial 1M solution of BEt$_3$ in hexane then 1.0 mL of anhydrous MeOH are added, at ambient temperature and under argon, to a solution of the ketone 6a (200 mg, 0.47 mmol) in 2.6 mL of anhydrous THF. After stirring for 1 h at ambient temperature, the reaction medium is cooled down to −78° C. then NaBH$_4$ (37 mg, 0.98 mmol) is added in one go. After stirring for 2 h, the reaction medium is quenched at −78° C. by the addition of a methanol buffer (pH=7, AcONa/AcOH). After stiffing overnight at ambient temperature, the reaction medium is concentrated, taken up in a saturated aqueous solution of K$_2$CO$_3$ then extracted with AcOEt. The organic phases are then combined, dried over MgSO$_4$, filtered and concentrated under vacuum. The residue is then taken up in MeOH and stirred overnight at ambient temperature. After evaporation of the MeOH, purification is carried out on silica gel (cyclohexane/AcOEt 8:2) in order to produce the racemic mixture of the diol of syn configuration (135 mg, 0.31 mmol, 67%) in the form of a colourless oil.

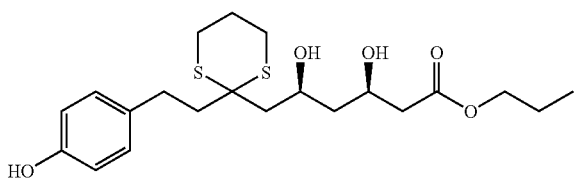

8a

C$_{24}$H$_{32}$O$_5$S$_2$
M=428.6 g.mol$^{-1}$

NMR $^1$H (400 MHz, CDCl$_3$): δ=0.93 (t, J=7.4 Hz, 3H); 1.47-1.54 (m, 1H); 1.60-1.77 (m, 3H); 1.87-2.06 (m, 3H); 2.10-2.20 (m, 1H); 2.21-2.30 (m, 1H); 2.35 (dd, J=15.4, 9.0 Hz, 1H); 2.48 (dd, J=16.0, 4.8 Hz, 1H); 2.55 (dd, J=16.0, 7.6 Hz, 1H); 2.61-2.70 (m, 1H); 2.73-3.00 (m, 5H); 4.06 (t, J=6.8 Hz, 2H); 4.24-4.36 (m, 2H); 6.76 (d, J=8.4 Hz, 2H); 7.03 (d, J=8.4 Hz, 2H).

NMR $^{13}$C (100 MHz, CDCl$_3$): δ=10.5; 22.0; 24.9; 26.1; 26.4; 29.8; 41.9; 42.0; 43.1; 45.0; 51.9; 66.6; 68.4; 69.1; 115.6; 129.6; 133.1; 154.5; 172.6.

Mass (ESI+): m/z (%) 451 [M+Na]$^+$ (100), 429 [M+H]$^+$ (1), 197 (20).

HRMS (IE): m/z calculated for C$_{21}$H$_{32}$O$_5$S$_2$ 428.1691, found 428.1713.

Example 4

Preparation of propyl (2S,4R,6R)- and (2R,4S,6S)-(4-Hydroxy-1'-oxo-1,7-dioxadispiro[5.1.5.2]pentadeca-9,12-dien-2-yl)-acetate (10a) and propyl (2S,4R,6S)- and (2R,4S,6R)-(4-Hydroxy-11-oxo-1,7-dioxadispiro[5.1.5.2]pentadeca-9,12-dien-2-yl)-acetate (11a)

PIFA (385 mg, 0.90 mmol) is added, in the dark and in one go, to a solution of syn diol 8a (120 mg, 0.28 mmol) in 10 mL of an acetone/water mixture (9:1). After stirring for 15 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (cyclohexane/AcOEt 5:5) in order to produce the expected products 10a (16 mg, 48 μmol, 17%) and 11a (20 mg, 59 μmol, 21%) in the form of colourless oils.

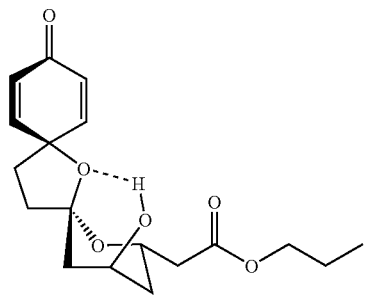

10a

C$_{18}$H$_{24}$O$_6$
M=336.4 g.mol$^{-1}$

NMR $^1$H (400 MHz, CDCl$_3$): δ=0.96 (t, J=7.4 Hz, 3H); 1.47-1.56 (m, 1H); 1.63-1.73 (m, 2H); 1.80-1.87 (m, 1H); 1.91-2.06 (m, 4H); 2.17-2.25 (m, 1H); 2.30-2.39 (m, 1H); 2.44-2.55 (m, 2H); 4.01-4.08 (m, 1H); 4.10-4.20 (m, 2H); 4.60-4.68 (m, 1H); 6.10 (dd, J=10.1, 2.0 Hz, 1H); 6.19 (dd, J=10.1, 2.0 Hz, 1H); 6.76 (dd, J=10.1, 3.0 Hz, 1H); 7.16 (dd, J=10.1, 3.0 Hz, 1H).

NMR $^{13}$C (100 MHz, CDCl$_3$): δ=10.6; 22.2; 34.2; 37.7; 38.8; 39.1; 41.0; 62.7; 64.7; 66.4; 80.3; 109.1; 127.3; 127.6; 148.7; 151.6; 171.4; 185.6.

Mass (ESI+): m/z (%) 359 [M+Na]$^+$ (100), 319 [M+H—H$_2$O]$^+$ (3), 107 (41).

HRMS (IE): m/z calculated for $C_{18}H_{24}O_6$ 336.1573, found 336.1565.

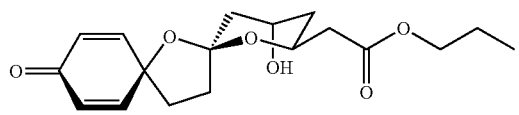

11a $C_{18}H_{24}O_6$
M=336.4 g.mol$^{-1}$
NMR $^1$H (400 MHz, CDCl$_3$): δ=0.96 (t, J=7.4 Hz, 3H); 1.58-1.72 (m, 4H); 1.87-2.11 (m, 4H); 2.26-2.36 (m, 1H); 2.48 (dd, J=15.5, 4.2 Hz, 1H); 2.64 (dd, J=15.5, 9.2 Hz, 1H); 2.72-2.79 (m, 1H); 4.01-4.13 (m, 2H); 4.37-4.48 (m, 2H); 6.11 (dd, J=10.2, 3.6 Hz, 1H); 6.11 (dd, J=10.2, 3.6 Hz, 1H); 6.77 (dd, J=10.2, 3.0 Hz, 1H); 6.91 (dd, J=10.2, 3.0 Hz, 1H).
NMR $^{13}$C (100 MHz, CDCl$_3$): δ=10.6; 22.2; 35.3; 35.7; 37.3; 40.4; 41.1; 64.9; 66.5; 66.9; 78.1; 108.9; 127.2; 127.4; 149.3; 152.2; 171.6; 185.9.
Mass (ESI+): m/z (%) 359 [M+Na]$^+$ (100), 319 [M+H—H$_2$O]$^+$ (3), 107 (39).
HRMS (IE): m/z calculated for $C_{18}H_{24}O_6$ 336.1573, found 336.1567.

Example 5

Preparation of decyl (5R)- and (5S)-5-Hydroxy-6-{2-[2-(4-hydroxyphenyl)-ethyl]-[1,3]-dithian-2-yl}-3-oxohexanoate (6b)

Commercial 1-decanol (373 mg, 2.36 mmol) is added to a solution of phenolic derivative 5 (500 mg, 1.18 mmol) in 17 mL of anhydrous toluene. The reaction medium is taken to 110° C. for 6 h before being concentrated under vacuum. Purification is carried out on silica gel (cyclohexane/AcOEt 8:2 to 7:3) in order to produce the racemic mixture of the β-ketoester (387 mg, 0.74 mmol, 63%) in the form of a colourless oil. This product is in fact a mixture of two compounds in equilibrium: the β-ketoester and its corresponding enolic form in a ratio of 93:7.

J=17.2, 4.6 Hz, 1H); 2.67-2.98 (m, 7H); 3.50 (d, J=1.6 Hz, 2H); 4.13 (t, J=6.8 Hz, 2H); 4.45-4.52 (m, 1H); 6.75 (d, J=8.0 Hz, 2H); 7.05 (d, J=8.0 Hz, 2H).
NMR $^{13}$C (100 MHz, CDCl$_3$): δ=14.1; 22.6; 24.9; 25.8; 26.0; 26.3; 28.4; 29.2-29.5; 31.8; 41.7; 43.8; 49.9; 50.2; 51.8; 65.1; 65.8; 115.4; 129.6; 133.3; 154.1; 167.4; 202.3.
Mass (FAB+, NBA): m/z (%) 547 [M+Na]$^+$ (25), 524 [M]$^+$ (63), 507 (82), 239 (100).
HRMS (ESI+): m/z calculated for $C_{28}H_{44}O_5NaS_2$ 547.2528, found 547.2522.

Example 6

Preparation of decyl (3S,5R)- and (3R,5S)-3,5-Dihydroxy-6-{2-[2-(4-hydroxyphenyl)-ethyl]-[1,3]-dithian-2-yl}-hexanoate (8b)

1.44 mL of a commercial 1M solution of BEt$_3$ in hexane then 1.7 mL of anhydrous MeOH are added, at ambient temperature and under argon, to a solution of the ketone 6b (360 mg, 0.69 mmol) in 4.0 mL of anhydrous THF. After stirring for 1 h at ambient temperature, the reaction medium is cooled down to −78° C. then NaBH$_4$ (54 mg, 1.44 mmol) is added in one go. After stirring for 2 h, the reaction medium is quenched at −78° C. by the addition of a methanol buffer (pH=7, AcONa/AcOH). After stirring overnight at ambient temperature, the reaction medium is concentrated, taken up in a saturated aqueous solution of K$_2$CO$_3$ then extracted with AcOEt. The organic phases are then combined, dried over MgSO$_4$, filtered and concentrated under vacuum. The residue is then taken up in MeOH and stirred for 3 h at ambient temperature.

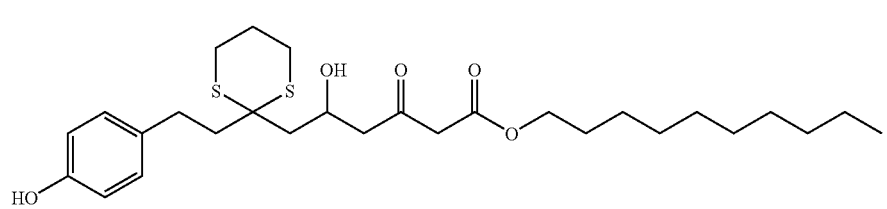

6b $C_{28}H_{44}O_5S_2$
M=524.8 g.mol$^{-1}$
NMR $^1$H (400 MHz, CDCl$_3$): δ=0.88 (t, J=6.6 Hz, 3H); 1.20-1.38 (m, 14H); 1.59-1.68 (m, 2H); 1.87-2.06 (m, 3H); 2.13-2.28 (m, 2H); 2.34 (dd, J=15.2, 8.8 Hz, 1H); 2.62 (dd, After evaporation of the MeOH, purification is carried out on silica gel (cyclohexane/AcOEt 8:2 to 7:3) in order to produce the racemic mixture of the diol of syn configuration (311 mg, 0.59 mmol, 86%) in the form of a colourless oil.

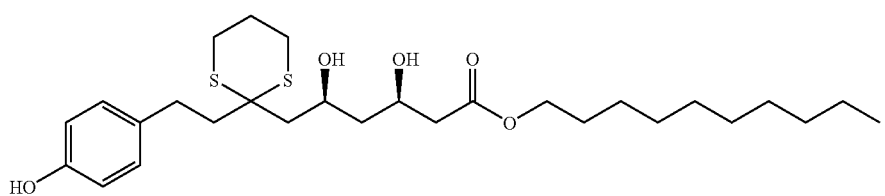

8b $C_{28}H_{46}O_5S_2$
$M=526.8$ g.mol$^{-1}$

NMR $^1$H (400 MHz, CDCl$_3$): δ=0.88 (t, J=6.8 Hz, 3H); 1.23-1.35 (m, 14H); 1.49 (ddd, J=14.4, 3.4, 2.8 Hz, 1H); 1.57-1.66 (m, 2H); 1.71 (ddd, J=14.4, 9.6, 9.6 Hz, 1H); 1.89-2.06 (m, 3H); 2.11-2.31 (m, 2H); 2.36 (dd, J=15.2, 9.2 Hz, 1H); 2.46 (dd, J=16.0, 4.8 Hz, 1H); 2.53 (dd, J=16.0, 8.0 Hz, 1H); 2.62-2.71 (m, 1H); 2.73-3.00 (m, 5H); 4.09 (t, J=6.6 Hz, 2H); 4.24-4.34 (m, 2H); 6.76 (d, J=8.4 Hz, 2H); 7.04 (d, J=8.4 Hz, 2H).

NMR $^{13}$C (100 MHz, CDCl$_3$): δ=14.1; 22.6; 24.8; 25.8; 26.0; 26.3; 28.5; 29.2-29.7; 31.8; 41.8; 41.9; 43.0; 44.9; 51.8; 65.0; 68.2; 68.9; 115.5; 129.5; 133.1; 154.3; 172.5.

Mass (FAB+, NBA): m/z (%) 549 [M+Na]$^+$ (46), 526 [M]$^+$ (50), 255 (100), 239 (94).
HRMS (ESI+): m/z calculated for $C_{28}H_{46}O_5S_2K$ 565.2424, found 565.2421.

Example 7

Preparation of decyl (2S,4R,6R)- and (2R,4S,6S)-(4-Hydroxy-11-oxo-1,7-dioxadispiro[5.1.5.2]pentadeca-9,12-dien-2-yl)-acetate (10b) and (2S,4R,6S)- and decyl (2R,4S,6R)-(4-Hydroxy-11-oxo-1,7-dioxadispiro[5.1.5.2]pentadeca-9,12-dien-2-yl)-acetate (11b)

PIFA (630 mg, 1.46 mmol) is added, in the dark and in one go, to a solution of the syn diol 8b (265 mg, 0.50 mmol) in 27.8 mL of an acetone/water mixture (9:1). After stirring for 15 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (cyclohexane/AcOEt 6:4) in order to produce the expected products 10b (38 mg, 87 μmol, 17%) and 11b (32 mg, 74 μmol, 15%) in the form of colourless oils.

10b

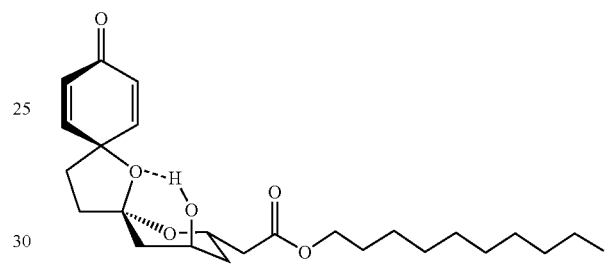

$C_{25}H_{38}O_6$
$M=434.6$ g.mol$^{-1}$

NMR $^1$H (400 MHz, CDCl$_3$): δ=0.88 (t, J=7.0 Hz, 3H); 1.20-1.38 (m, 14H); 1.47-1.56 (m, 1H); 1.60-1.70 (m, 2H); 1.79-1.87 (m, 1H); 1.91-2.06 (m, 4H); 2.16-2.24 (m, 1H); 2.29-2.39 (m, 1H); 2.43-2.55 (m, 2H); 4.03-4.11 (m, 1H); 4.12-4.20 (m, 2H); 4.58-4.68 (m, 1H); 6.10 (dd, J=10.0, 2.0 Hz, 1H); 6.19 (dd, J=10.0, 2.0 Hz, 1H); 6.76 (dd, J=10.0, 3.2 Hz, 1H); 7.16 (dd, J=10.0, 3.2 Hz, 1H).
NMR $^{13}$C (100 MHz, CDCl$_3$): δ=14.1; 22.6; 25.9; 28.6; 29.3-29.5; 31.8; 34.0; 37.4; 38.6; 38.8; 40.8; 62.5; 64.5; 64.8; 80.0; 108.9; 127.0; 127.4; 148.4; 151.4; 171.2; 185.4.
Mass (ESI+): m/z (%) 457 [M+Na]$^+$ (100), 399 (12), 107 (11).
HRMS (ESI+): m/z calculated for $C_{25}H_{38}O_6Na$ 457.2566, found 457.2564.

11b

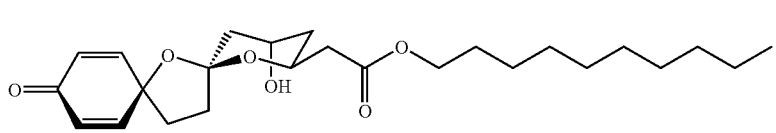

$C_{25}H_{38}O_6$ $M=434.6$ g.mol$^{-1}$

NMR $^1$H (400 MHz, CDCl$_3$): δ=0.88 (t, J=6.8 Hz, 3H); 1.23-1.37 (m, 14H); 1.58-1.75 (m, 4H); 1.87-2.11 (m, 4H); 2.29 (ddd, J=12.0, 7.8, 4.4 Hz, 1H); 2.47 (dd, J=15.2, 4.2 Hz, 1H); 2.64 (dd, J=15.2, 9.2 Hz, 1H); 2.75 (ddd, J=13.0, 7.3, 1.6 Hz, 1H); 4.08 (t, J=12.0 Hz, 1H); 4.10 (t, J=12.0 Hz, 1H); 4.37-4.47 (m, 2H); 6.10 (dd, J=10.4, 3.5 Hz, 1H); 6.11 (dd, J=10.4, 3.5 Hz, 1H); 6.76 (dd, J=10.4, 2.9 Hz, 1H); 6.91 (dd, J=10.4, 2.9 Hz, 1H).

NMR $^{13}$C (100 MHz, CDCl$_3$): δ=14.3; 22.9; 25.2; 26.2; 28.9; 29.5-29.9; 32.1; 35.3; 35.7; 37.3; 40.4; 41.1; 64.9; 65.1; 66.9; 78.1; 108.8; 127.3; 127.4; 149.2; 152.2; 171.6; 185.8.

Mass (ESI+): m/z (%) 457 [M+Na]$^+$ (100), 399 (8), 107 (14).

HRMS (ESI+): m/z calculated for $C_{25}H_{38}O_6Na$ 457.2566, found 457.2561.

Example 8

Preparation of decyl (3S,5S)- and (3R,5R)-3,5-Dihydroxy-6-{2-[2-(4-hydroxyphenyl)-ethyl]-[1,3]-dithian-2-yl}-hexanoate (9b)

A solution of the ketone 6b (375 mg, 0.72 mmol) in 6 mL of a MeCN/CH$_2$Cl$_2$ mixture (2:1) is added dropwise, at 0° C., to a suspension of Me$_4$NBH(OAc)$_3$ (752 mg, 2.86 mmol) in 10 mL of a MeCN/AcOH mixture (4:1). After stirring for 3 h at 0° C., the reaction medium is diluted in AcOEt then poured into 20 mL of a saturated aqueous solution of mixed sodium and potassium tartrate. After filtration of the precipitate formed through cotton, the phases are separated and the aqueous phase is extracted again with AcOEt. The organic phases are then combined, dried over MgSO$_4$, filtered and concentrated under vacuum. Purification is carried out on a silica column (cyclohexane/AcOEt 8:2 to 7:3) in order to produce the racemic mixture of the diol of anti configuration (297 mg, 0.56 mmol, 79%) in the form of a colourless oil.
syn/anti mixture 2:8.

Example 9

Preparation of decyl (2S,4S,6R)- and (2R,4R,6S)-(4-Hydroxy-11-oxo-1,7-dioxadispiro[5.1.5.2]pentadeca-9,12-dien-2-yl)-acetate (12b) and (2S,4S,6S)- and decyl (2R,4R,6R)-(4-Hydroxy-11-oxo-1,7-dioxadispiro[5.1.5.2]pentadeca-9,12-dien-2-yl)-acetate (13b)

PIFA (705 mg, 1.64 mmol) is added, in one go, to a solution of the anti diol 9b (270 mg, 0.51 mmol) in 10 mL of an acetone/water mixture (9:1). After stirring for 10 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (cyclohexane/AcOEt 7:3 to 5:5) in order to produce the expected products 12b (36 mg, 84 μmol, 16%) and 13b (38 mg, 88 μmol, 17%) in the form of colourless oils.

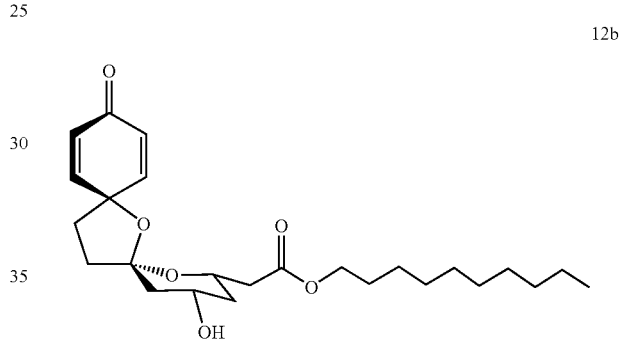

12b

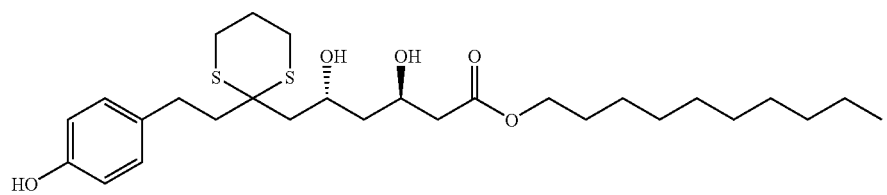

9b $C_{28}H_{46}O_5S_2$ $M=526.8$ g.mol$^{-1}$

NMR $^1$H (400 MHz, CDCl$_3$): δ=0.88 (t, J=6.6 Hz, 3H); 1.23-1.35 (m, 14H); 1.57-1.70 (m, 4H); 1.87-2.07 (m, 3H); 2.09-2.19 (m, 1H); 2.20-2.30 (m, 1H); 2.32-2.47 (dd, J=15.8, 9.3 Hz, 1H); 2.51-2.56 (m, 2H); 2.60-2.70 (m, 1H); 2.73-2.86 (m, 3H); 2.88-3.02 (m, 2H); 4.10 (t, J=6.8 Hz, 2H); 4.33-4.42 (m, 2H); 6.74 (d, J=7.8 Hz, 2H); 7.02 (d, J=7.8 Hz, 2H).

NMR $^{13}$C (100 MHz, CDCl$_3$): δ=14.3; 22.8; 25.0; 26.0; 26.2; 26.5; 28.7; 29.4-29.9; 32.0; 41.7; 42.2; 43.3; 44.9; 52.1; 65.2; 65.7; 66.2; 115.6; 129.7; 133.3; 154.4; 173.0.

Mass (ESI+): m/z (%) 565 [M+K]$^+$ (8), 549 [M+Na]$^+$ (100).

HRMS (ESI+): m/z calculated for $C_{28}H_{46}O_5NaS_2$ 549.2684, found 549.2683.

$C_{25}H_{38}O_6$ $M=434.6$ g.mol$^{-1}$

NMR $^1$H (400 MHz, CDCl$_3$): δ=0.88 (t, J=6.6 Hz, 3H); 1.20-1.39 (m, 15H); 1.58-1.70 (m, 3H); 1.94-2.12 (m, 4H); 2.18-2.25 (m, 1H); 2.30-2.37 (m, 1H); 2.44-2.57 (m, 2H); 4.02-4.10 (m, 1H); 4.12-4.21 (m, 2H); 4.28-4.36 (m, 1H); 6.10 (dd, J=10.0, 1.0 Hz, 1H); 6.16 (dd, J=10.0, 1.0 Hz, 1H); 6.77 (dd, J=10.0, 3.0 Hz, 1H); 7.08 (dd, J=10.0, 3.0 Hz, 1H).

NMR $^{13}$C (100 MHz, CDCl$_3$): δ=14.3; 22.9; 26.1; 28.8; 29.5-29.7; 32.1; 34.7; 38.8; 40.2; 41.1; 42.7; 65.1; 66.0; 79.4; 109.0; 127.1; 127.4; 149.3; 152.2; 171.4; 185.8.

Mass (ESI+): m/z (%) 473 [M+K]$^+$ (8), 457 [M+Na]$^+$ (100).

HRMS (ESI+): m/z calculated for $C_{25}H_{38}O_6Na$ 457.2566, found 457.2559.

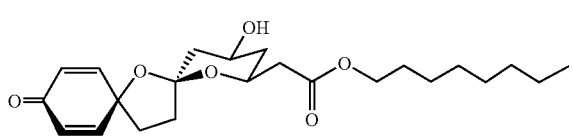

13b

C<sub>25</sub>H<sub>38</sub>O<sub>6</sub>
M=434.6 g.mol$^{-1}$

NMR $^1$H (400 MHz, CDCl$_3$): δ=0.88 (t, J=6.8 Hz, 3H); 1.23-1.38 (m, 15H); 1.59-1.70 (m, 2H); 1.77-1.90 (m, 2H); 1.98-2.10 (m, 2H); 2.14 (ddd, J=12.4, 4.4 Hz, 1.2 Hz, 1H); 2.24-2.34 (m, 1H); 2.45-2.54 (m, 2H); 2.67 (dd, J=15.6, 8.8 Hz, 1H); 3.87-3.96 (m, 2H); 4.04-4.15 (m, 2H); 6.11 (dd, J=9.4, 2.0 Hz, 1H); 6.13 (dd, J=10.4, 2.0 Hz, 1H); 6.77 (dd, J=9.4, 2.9 Hz, 1H); 6.90 (dd, J=10.4, 2.9 Hz, 1H).

NMR $^{13}$C (100 MHz, CDCl$_3$): δ=14.3; 22.9; 26.1; 28.9; 29.5-29.7; 32.1; 33.6; 35.0; 40.0; 41.0; 43.3; 65.2; 66.7; 68.5; 78.5; 109.4; 127.4; 127.7; 148.8; 151.5; 171.4; 185.7.

Mass (ESI+): m/z (%) 473 [M+K]$^+$ (7), 457 [M+Na]$^+$ (100).

HRMS (ESI+): m/z calculated for C$_{25}$H$_{38}$O$_6$Na 457.2566, found 457.2565.

Example 10

Preparation of decyl (2S,4S,6S)- and (2R,4R,6R)-(4-Acetoxy-11-oxo-1,7-dioxadispiro[5.1.5.2]pentadeca-9,12-dien-2-yl)-acetate (14b)

DMAP (5.1 mg, 0.04 mmol) and acetic anhydride (4.2 mg, 0.04 mmol) are added, at ambient temperature and under argon, to a solution of alcohol 13b (15.0 mg, 0.03 mmol) in 1 mL of CH$_2$Cl$_2$. After stirring overnight at ambient temperature, the reaction medium is quenched by the addition of a 1N aqueous solution of HCl before being extracted with CH$_2$Cl$_2$. The organic phases are combined, dried over MgSO$_4$ and concentrated under vacuum. Purification is carried out on silica gel (cyclohexane/AcOEt 8:2) in order to produce the expected product (9.8 mg, 0.02 mmol, 61%) in the form of a colourless oil.

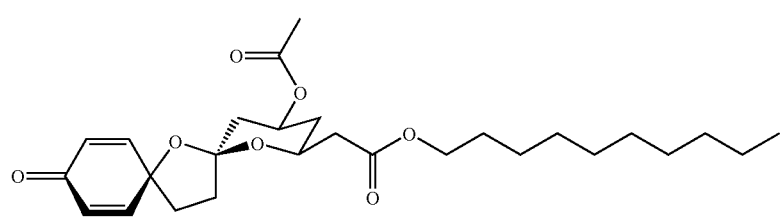

14b

C<sub>27</sub>H<sub>40</sub>O<sub>7</sub>
M=476.

NMR $^1$H (400 MHz, CDCl$_3$): δ=0.88 (t, J=6.8 Hz, 3H); 1.23-1.45 (m, 15H); 1.59-1.67 (m, 2H); 1.84-1.96 (m, 2H); 2.00-2.11 (m, 5H); 2.15 (ddd, J=12.4, 4.4 Hz, 1.2 Hz, 1H); 2.25-2.34 (m, 1H); 2.46-2.58 (m, 2H); 2.65 (dd, J=16.0, 9.0 Hz, 1H); 3.93-4.01 (m, 1H); 4.04-4.15 (m, 2H); 4.90-4.99 (m, 1H); 6.11 (dd, J=10.4, 2.0 Hz, 1H); 6.13 (dd, J=10.0, 2.0 Hz, 1H); 6.74 (dd, J=10.4, 3.0 Hz, 1H); 6.89 (dd, J=10.0, 3.0 Hz, 1H).

NMR $^{13}$C (100 MHz, CDCl$_3$): δ=14.3; 21.4; 22.9; 26.1; 28.9; 29.5-29.7; 32.1; 33.5; 35.0; 36.2; 39.7; 40.9; 65.2; 68.3; 68.6; 78.7; 109.1; 127.5; 127.8; 148.6; 151.2; 170.6; 171.0; 185.5.

HRMS (ESI+): m/z calculated for C$_{27}$H$_{40}$O$_7$Na 499.2672, found 499.2670.

Example 11

Preparation of 2-decyloxycarbonylmethyl-11-oxo-1,7-dioxadispiro[5.1.5.2]pentadeca-9,12-dien-4-yl heptanoate (15b)

DMAP (4.2 mg, 0.03 mmol), heptanoyl chloride (6.2 mg, 0.04 mmol) then triethylamine (4.2 mg, 0.04 mmol) are added, at 0° C. and under argon, to a solution of the alcohol 12b (14.8 mg, 0.03 mmol) in 1 mL of anhydrous CH$_2$Cl$_2$. After stirring for 0.5 h at 0° C. and 4 h at ambient temperature, the reaction medium is quenched by the addition of a 1N aqueous solution of HCl. After extraction with CH$_2$Cl$_2$, the organic phases are combined, dried over MgSO$_4$, filtered and concentrated under vacuum. Purification is carried out on silica gel (cyclohexane/AcOEt 85:15) in order to produce the expected ester (14.0 mg, 0.03 mmol, 75%) in the form of a colourless oil.

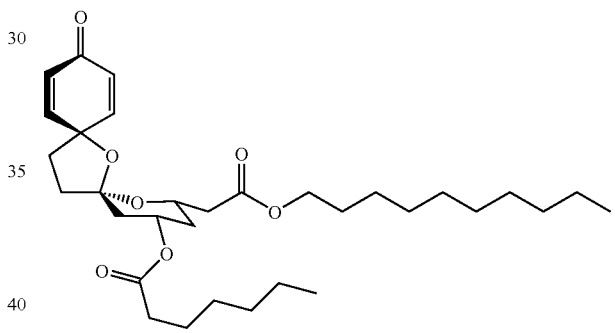

15b

C<sub>32</sub>H<sub>50</sub>O<sub>7</sub>
M=546.7 g.mol$^{-1}$

NMR $^1$H (400 MHz, CDCl$_3$): δ=0.88 (m, 6H); 1.23-1.38 (m, 21H); 1.55-1.70 (m, 5H); 1.94-2.16 (m, 4H); 2.17-2.39 (m, 4H); 2.43-2.56 (m, 2H); 4.02-4.10 (m, 1H); 4.12-4.19 (m, 2H); 4.36-4.44 (m, 1H); 5.15-5.25 (m, 1H); 6.09 (dd, J=10.0, 2.0 Hz, 1H); 6.16 (dd, J=10.0, 2.0 Hz, 1H); 6.76 (dd, J=10.0, 3.0 Hz, 1H); 7.08 (dd, J=10.0, 3.0 Hz, 1H).

NMR $^{13}$C (100 MHz, CDCl$_3$): δ=14.2; 14.3; 22.7; 22.9; 25.1; 26.1; 28.9; 29.0; 29.5-29.7; 31.6; 32.1; 34.7; 36.6; 38.8; 39.2; 41.0; 65.1; 65.7; 67.6; 79.6; 108.8; 127.1; 127.5; 149.2; 152.0; 171.4; 173.2; 185.8.

Mass (ESI+): m/z (%) 585 [M+K]$^+$ (7), 569 [M+Na]$^+$ (100).

HRMS (ESI+): m/z calculated for $C_{32}H_{50}O_7Na$ 569.3454, found 569.3449.

Example 12

Preparation of decyl (5R)- and (5S)-5-Hydroxy-6-{2-[2-(4-hydroxy-3,5-dimethoxyphenyl)-ethyl]-[1,3]-dithian-2-yl}-3-oxohexanoate (6'b)

1) Preparation of the Starting Compound 5'

4-Benzyloxy-3,5-dimethoxybenzaldehyde (5'-1)

A solution of commercial aldehyde (6.0 g, 32.9 mmol) and benzyl bromide (5.9 mL, 49.4 mmol) in 70 mL of THF is added, in several fractions, to a solution of KOH (3.69 g, 65.8 mmol) in 40 mL of water. A catalytic quantity of $Bu_4NHSO_4$ (0.56 g, 1.6 mmol) is then added then the reaction medium is stirred overnight at ambient temperature. After extraction with $CH_2Cl_2$, the organic phases are combined, dried over $MgSO_4$, filtered then concentrated under vacuum. Purification is carried out on a silica column (cyclohexane/EtOAc 85:15) in order to produce the aldehyde 5'-1 (8.43 g, 31.0 mmol, 94%) in the form of a white solid.

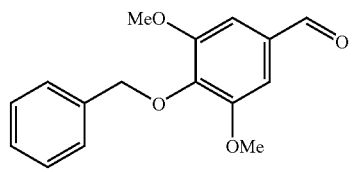

5'-1

$C_{16}H_{16}O_4$
M=272.3 g.mol$^{-1}$

Analyses: in accordance with the literature (Bennett C. J., Caldwell S. T., McPhail D. B., Morrice P. C., Duthie G. G., Hartley R. C., *Bioorg. & Med. Chem.* 2004, 12, 2079-2098)

ethyl 3-oxo-4-(triphenylphosphoranylidene)butanoate (5'-2)

triphenylphosphine (30.0 g, 114.3 mmol) is added, at ambient temperature, to a solution of commercial ethyl 4-chloro-3-oxobutanoate (18.81 g, 114.3 mmol) in 200 mL of anhydrous THF. The reaction medium is taken to reflux for 18 h before being concentrated under vacuum. The oil obtained is taken up in distilled water then washed with ether. The aqueous phase is then basified by a saturated aqueous solution of $NaHCO_3$ (up to pH 8). After extraction with AcOEt, the organic phases are combined, dried over $MgSO_4$, filtered then concentrated under vacuum. Purification is carried out by recrystallization from ether in order to produce, after filtration and drying, compound 5'-2 (14.96 g, 38.0 mmol, 34%) in the form of a slightly yellow solid.

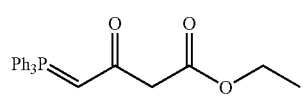

5'-2

$C_{24}H_{23}O_3P$
M=390.4 g.mol$^{-1}$

Analyses: in accordance with the literature (Sun K. M., Dawe R. D., *Carbohydrate Research* 1987, 171, 35-47).

ethyl 5-(4-Benzyloxy-3,5-dimethoxyphenyl)-3-oxo-pentanoate (5'-3)

NaH (1.32 g, 33.0 mmol, 60% in oil) is added, under argon and at ambient temperature, to a solution of phosphoranylidene 5'-2 (6.09 g, 15.61 mmol) in 25 mL of DMPU and 30 mL of anhydrous THF. After stirring for 20 min at ambient temperature, the aldehyde 5'-1 (2.50 g, 9.18 mmol) in solution in 10 mL of THF is added slowly to the reaction medium. After stirring for 50 min at ambient temperature, the reaction medium is taken to 40° C. for 1.5 h. After stirring overnight at ambient temperature, the reaction medium is quenched by the addition of a saturated aqueous solution of $NH_4Cl$. After extraction with $Et_2O$, the organic phases are dried over $MgSO_4$, filtered and concentrated under vacuum. Purification is carried out on silica gel (cyclohexane/AcOEt 9:1) in order to produce compound 5'-3 (2.33 g, 6.06 mmol, 66%) in the form of an slightly yellow oil. It is in fact a mixture of Z and E isomers in equilibrium with the corresponding enolic forms.

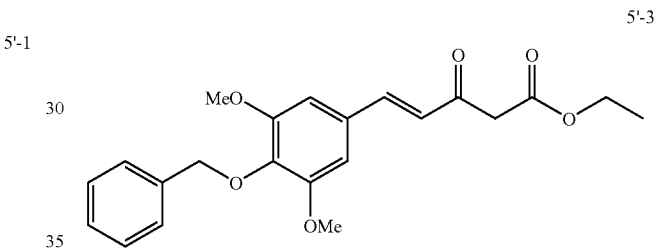

5'-3

$C_{22}H_{24}O_6$
M=384.4 g.mol$^{-1}$

Mass (FAB+, NBA): m/z (%) 385 [M+H]$^+$ (46), 293 (100).

5-(4-Hydroxy-3,5-dimethoxyphenyl)-3-ethyl oxo-pentanoate (5'-4)

80 mg of 5% Pd/C is added, at ambient temperature, to a solution of compound 5'-3 (578 mg, 1.50 mmol) in 12 mL of AcOEt. The reaction medium is stirred overnight under an $H_2$ atmosphere then it is filtered on Celite®, washed with AcOEt. The filtrate is then concentrated under vacuum in order to provide the expected product 5'-4 (423 mg, 1.42 mmol, 95%) in the form of a colourless oil. The crude product is used in the following stage without other purification.

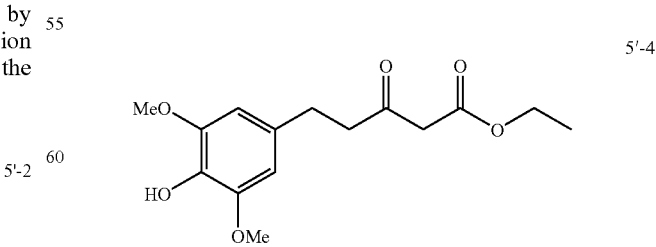

5'-4

$C_{15}H_{20}O_6$
M=296.3 g.mol$^{-1}$

NMR $^1$H (400 MHz, CDCl$_3$): δ=1.25 (t, J=7.1 Hz, 3H); 2.81-2.86 (m, 4H); 3.43 (s, 2H); 3.84 (s, 6H); 4.18 (q, J=7.1 Hz, 2H); 6.41 (s, 2H).

NMR $^{13}$C (100 MHz, CDCl$_3$): δ=14.0; 29.5; 44.7; 49.3; 56.1; 61.2; 104.9; 131.5; 133.0; 147.0; 167.1; 202.1.

HRMS (IE): m/z calculated for C$_{15}$H$_{20}$O$_6$ 296.1260, found 296.1253.

{2-[2-(4-Hydroxy-3,5-dimethoxyphenyl)-ethyl]-[1,3]-dithian-2-yl}-ethyl acetate (5'-5)

0.26 mL of BF$_3$.OEt$_2$ is added, dropwise, under argon and at ambient temperature, to a solution of the β-ketoester 5'-4 (550 mg, 1.9 mmol) and 1,3-propanedithiol (0.19 mL, 1.9 mmol) in 3 mL of anhydrous CH$_2$Cl$_2$. After stirring overnight, the reaction medium is quenched by the addition of 3 mL of a 1N aqueous solution of NaOH. After extraction with CH$_2$Cl$_2$, the organic phases are dried over MgSO$_4$, filtered and concentrated under vacuum. Purification is carried out on silica gel (cyclohexane/AcOEt 7:3) in order to produce compound 5'-5 (576 mg, 1.5 mol, 80%) in the form of a white lacquer.

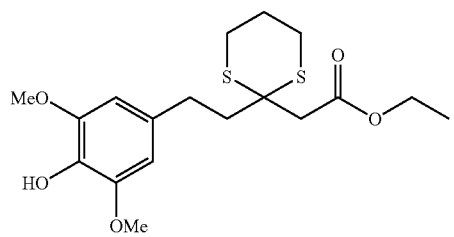

5'-5

C$_{18}$H$_{26}$O$_5$S$_2$
M=386.5 g.mol$^{-1}$

NMR $^1$H (400 MHz, CDCl$_3$): δ=1.29 (t, J=7.0 Hz, 3H); 1.85-1.98 (m, 1H); 2.08-2.16 (m, 1H); 2.32-2.39 (m, 2H); 2.74-2.86 (m, 4H); 3.06 (ddd, J=14.8, 10.8, 2.8 Hz, 2H); 3.11 (s, 2H); 3.88 (s, 6H); 4.18 (q, J=7.0 Hz, 2H); 6.46 (s, 2H).

NMR $^{13}$C (100 MHz, CDCl$_3$): δ=14.4; 25.1; 26.6; 30.7; 41.9; 42.9; 50.2; 56.4; 60.8; 105.3; 132.8; 133.1; 147.1; 169.9.

Mass (ESI+): m/z (%) 425 [M+K]$^+$ (21), 409 [M+Na]$^+$ (100).

HRMS (ESI+): m/z calculated for C$_{18}$H$_{26}$O$_5$NaS$_2$ 409.1119, found 409.1112.

{2-[2-(4-Hydroxy-3,5-dimethoxyphenyl)-ethyl]-[1,3]-dithian-2-yl}-acethaldehyde (1')

4.6 mL of a commercial 1.7M solution of DIBAL-H in toluene is added, dropwise, under argon and at −78° C., to a solution of the ester 5'-5 (1.42 g, 3.7 mmol) in 35 mL of anhydrous toluene. After stirring for 15 min at this temperature, the reaction medium is quenched by the addition of 5 mL of MeOH. After returning to ambient temperature (1 h), a 1N aqueous solution of NaOH is added. After extraction with AcOEt, the organic phases are dried over MgSO$_4$, filtered and concentrated under vacuum. Purification is carried out on silica gel (cyclohexane/AcOEt 8:2) in order to produce the aldehyde 1' (853 mg, 2.5 mmol, 68%) in the form of a yellow oil.

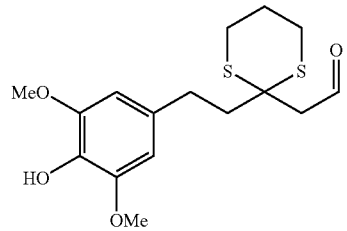

1'

C$_{16}$H$_{22}$O$_4$S$_2$
M=342.5 g.mol$^{-1}$

NMR $^1$H (400 MHz, CDCl$_3$): δ=1.91-2.08 (m, 2H); 2.25-2.30 (m, 2H); 2.74-2.78 (m, 2H); 2.83-2.94 (m, 4H); 2.96 (d, J=2.8 Hz, 2H); 3.87 (s, 6H); 6.40 (s, 2H); 9.82 (t, J=2.8 Hz, 1H).

NMR $^{13}$C (100 MHz, CDCl$_3$): δ=24.6; 26.2; 30.8; 42.5; 49.1; 50.2; 56.3; 105.0; 132.1; 133.1; 147.1; 199.7.

Mass (ESI+): m/z (%) 397 [M+MeOH+Na]$^+$ (100), 365 [M+Na]$^+$ (34).

6-(2-Hydroxy-3-{2-[2-(4-hydroxy-3,5-dimethoxyphenyl)-ethyl]-[1,3]-dithian-2-yl}-propyl)-2,2-dimethyl-[1,3]-dioxin-4-one (5')

2.5 mL of a 2.5M solution of n-BuLi in hexane is added dropwise, under argon and at 0° C., to a solution of diisopropylamine (0.87 mL, 6.23 mmol) in 18 mL of anhydrous THF. After stirring for 20 min at 0° C., 2,2,6-trimethyl-1,3-dioxin-4-one (744 mg, 5.23 mmol) is added slowly at −78° C. to the reaction medium. After stirring for 45 min at this temperature, the aldehyde 1' (853 mg, 2.49 mmol) is added to the medium. After stirring for 40 min at −78° C., the reaction medium is left to return to ambient temperature, then the reaction is quenched by the addition of a saturated aqueous solution of NH$_4$Cl (up to a pH of approximately 7). After extraction with AcOEt, the organic phases are dried over MgSO$_4$, filtered and concentrated under vacuum. Purification is carried out on silica gel (cyclohexane/AcOEt 6:4) in order to produce compound 5' (384 mg, 0.79 mmol, 32% non-optimized) in the form of a slightly yellow lacquer.

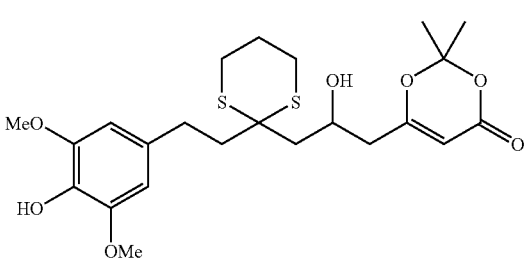

5'

$C_{23}H_{32}O_7S_2$
M=484.6 g.mol$^{-1}$

NMR $^1$H (400 MHz, CDCl$_3$): δ=1.68 (s, 3H); 1.69 (s, 3H); 1.90-2.07 (m, 3H); 2.12-2.22 (m, 1H); 2.25-2.40 (m, 3H); 2.45 (dd, J=14.4, 8.0 Hz, 1H); 2.65-3.02 (m, 6H); 3.87 (s, 6H); 4.29-4.36 (m, 1H); 5.36 (s, 1H); 6.42 (s, 2H).

NMR $^{13}$C (100 MHz, CDCl$_3$): δ=24.6; 24.7; 25.4; 26.1; 26.3; 30.8; 41.9; 42.0; 44.6; 51.7; 56.3; 65.7; 95.2; 105.1; 106.6; 132.4; 133.0; 147.1; 161.1; 168.7.

2) Preparation of the Starting Compound 6'b

Commercial 1-decanol (363 mg, 2.29 mmol) is added to a solution of the phenolic derivative 5' 370 mg, 0.76 mmol) in 14 mL of anhydrous toluene. The reaction medium is taken to 110° C. for 6 h before being concentrated under vacuum. Purification is carried out on silica gel (cyclohexane/AcOEt 8:2 to 7:3) in order to produce the racemic mixture of the β-ketoester (273 mg, 0.47 mmol, 61%) in the form of a colourless oil. This product is in fact a mixture of two compounds in equilibrium: the β-ketoester and its corresponding enolic form in a ratio of 94:6.

Example 13

Preparation of the decyl (3S,5R)- and (3R,5S)-3,5-Dihydroxy-6-{2-[2-(4-hydroxy-3,5-dimethoxyphenyl)-ethyl]-[1,3]-dithian-2-yl}-hexanoate (8'b)

0.99 mL of a commercial 1M solution of BEt$_3$ in hexane then 1 mL of anhydrous MeOH are added, at ambient temperature and under argon, to a solution of the ketone 6'b (260 mg, 0.44 mmol) in 2.6 mL of anhydrous THF. After stirring for 1 h at ambient temperature, the reaction medium is cooled down to −78° C. then NaBH$_4$ (35 mg, 0.93 mmol) is added in one go. After stirring for 2 h, the reaction medium is quenched at −78° C. by the addition of a methanol buffer (pH=7, AcONa/AcOH). After stirring overnight at ambient temperature, the reaction medium is concentrated, taken up in a saturated aqueous solution of K$_2$CO$_3$ then extracted with AcOEt. The organic phases are then combined, dried over MgSO$_4$, filtered and concentrated under vacuum. The residue is then taken up in MeOH and stirred for 3 h at ambient temperature.

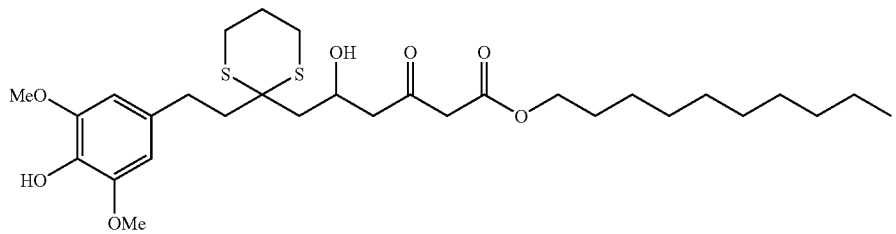

6'b $C_{30}H_{48}O_7S_2$
M=584.8 g.mol$^{-1}$

NMR $^1$H (400 MHz, CDCl$_3$): δ=0.88 (t, J=6.6 Hz, 3H); 1.22-1.38 (m, 14H); 1.59-1.68 (m, 2H); 1.87-2.09 (m, 3H); 2.15-2.30 (m, 2H); 2.36 (dd, J=15.6, 9.2 Hz, 1H); 2.67-3.03 (m, 8H); 3.51 (s, 2H); 3.87 (s, 6H); 4.12 (t, J=6.8 Hz, 2H); 4.47-4.54 (m, 1H); 6.45 (s, 2H).

NMR $^{13}$C (100 MHz, CDCl$_3$): δ=14.2; 22.8; 25.0; 26.0; 26.2; 26.4; 28.6; 29.3-29.6; 32.0; 42.0; 43.9; 50.1; 50.4; 51.8; 56.4; 65.1; 65.8; 105.2; 132.8; 133.0; 147.1; 167.2; 202.3.

Mass (ESI+): m/z (%) 623 [M+K]$^+$ (6), 607 [M+Na]$^+$ (100).

HRMS (ESI+): m/z calculated for $C_{30}H_{48}O_7NaS_2$ 607.2739, found 607.2737.

After evaporation of the MeOH, purification is carried out on silica gel (cyclohexane/AcOEt 6:4) in order to produce the racemic mixture of the diol of syn configuration (227 mg, 0.39 mmol, 87%) in the form of a colourless oil.

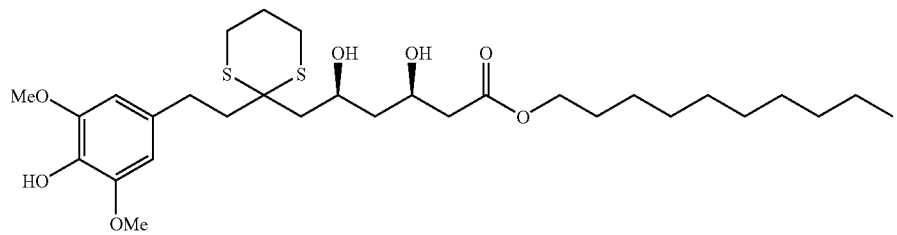

8'b $C_{30}H_{50}O_5S_2$
M=586.8 g.mol$^{-1}$

NMR $^1$H (400 MHz, CDCl$_3$): δ=0.88 (t, J=7.2 Hz, 3H); 1.23-1.38 (m, 14H); 1.52-1.79 (m, 4H); 1.91-2.09 (m, 3H); 2.13-2.32 (m, 2H); 2.36 (dd, J=15.2, 9.2 Hz, 1H); 2.44-2.57 (m, 2H); 2.63-2.73 (m, 1H); 2.75-3.03 (m, 5H); 3.88 (s, 6H); 4.09 (t, J=6.4 Hz, 2H); 4.26-4.36 (m, 2H); 6.43 (s, 2H).

NMR $^{13}$C (100 MHz, CDCl$_3$): δ=14.3; 22.8; 25.1; 26.0; 26.3; 26.5; 28.7; 29.4-29.7; 31.1; 32.0; 41.9; 42.2; 43.4; 45.3; 52.0; 56.5; 65.1; 68.3; 68.9; 105.2; 132.8; 133.2; 147.2; 172.5.

Mass (ESI+): m/z (%) 625 [M+K]$^+$ (4), 609 [M+Na]$^+$ (100).

HRMS (ESI+): m/z calculated for $C_{30}H_{50}O_7NaS_2$ 609.2896, found 609.2892.

Example 14

Preparation of decyl (2S,4R,6R)- and (2R,4S,6S)-(4-Hydroxy-3,5-dimethoxy-11-oxo-1,7-dioxadispiro[5.1.5.2]pentadeca-9,12-dien-2-yl)-acetate (10'b) and decyl (2S,4R,6S) and (2R,4S,6R)-(4-Hydroxy-3,5-dimethoxy-11-oxo-1,7-dioxadispiro[5.1.5.2]pentadeca-9,12-dien-2-yl)-acetate (11'b)

PIFA (422 mg, 0.98 mmol) is added, in the dark and in one go, to a solution of the syn diol 8'b (180 mg, 0.30 mmol) in 6.6 mL of an acetone/water mixture (9:1). After stirring for 15 minutes at ambient temperature, the reaction medium is quenched by the addition of a saturated solution of $NaHCO_3$ before being extracted with AcOEt. The organic phases are combined, dried over $MgSO_4$ and concentrated under vacuum. Purification is carried out on silica gel (cyclohexane/AcOEt 4:6 to 3:7) in order to produce the expected products 10'b (39 mg, 80 µmol, 26%) and 11'b (17 mg, 34 µmol, 11%) in the form of colourless oils.

10'b

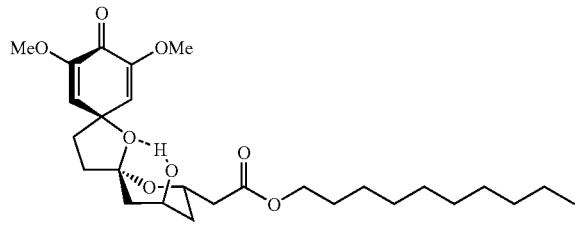

$C_{27}H_{42}O_8$
M=494.6 g.mol$^{-1}$
NMR $^1$H (400 MHz, CDCl$_3$): δ=0.88 (t, J=6.4 Hz, 3H); 1.20-1.38 (m, 14H); 1.47-1.56 (m, 1H); 1.58-1.69 (m, 2H); 1.78-1.85 (m, 1H); 1.91-2.06 (m, 4H); 2.20 (dd, J=11.2, 7.2 Hz, 1H); 2.36-2.54 (m, 3H); 3.67 (s, 3H); 3.81 (s, 3H); 4.02-4.13 (m, 2H); 4.14-4.18 (m, 1H); 4.63-4.72 (m, 1H); 5.66 (d, J=2.2 Hz, 1H); 6.32 (d, J=2.2 Hz, 1H).
NMR $^{13}$C (100 MHz, CDCl$_3$): δ=14.3; 22.9; 26.2; 28.9; 29.5-29.9; 32.1; 36.0; 37.8; 39.0; 39.2; 40.9; 56.2; 55.5; 62.7; 64.8; 64.9; 82.0; 108.2; 116.5; 120.0; 148.9; 149.4; 171.5; 176.9.
HRMS (ESI+): m/z calculated for $C_{27}H_{42}O_8Na$ 517.2777, found 517.2767.

$C_{27}H_{42}O_8$

M=494.6 g.mol$^{-1}$

NMR $^1$H (400 MHz, CDCl$_3$): δ=0.88 (t, J=6.8 Hz, 3H, 3×H10''); 1.21-1.38 (m, 14H, 2×H3'', 2×H4'', 2×H5'', 2×H6'', 2×H7'', 2×H8'', 2×H9''); 1.56-1.72 (m, 4H, 2×H2'', H3a, H3b); 1.91 (dd, J=14.0, 3.6 Hz, 1H, H5a); 1.99-2.14 (m, 3H, H15a, H5b, H14a); 2.32-2.43 (m, 1H, H14b); 2.50 (dd, J=15.4, 4.0 Hz, 1H, H2' a); 2.65 (dd, J=15.4, 9.2 Hz, 1H, H2'b); 2.74-2.81 (m, 1H, H15b); 3.67 (s, 3H, —OCH$_3$); 3.68 (s, 3H, —OCH$_3$); 4.02-4.14 (m, 2H, 2×H1''); 4.38-4.49 (m, 2H, H4, H2); 5.68 (d, J=2.4 Hz, 1H, H9); 5.94 (d, J=2.4 Hz, 1H, H13).

NMR $^{13}$C (100 MHz, CDCl$_3$): δ=14.3; 22.9; 26.2; 28.9; 29.5-29.7; 32.1; 35.9; 37.4; 40.7; 41.2; 55.4; 65.0; 65.1; 66.6; 79.7; 108.2; 116.8; 119.7; 149.0; 149.3; 171.4; 176.2.

HRMS (ESI+): m/z calculated for $C_{27}H_{42}O_8Na$ 517.2777, found 517.2775.

Example 15

Preparation of octadecyl (5R)- and (5S)-5-Hydroxy-6-{2-[2-(4-hydroxyphenyl)-ethyl]-[1,3]-dithian-2-yl}-3-oxohexanoate (6c)

Commercial 1-octadecanol (956 mg, 3.53 mmol) is added to a solution of the phenolic derivative 5 (500 mg, 1.18 mmol) in 16 mL of anhydrous toluene. The reaction medium is taken to 110° C. for 6 h before being concentrated under vacuum. Purification is carried out on a silica column (cyclohexane/AcOEt 8:2 to 7:3) in order to produce the racemic mixture of the β-ketoester (480 mg, 0.75 mmol, 64%) in the form of a colourless oil. This product is in fact a mixture of two compounds in equilibrium: the β-ketoester and its corresponding enolic form in a ratio of 9:1.

11'b

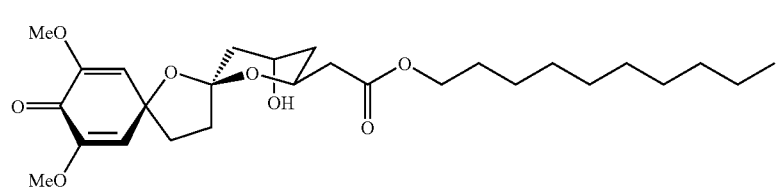

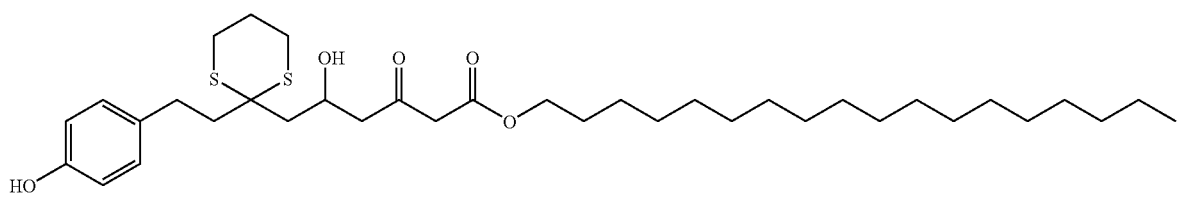

6c

C$_{36}$H$_{60}$O$_5$S$_2$
M=637.0 g.mol$^{-1}$
NMR $^1$H (400 MHz, CDCl$_3$): δ=0.88 (t, J=6.6 Hz, 3H); 1.23-1.33 (m, 30H); 1.59-1.68 (m, 2H); 1.88-2.07 (m, 3H); 2.14-2.27 (m, 2H); 2.34 (dd, J=15.0, 8.8 Hz, 1H); 2.61 (dd, J=17.2, 4.6 Hz, 1H); 2.69-2.99 (m, 7H); 3.50 (d, J=2.0 Hz, 2H); 4.13 (t, J=6.8 Hz, 2H); 4.44-4.52 (m, 1H); 6.75 (d, J=8.6 Hz, 2H); 7.06 (d, J=8.6 Hz, 2H).
NMR $^{13}$C (100 MHz, CDCl$_3$): δ=14.1; 22.7; 24.9; 25.8; 26.0; 26.3; 28.4; 29.2-29.7; 31.9; 41.7; 43.8; 49.9; 50.2; 51.8; 65.0; 65.8; 115.4; 129.6; 133.4; 154.0; 167.4; 202.2.
Mass (FAB+, NBA): m/z (%) 659 [M+Na]$^+$ (6), 636 [M]$^+$ (4), 511 (74), 239 (100).
HRMS (IE): m/z calculated for C$_{36}$H$_{60}$O$_5$S$_2$ 636.3882, found 636.3845.

Example 16

Preparation of octadecyl (3S,5R)- and (3R,5S)-3,5-Dihydroxy-6-{2-[2-(4-hydroxyphenyl)-ethyl]-[1,3]-dithian-2-yl}-hexanoate (8c)

1.48 mL of a commercial 1M solution of BEt$_3$ in hexane then 1.7 mL of anhydrous MeOH are added, at ambient temperature and under argon, to a solution of the ketone 6c (450 mg, 0.71 mmol) in 4.0 mL of anhydrous THF. After stirring for 1 h at ambient temperature, the reaction medium is cooled down to −78° C. then NaBH$_4$ (56 mg, 1.48 mmol) is added in one go. After stirring for 2 h, the reaction medium is quenched at −78° C. by the addition of a methanol buffer (pH=7, AcONa/AcOH). After stiffing overnight at ambient temperature, the reaction medium is concentrated, taken up in a saturated aqueous solution of K$_2$CO$_3$ then extracted with AcOEt. The organic phases are then combined, dried over MgSO$_4$, filtered and concentrated under vacuum. The residue is then taken up in MeOH and stirred for 3 days at ambient temperature. After evaporation of the MeOH, purification is carried out on silica gel (cyclohexane/AcOEt 9:1 to 7:3) in order to produce the racemic mixture of the diol of syn configuration (257 mg, 0.40 mmol, 57%) in the form of a colourless oil.

C$_{36}$H$_{62}$O$_5$
M=639.0 g.mol$^{-1}$
NMR $^1$H (400 MHz, CDCl$_3$): δ=0.88 (t, J=6.6 Hz, 3H); 1.22-1.35 (m, 30H); 1.45-1.51 (m, 1H); 1.57-1.66 (m, 2H); 1.68-1.75 (m, 1H); 1.90-2.06 (m, 3H); 2.11-2.31 (m, 2H); 2.36 (dd, J=15.2, 8.8 Hz, 1H); 2.47 (dd, J=16.0, 4.8 Hz, 1H); 2.53 (dd, J=16.0, 7.8 Hz, 1H); 2.62-2.71 (m, 1H); 2.73-3.01 (m, 5H); 4.09 (t, J=7.0 Hz, 2H); 4.23-4.40 (m, 2H); 6.77 (d, J=8.6 Hz, 2H); 7.04 (d, J=8.6 Hz, 2H).
NMR $^{13}$C (100 MHz, CDCl$_3$): δ=14.1; 22.7; 24.8; 25.9; 26.0; 26.3; 28.5; 29.2-29.7; 31.9; 41.8; 41.9; 43.0; 44.9; 51.8; 65.0; 68.2; 68.9; 115.5; 129.5; 133.1; 154.3; 172.5.
Mass (ESI+): m/z (%) 677 [M+K]$^+$ (7), 661 [M+Na]$^+$ (100).
HRMS (ESI+): m/z calculated for C$_{36}$H$_{62}$O$_5$NaS$_2$ 661.3936, found 661.3941.

Example 17

Preparation of octadecyl (2S,4R,6R)- and (2R,4S,6S)-(4-Hydroxy-11-oxo-1,7-dioxadispiro[5.1.5.2]pentadeca-9,12-dien-2-yl)-acetate (10c) and octadecyl (2S,4R,6S)- and (2R,4S,6R)-(4-Hydroxy-11-oxo-1,7-dioxadispiro[5.1.5.2]pentadeca-9.12 dien-2-yl)-acetate (11c)

PIFA (388 mg, 0.90 mmol) is added, in one go, to a solution of the syn diol 8c (180 mg, 0.28 mmol) in 10 mL of an acetone/water mixture (9:1). After stiffing for 15 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (cyclohexane/AcOEt 8:2) in order to produce the expected products 10c (30 mg, 55 μmol, 19%) and 11c (22 mg, 40 μmol, 14%) in the form of colourless oils.

8c

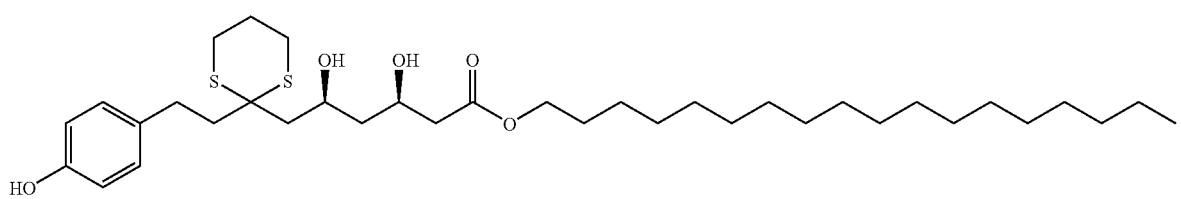

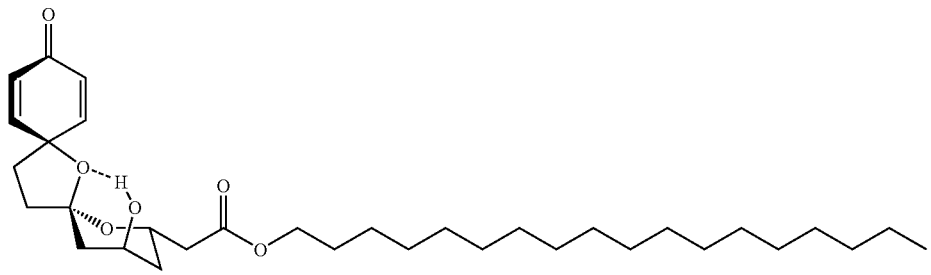

10c $C_{33}H_{54}O_6$
M=546.8 g.mol$^{-1}$

NMR $^1$H (400 MHz, CDCl$_3$): δ=0.88 (t, J=6.8 Hz, 3H); 1.22-1.39 (m, 30H); 1.51 (ddd, J=13.6, 12.0, 2.8 Hz, 1H); 1.60-1.68 (m, 2H); 1.80-1.86 (m, 1H); 1.91-2.05 (m, 4H); 2.16-2.24 (m, 1H); 2.29-2.38 (m, 1H); 2.42-2.55 (m, 2H); 4.03-4.10 (m, 1H); 4.11-4.20 (m, 2H); 4.60-4.67 (m, 1H); 6.10 (dd, J=10.0, 2.0 Hz, 1H); 6.19 (dd, J=10.0, 2.0 Hz, 1H); 6.76 (dd, J=10.0, 3.2 Hz, 1H); 7.16 (dd, J=10.0, 3.2 Hz, 1H).

NMR $^{13}$C (100 MHz, CDCl$_3$): δ=14.3; 22.9; 26.1; 28.9; 29.5; 29.6-29.9; 32.1; 34.2; 37.7; 38.8; 39.1; 41.0; 62.7; 64.7; 65.1; 80.3; 109.0; 127.3; 127.7; 148.6; 151.6; 171.4; 185.5.

Mass (ESI+): m/z (%) 569 [M+Na]$^+$ (100), 529 [M+H—H$_2$O]$^+$ (4), 511 (20).

HRMS (IE): m/z calculated for C$_{33}$H$_{54}$O$_6$ 546.3920, found 546.3901.

HRMS (IE): m/z calculated for C$_{33}$H$_{54}$O$_6$ 546.3920, found 546.3922.

Example 18

Preparation of octadecyl (3S,5S)- and (3R,5R)-3,5-Dihydroxy-6-{2-[2-(4-hydroxyphenyl)-ethyl]-[1,3]-dithian-2-yl}-hexanoate (9c)

A solution of the ketone 6c (200 mg, 0.31 mmol) in 2.25 mL of a CH$_3$CN/CH$_2$Cl$_2$ mixture (2:1) is added dropwise, at 0° C., to a suspension of Me$_4$NBH(OAc)$_3$ (330 mg, 1.26 mmol) in 3.75 mL of a CH$_3$CN/AcOH mixture (4:1). After stirring for 3 h at 0° C., the reaction medium is diluted with AcOEt then poured into 20 mL of a saturated aqueous solution of mixed sodium and potassium tartrate. After filtration of the precipitate formed through cotton, the phases are separated and the aqueous phase is extracted again with AcOEt. The organic phases are then combined, dried over MgSO$_4$, filtered and concentrated under vacuum. Purification is carried out on silica gel (cyclohexane/AcOEt 8:2) in order to produce the racemic mixture of the diol of anti configuration (169 mg, 0.26 mmol, 84%) in the form of a colourless oil.

Syn/anti mixture 2:8.

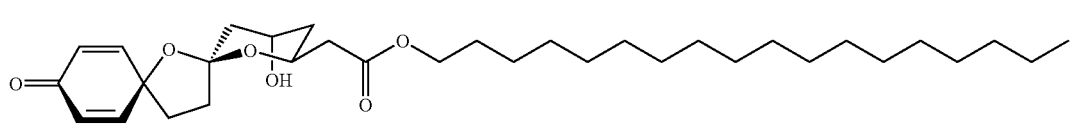

11c $C_{33}H_{54}O_6$
M=546.8 g.mol$^{-1}$

NMR $^1$H (400 MHz, CDCl$_3$): δ=0.88 (t, J=7.0 Hz, 3H); 1.22-1.40 (m, 30H); 1.58-1.72 (m, 4H); 1.87-2.13 (m, 4H); 2.19-2.37 (m, 1H); 2.44-2.57 (m, 1H); 2.64 (dd, J=15.2, 9.2 Hz, 1H); 2.72-2.79 (m, 1H); 4.03-4.18 (m, 2H); 4.37-4.47 (m, 2H); 6.11 (dd, J=10.0, 3.0 Hz, 1H); 6.11 (dd, J=10.0, 3.0 Hz, 1H); 6.76 (dd, J=10.0, 3.0 Hz, 1H); 6.90 (dd, J=10.0, 3.0 Hz, 1H).

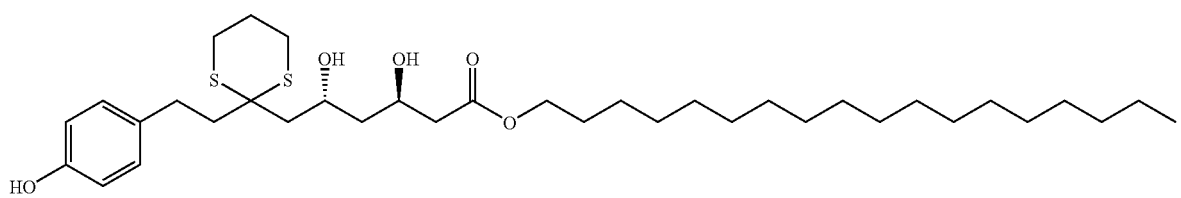

9c

NMR $^{13}$C (100 MHz, CDCl$_3$): δ=14.3; 22.9; 26.2; 28.9; 29.5; 29.6-29.9; 32.1; 35.4; 35.7; 37.4; 40.5; 41.1; 65.0; 65.1; 67.0; 78.1; 108.8; 127.5; 149.2; 152.1; 171.2; 185.8.

Mass (ESI+): m/z (%) 569 [M+Na]$^+$ (100), 529 [M+H—H$_2$O]$^+$ (20), 511 (38).

$C_{36}H_{62}O_5S_2$
M=639.0 g.mol$^{-1}$

NMR $^1$H (400 MHz, CDCl$_3$): δ=0.88 (t, J=6.8 Hz, 3H); 1.23-1.35 (m, 30H); 1.58-1.74 (m, 4H); 1.86-2.10 (m, 3H); 2.09-2.30 (m, 2H); 2.32-2.55 (m, 3H); 2.56-3.01 (m, 6H); 4.09 (t, J=6.8 Hz, 2H); 4.33-4.43 (m, 2H); 6.74 (d, J=8.6 Hz, 2H); 7.04 (d, J=8.6 Hz, 2H).

NMR $^{13}$C (100 MHz, CDCl$_3$): δ=14.3; 22.8; 25.0; 26.0; 26.2; 26.4; 28.7; 29.4-29.8; 32.1; 41.7; 42.1; 43.2; 44.8; 52.1; 65.2; 65.7; 66.1; 115.6; 129.6; 133.1; 154.5; 173.0.

Mass (ESI+): m/z (%) 661 [M+Na]$^+$ (88), 639 [M+H]$^+$ (3), 107 (100).

HRMS (ESI+): m/z calculated for C$_{36}$H$_{62}$O$_5$NaS$_2$ 661.3936, found 661.3931.

Example 19

Preparation of octadecyl (2S,4S,6R)- and (2R,4R,6S)-(4-Hydroxy-11-oxo-1,7-dioxadispiro[5.1.5.2]pentadeca-9,12-dien-2-yl)-acetate (12c) and octadecyl (2S,4S,6S)- and (2R,4R,6R)-(4-Hydroxy-11-oxo-1,7-dioxadispiro[5.1.5.2]pentadeca-9,12-dien-2-yl)-acetate (13c)

PIFA (323 mg, 0.75 mmol) is added, in one go, to a solution of the anti diol 9c (150 mg, 0.23 mmol) in 10 mL of an acetone/water mixture (9:1). After stirring for 10 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (cyclohexane/AcOEt 8:2) in order to produce the expected products 12c (20 mg, 37 μmol, 16%) and 13c (20 mg, 37 μmol, 16%) in the form of colourless oils.

C$_{33}$H$_{54}$O$_6$

M=546.8 g.mol$^{-1}$

NMR $^1$H (400 MHz, CDCl$_3$): δ=0.89 (t, J=6.8 Hz, 3H); 1.23-1.38 (m, 31H); 1.58-1.73 (m, 2H); 1.78-1.91 (m, 2H); 1.99-2.10 (m, 2H); 2.15 (ddd, J=12.4, 4.4 Hz, 1.2 Hz, 1H); 2.25-2.35 (m, 1H); 2.46-2.55 (m, 2H); 2.67 (dd, J=15.6, 8.8 Hz, 1H); 3.88-3.97 (m, 2H); 4.05-4.16 (m, 2H); 6.11 (dd, J=10.0, 2.0 Hz, 1H); 6.14 (dd, J=10.0, 2.0 Hz, 1H); 6.78 (dd, J=10.0, 3.0 Hz, 1H); 6.91 (dd, J=10.0, 3.0 Hz, 1H).

NMR $^{13}$C (100 MHz, CDCl$_3$): δ=14.4; 22.9; 26.2; 28.9; 29.5; 29.6-29.9; 32.2; 33.6; 35.0; 40.0; 41.0; 43.3; 65.2; 66.8; 68.5; 78.5; 109.4; 127.4; 127.7; 148.8; 151.5; 171.4; 185.6.

HRMS (ESI+): m/z calculated for C$_{33}$H$_{54}$O$_6$Na 569.3818, found 569.3799.

12c

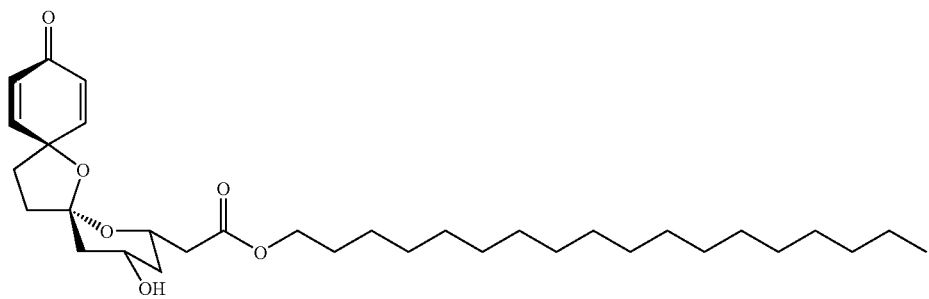

C$_{33}$H$_{54}$O$_6$

M=546.8 g.mol$^{-1}$

NMR $^1$H (400 MHz, CDCl$_3$): δ=0.89 (t, J=6.8 Hz, 3H); 1.23-1.39 (m, 31H); 1.52-1.80 (m, 3H); 1.95-2.13 (m, 4H); 2.17-2.26 (m, 1H); 2.29-2.38 (m, 1H); 2.43-2.58 (m, 2H); 4.04-4.21 (m, 3H); 4.29-4.36 (m, 1H); 6.11 (dd, J=10.0, 2.0 Hz, 1H); 6.17 (dd, J=10.0, 2.0 Hz, 1H); 6.77 (dd, J=10.0, 3.0 Hz, 1H); 7.09 (dd, J=10.0, 3.0 Hz, 1H).

NMR $^{13}$C (100 MHz, CDCl$_3$): δ=14.4; 22.9; 26.1; 28.9; 29.5-29.9; 32.1; 34.7; 38.8; 40.2; 41.1; 42.7; 65.1; 66.0; 79.4; 109.0; 127.1; 127.4; 149.2; 152.2; 171.4; 185.8.

HRMS (IE): m/z calculated for C$_{33}$H$_{54}$O$_6$ 546.3920, found 546.3912.

Example 20

Preparation of 1-decylundecyl (5R)- and (5S)-5-Hydroxy-6-{2-[2-(4-hydroxyphenyl)-ethyl]-[1,3]-dithian-2-yl}-3-oxohexanoate (6d)

Commercial 11-heneicosanol (736 mg, 2.36 mmol) is added to a solution of the phenolic derivative 5 (500 mg, 1.18 mmol) in 15 mL of anhydrous toluene. The reaction medium is taken to 110° C. for 9 h before being concentrated under vacuum. Purification is carried out on silica gel (cyclohexane/AcOEt 8:2) in order to produce the racemic mixture of the β-ketoester (279 mg, 0.41 mmol, 35%) in the form of a colourless oil. This product is in fact a mixture of two compounds in equilibrium: the β-ketoester and its corresponding enolic form in a ratio of 88:12.

13c

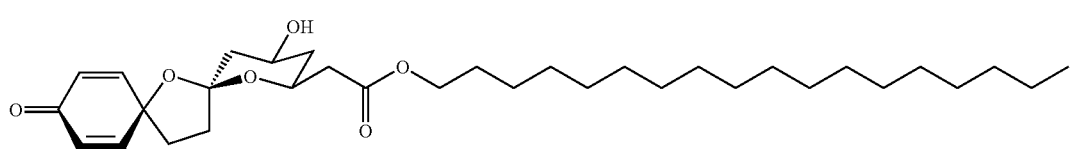

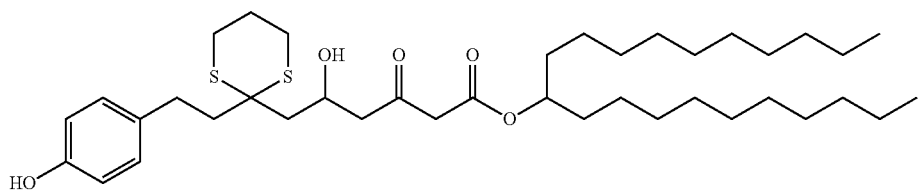

6d

C$_{39}$H$_{66}$O$_5$S$_2$
M=679.1 g.mol$^{-1}$
NMR $^1$H (400 MHz, CDCl$_3$): δ=0.88 (t, J=7.0 Hz, 6H); 1.20-1.34 (m, 32H); 1.50-1.58 (m, 4H); 1.88-2.08 (m, 3H); 2.15-2.31 (m, 2H); 2.33 (dd, J=15.2, 8.8 Hz, 1H); 2.59 (dd, J=17.2, 4.4 Hz, 1H); 2.68-2.99 (m, 7H); 3.48 (d, J=4.4 Hz, 2H); 4.44-4.52 (m, 1H); 4.92 (quint., J=6.2 Hz, 1H); 6.75 (d, J=8.4 Hz, 2H); 7.06 (d, J=8.4 Hz, 2H).
NMR $^{13}$C (100 MHz, CDCl$_3$): δ=14.3; 22.9; 25.1; 25.5; 26.2; 26.5; 29.5-29.8; 32.1; 34.1; 41.9; 44.0; 50.4; 50.5; 52.1; 65.2; 76.4; 115.6; 129.8; 133.7; 154.2; 167.3; 202.5.
Mass (ESI+): m/z (%) 701 [M+Na]$^+$ (100), 679 [M+1-1]$^+$ (11).
HRMS (IE): m/z calculated for C$_{39}$H$_{66}$O$_5$S$_2$ 678.4352, found 678.4365.

Example 21

Preparation of 1-decylundecyl (3S,5R)- and (3R,5S)-3,5-Dihydroxy-6-{2-[2-(4-hydroxyphenyl)-ethyl]-[1,3]-dithian-2-yl}-hexanoate (8d)

0.77 mL of a commercial 1M solution of BEt$_3$ in hexane then 1.0 mL of anhydrous MeOH are added, at ambient temperature and under argon, to a solution of the ketone 6d (250 mg, 0.37 mmol) in 2.6 mL of anhydrous THF. After stiffing for 1 h at ambient temperature, the reaction medium is cooled down to −78° C. then NaBH$_4$ (37 mg, 0.98 mmol) is added in one go. After stirring for 2 h, the reaction medium is quenched at −78° C. by the addition of a methanol buffer (pH=7, AcONa/AcOH). After stiffing overnight at ambient temperature, the reaction medium is concentrated, taken up in a saturated aqueous solution of K$_2$CO$_3$ then extracted with AcOEt. The organic phases are then combined, dried over MgSO$_4$, filtered and concentrated under vacuum. The residue is then taken up in MeOH and stirred overnight at ambient temperature. After evaporation of the MeOH, purification is carried out on silica gel (cyclohexane/AcOEt 8:2) in order to produce the racemic mixture of the diol of syn configuration (249 mg, 0.37 mmol, 99%) in the form of a colourless oil.

C$_{39}$H$_{68}$O$_5$S$_2$
M=681.1 g.mol$^{-1}$
NMR $^1$H (400 MHz, CDCl$_3$): δ=0.88 (t, J=7.0 Hz, 6H); 1.19-1.34 (m, 32H); 1.47-1.56 (m, 5H); 1.67-1.76 (m, 1H); 1.89-2.08 (m, 3H); 2.12-2.31 (m, 2H); 2.36 (dd, J=15.2, 8.8 Hz, 1H); 2.46 (dd, J=15.8, 4.8 Hz, 1H); 2.53 (dd, J=15.8, 7.6 Hz, 1H); 2.62-2.71 (m, 1H); 2.74-2.99 (m, 5H); 4.25-4.34 (m, 2H); 4.91 (quint., J=6.0 Hz, 1H); 6.76 (d, J=8.4 Hz, 2H); 7.04 (d, J=8.4 Hz, 2H).
NMR $^{13}$C (100 MHz, CDCl$_3$): δ=14.3; 22.9; 25.1; 25.5; 26.2; 26.5; 29.5-29.9; 32.0; 34.2; 42.1; 43.2; 45.1; 52.1; 68.5; 69.1; 75.4; 115.7; 129.7; 133.4; 154.4; 172.5.
Mass (ESI+): m/z (%) 703 [M+Na]$^+$ (100), 681 [M+H]$^+$ (6).
HRMS (IE): m/z calculated for C$_{39}$H$_{68}$O$_5$S$_2$ 680.4508, found 680.4531.

Example 22

Preparation of 1-decylundecyl (2S,4R,6R)- and (2R,4S,6S)-(4-Hydroxy-11-oxo-1,7-dioxadispiro[5.1.5.2]pentadeca-9,12-dien-2-yl)-acetate (10d) and 1-decylundecyl (2S,4R,6S)- and (2R,4S,6R)-(4-Hydroxy-1'-oxo-1,7-dioxadispiro[5.1.5.2]pentadeca-9,12-dien-2-yl)-acetate (11d)

PIFA (465 mg, 1.08 mmol) is added, in the dark and in one go, to a solution of syn diol 8d (230 mg, 0.34 mmol) in 12.2 mL of an acetone/water mixture (9:1). After stirring for 15 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (cyclohexane/AcOEt 9:1) in order to produce the expected products 10d (24 mg, 41 μmol, 12%) and 11d (22 mg, 37 μmol, 11%) in the form of colourless oils.

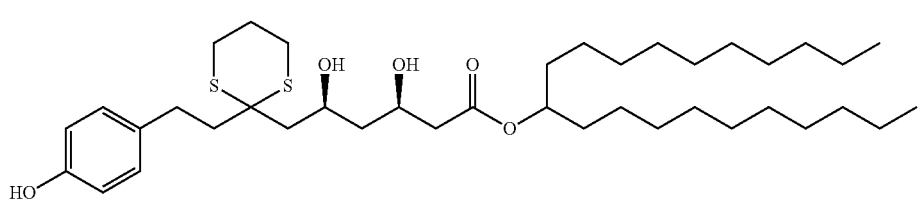

8d

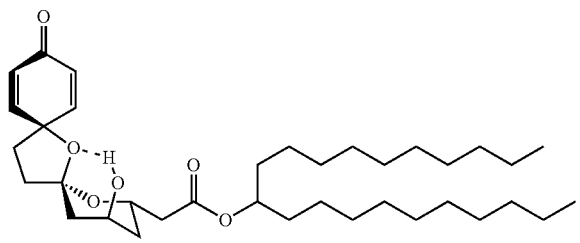

10d

C$_{36}$H$_{60}$O$_6$
M=588.9 g.mol$^{-1}$

NMR $^1$H (400 MHz, CDCl$_3$): δ=0.87 (t, J=7.2 Hz, 3H); 0.88 (t, J=6.8 Hz, 3H); 1.20-1.36 (m, 32H); 1.48-1.56 (m, 5H); 1.79-1.86 (m, 1H); 1.91-2.05 (m, 4H); 2.14-2.22 (m, 1H); 2.28-2.36 (m, 1H); 2.45-2.49 (m, 2H); 4.12-4.19 (m, 1H); 4.61-4.69 (m, 1H); 4.93 (quint., 1H); 6.10 (dd, J=10.2, 2.0 Hz, 1H); 6.20 (dd, J=10.0, 2.0 Hz, 1H); 6.75 (dd, J=10.2, 2.8 Hz, 1H); 7.16 (dd, J=10.0, 2.8 Hz, 1H).

NMR $^{13}$C (100 MHz, CDCl$_3$): δ=14.3; 22.9; 25.6; 29.5; 29.8; 32.1; 34.2; 34.5; 37.6; 38.9; 39.1; 41.2; 62.8; 64.8; 75.0; 80.3; 109.1; 127.3; 127.7; 148.6; 151.7; 171.2; 185.6.

Mass (ESI+): m/z (%) 611 [M+Na]$^+$ (100), 571 [M+H—H$_2$O]$^+$ (2).

HRMS (IE): m/z calculated for C$_{36}$H$_{60}$O$_6$ 588.4390, found 588.4380.

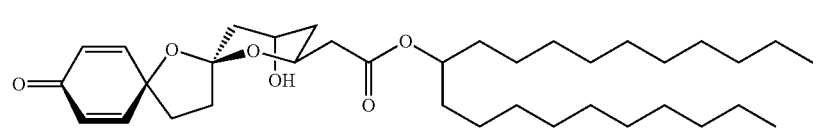

11d

C$_{36}$H$_6$O$_6$
M=588.9 g.mol$^{-1}$

NMR $^1$H (400 MHz, CDCl$_3$): δ=0.88 (t, J=6.8 Hz, 6H); 1.20-1.34 (m, 32H); 1.48-1.57 (m, 4H); 1.60-1.67 (m, 2H); 1.87-2.11 (m, 4H); 2.31-2.40 (m, 1H); 2.45 (dd, J=15.8, 4.2 Hz, 1H); 2.63 (dd, J=15.8, 9.0 Hz, 1H); 2.73-2.80 (m, 1H); 4.36-4.48 (m, 2H); 4.89 (quint., J=6.4 Hz, 1H); 6.09 (dd, J=10.2, 2.0 Hz, 1H); 6.11 (dd, J=10.2, 2.0 Hz, 1H); 6.76 (dd, J=10.2, 3.1 Hz, 1H); 6.92 (dd, J=10.2, 3.1 Hz, 1H).

NMR $^{13}$C (100 MHz, CDCl$_3$): δ=14.3; 22.9; 25.6; 29.3; 29.7-29.8; 32.1; 34.3; 35.4; 35.7; 37.3; 40.5; 41.2; 64.9; 66.7; 75.1; 78.1; 108.8; 127.3; 127.4; 149.2; 152.2; 171.2; 185.8.

Mass (ESI+): m/z (%) 611 [M+Na]$^+$ (100), 571 [M+H—H$_2$O]$^+$ (3).

HRMS (ESI+): m/z calculated for C$_{36}$H$_{60}$O$_6$Na 611.4288, found 611.4297.

Example 23

Preparation of 5-Hydroxy-6-{2-[2-(4-hydroxyphenyl)-ethyl]-[1,3]-dithian-2-yl}-3-oxohexanoic acid dihexylamide (6e)

Di-n-hexylamine (655 mg, 3.53 mmol) is added to a solution of the phenolic derivative 5 (500 mg, 1.18 mmol) in 15 mL of anhydrous toluene, then the reaction medium is taken to 110° C. After stirring for 6 h at this temperature, the reaction medium is concentrated under vacuum. Purification is carried out on a silica column (cyclohexane/AcOEt 95:5 up to 85:15) in order to produce the expected amide (293 mg, 0.53 mmol, 45%) in the form of a colourless oil. This compound is in fact a mixture of two compounds in equilibrium, β-ketoamide compound and its corresponding enolic form in a ratio of 8:2.

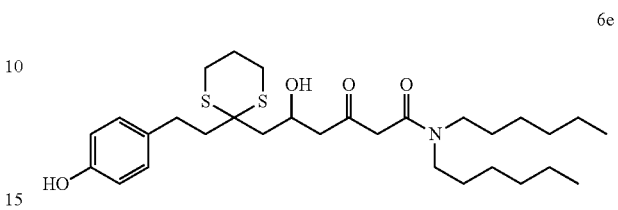

6e

C$_{30}$H$_{49}$NO$_4$S$_2$
M=551.9 g.mol$^{-1}$

NMR $^1$H (400 MHz, CDCl$_3$): δ=0.84 (2t, J=6.8 Hz, 3H, 3×H6'); 0.93 (2t, J=6.8 Hz, 3H, 3×H6'); 1.23-1.35 (m, 12H, 4×H3', 4×H4', 4×H5'); 1.48-1.60 (m, 4H, 4×H2'); 1.85-2.07 (m, 3H, —SCH$_2$CH$_2$—, H6a); 2.10-2.50 (m, 4H, 2×H1″, H6b, H4a); 2.64-3.01 (m, 7H, 2×H2″, H4b, 2×-SCH$_2$—); 3.12-3.22 (m, 2H, 2×H1'); 3.23-3.42 (m, 2H, 2×H1'); 3.54 (s, 2H, 2×H2); 4.36-4.46 (m, 1H, H5); 6.76 (d, J=8.2 Hz, 2H, 2×H3‴); 7.02 (d, J=8.2 Hz, 2H, H2‴).

NMR $^{13}$C (100 MHz, CDCl$_3$): δ=14.1; 22.7; 25.1; 26.2; 26.5; 26.6-29.7; 31.6; 31.7; 41.4; 43.8; 46.4; 48.9; 49.4; 50.6; 52.2; 65.3; 115.9; 129.7; 133.1; 154.8; 166.9; 203.7.

Mass (ESI+): m/z (%) 590 [M+K]$^+$ (5), 574 [M+Na]$^+$ (100).

HRMS (ESI+): m/z calculated for C$_{30}$H$_{49}$NO$_4$NaS$_2$ 574.3001, found 574.2991.

Example 24

Preparation of 3,5-dihydroxy-6-{2-[2-(4-hydroxyphenyl)-ethyl]-[1,3]-dithian-2-yl}-hexanoic acid dihexylamide (7e)

A solution of the ketone 6e (242 mg, 0.44 mmol) in 6 mL of CH$_2$Cl$_2$ is added at 0° C. to a suspension of NaBH$_4$ (50 mg, 1.32 mmol) in 9 mL of MeOH. After stirring for 3 h at 0° C., the reaction medium is quenched by the addition of a saturated aqueous solution of NH$_4$Cl. After dilution of the reaction medium in a CH$_2$Cl$_2$ and H$_2$O mixture, it is extracted with CH$_2$Cl$_2$. The organic phases are then combined, dried over MgSO$_4$, filtered and concentrated under vacuum. Purification is carried out on a silica column (cyclohexane/AcOEt 8:2) in order to produce the mixture of 4 non-separable diastereoisomers of the expected alcohol (173 mg, 0.03 mmol, 76%) in the form of a yellow oil.

7e

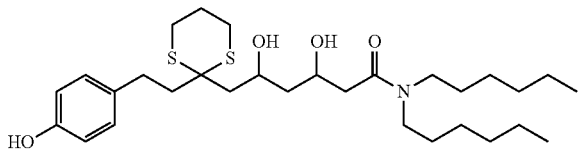

C$_{30}$H$_{51}$NO$_4$S$_2$
M=553.9 g.mol$^{-1}$

Mass (DCI, NH$_3$+isobutane): m/z (%) 576 [M+Na]$^+$ (18), 554 [M+H]$^+$ (21), 428 (100).

Example 25

Preparation of (2S,4R,6R)- and (2R,4S,6S)—N,N-dihexyl-2-(4-hydroxy-11-oxo-1,7-dioxadispiro[5.1.5.2]pentadeca-9,12-dien-2-yl)-acetamide (10e)

PIFA (298 mg, 0.69 mmol) is added, in the dark and in one go, to a solution of the diol 7e (120 mg, 0.22 mmol) in 5.5 mL of an acetone/water mixture (10:1). After stirring for 15 minutes at ambient temperature, the reaction medium is quenched by the addition of a saturated solution of NaHCO$_3$ before being extracted with AcOEt. The organic phases are combined, dried over MgSO$_4$ and concentrated under vacuum. Purification is carried out on silica gel (CH$_2$Cl$_2$/MeOH 99:1) in order to produce the expected majority product (11 mg, 24 µmol, 11%) in the form of a colourless oil (the other compounds formed have not been isolated).

10e

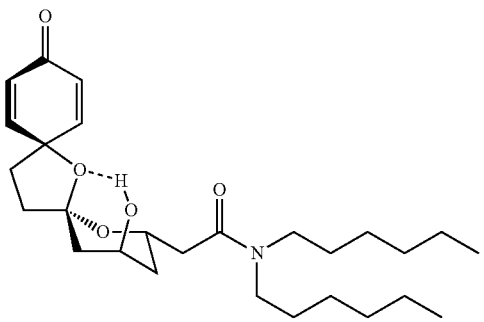

C$_{27}$H$_{43}$O$_5$N
M=461.6 g.mol$^{-1}$

NMR $^1$H (400 MHz, CDCl$_3$): δ=0.87 (t, J=6.8 Hz, 3H); 0.90 (t, J=6.8 Hz, 3H); 1.24-1.35 (m, 12H); 1.47-1.65 (m, 6H); 1.85-2.05 (m, 4H); 2.08-2.17 (m, 1H); 2.24-2.33 (m, 2H); 2.62 (dd, J=14.8, 9.4 Hz, 1H); 3.13-3.23 (m, 2H); 3.30-3.38 (m, 1H); 3.43-3.51 (m, 1H); 4.13-4.18 (m, 1H); 4.69-4.78 (m, 1H); 6.10 (dd, J=10.0, 1.8 Hz, 1H); 6.19 (dd, J=10.0, 1.8 Hz, 1H); 6.75 (dd, J=10.0, 3.0 Hz, 1H); 7.22 (dd, J=10.0, 3.0 Hz, 1H).

NMR $^{13}$C (100 MHz, CDCl$_3$): δ=14.2; 22.8; 26.7; 26.9; 28.2; 29.5; 31.8; 34.2; 38.0; 38.8; 39.1; 39.2; 46.7; 48.6; 63.7; 64.9; 80.2; 109.0; 127.2; 127.5; 148.8; 152.2; 170.1; 185.7.

Mass (ESI+): m/z (%) 500 [M+K]$^+$ (6), 484 [M+Na]$^+$ (100).

HRMS (ESI+): m/z calculated for C$_{27}$H$_{43}$NO$_5$Na 484.3039, found 484.3040.

Example 26

Preparation of (5R)- and (5S)-5-Hydroxy-1-(4-hydroxyphenyl)-6-{2-[2-(4-hydroxyphenyl)-ethyl]-[1,3]-dithian-2-yl}-hexan-3-one (3)

0.22 mL of BF$_3$.OEt$_2$ are added, dropwise, under argon and at −78° C., to a solution of the aldehyde 1 (200 mg, 0.71 mmol) and the trimethylsilyl enolate 2 (546 mg, 1.77 mmol) in 10 mL of anhydrous CH$_2$Cl$_2$. After stirring for 2 h at this temperature, an additional 2×0.5 eq. of silylenol ether are added. After stirring for 1 h, the reaction medium is quenched by the addition of 10 mL of a 1N aqueous solution of NaOH at ambient temperature. After extraction with AcOEt, the organic phases are dried over MgSO$_4$, filtered and concentrated under vacuum. The residue is then solubilized in CH$_2$Cl$_2$ then 2 eq. of TBAF are added at 0° C. After stirring for 1 h, a saturated aqueous solution of NH$_4$Cl is added. After extraction with AcOEt, the organic phases are dried over MgSO$_4$, filtered and concentrated under vacuum. Purification is carried out on a silica column (cyclohexane/AcOEt 7:3) in order to produce the expected compound (266 mg, 0.60 mmol, 84%) in the form of a colourless oil.

3

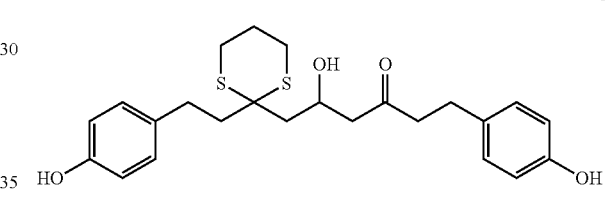

C$_{24}$H$_{30}$O$_4$S$_2$
M=446.6 g.mol$^{-1}$

NMR $^1$H (400 MHz, MeOD): δ=1.80-1.95 (m, 2H); 2.01-2.23 (m, 4H); 2.50-2.87 (m, 8H); 4.42 (s, 1H); 6.62-6.72 (m, 4H); 6.92-7.03 (m, 4H).

NMR $^{13}$C (100 MHz, MeOD): δ=26.4; 26.8; 27.0; 29.7; 30.7; 43.1; 45.4; 46.3; 52.3; 53.2; 66.4; 116.1; 130.2; 130.3; 133.1; 134.2; 156.3; 156.5; 211.4.

Mass (IE): m/z (%) 446 [M]$^+$ (1), 428 (4), 239 (100), 107 (70).

HRMS (ESI+): m/z calculated for C$_{24}$H$_{30}$O$_4$NaS$_2$ 469.1483, found 469.1489.

Example 27

Preparation of (8R,10S,21S)- and (8S,10R,21R)-21-Hydroxy-7,9,11-trioxatetraspiro[5.1.1.1.5$^{12}$.2$^{10}$.3$^8$.2$^6$]tetracosa-1,4,13,16-dien-3,15-one (4a) and (8R,10R,21S)-21-Hydroxy-7,9,11-trioxatetraspiro[5.1.1.1.5$^{12}$.2$^{10}$.3$^8$.2$^6$]tetracosa-1,4,13,16-dien-3,15-one (4b)

PIFA (1.25 g, 2.92 mmol) is added to a solution of the phenolic derivative 3 (217 mg, 0.49 mmol) in 18 mL of an acetone/H$_2$O mixture (9:1). After stirring overnight, the reaction medium is quenched by the addition of a saturated aqueous solution of NaHCO$_3$. After extraction with AcOEt, the organic phases are combined, dried over MgSO₄, filtered and concentrated under vacuum. Purification is carried out on a silica column (CH₂Cl₂/MeOH 98:2) in order to produce the separable diastereoisomers 4a (35 mg, 0.09 mmol, 19%) and 4b (20 mg, 0.06 mmol, 11%) in the form of colourless oils.

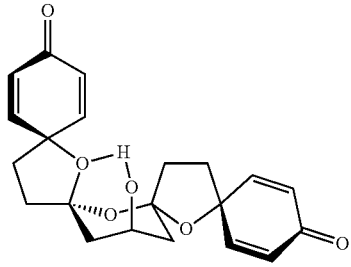

4a $C_{21}H_{22}O_6$
M=370.4 g.mol⁻¹

NMR ¹H (400 MHz, CDCl₃): δ=1.91-2.42 (m, 10H); 2.49-2.56 (ddd, J=12.4, 6.8, 2.0 Hz, 1H); 2.60-2.67 (m, 1H); 4.21-4.29 (m, 1H); 6.12-6.21 (m, 4H); 6.74-6.80 (m, 2H); 6.85 (dd, J=10.0, 3.0 Hz, 1H); 6.91 (dd, J=10.0, 3.0 Hz, 1H).

NMR ¹³C (100 MHz, CDCl₃): δ=35.0; 35.2; 38.6; 39.6; 41.8; 42.6; 63.6; 78.9; 109.0; 110.2; 127.3; 127.4; 127.7; 127.8; 148.4; 148.6; 150.3; 150.6; 185.2.

Mass (DCI, NH3+isobutane): m/z (%) 388 [M+NH₄]⁺ (7), 371 [M+H]⁺ (12), 353 (30), 316 (39), 288 (100).

HRMS (IE): m/z calculated for $C_{21}H_{22}O_6$ 370.1416, found 370.1421.

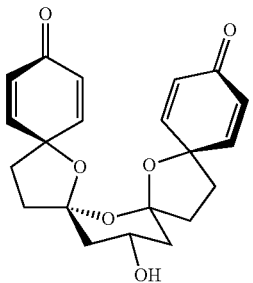

4b $C_{21}H_{22}O_6$
M=370.4 g.mol⁻¹

NMR ¹H (400 MHz, CDCl₃): δ=1.77 (dd, J=12.8, 10.4 Hz, 2H); 2.03-2.10 (m, 2H); 2.16-2.23 (m, 2H); 2.25-2.37 (m, 6H); 4.38-4.47 (m, 1H); 6.09-6.16 (m, 4H); 6.75 (dd, J=10.2, 2.8 Hz, 2H, H1); 7.02 (dd, J=10.2, 2.8 Hz, 2H).

NMR ¹³C (100 MHz, CDCl₃): δ=35.3; 40.4; 44.2; 62.0; 79.8; 110.1; 127.5; 127.7; 149.3; 150.6; 185.5.

Mass (DCI, NH3+isobutane): m/z (%) 388 [M+NH₄]⁺ (56), 371 [M+H]⁺ (37), 353 (99), 316 (43), 288 (89), 107 (100).

HRMS (IE): m/z calculated for $C_{21}H_{22}O_6$ 370.1416, found 370.1423.

Example 28

Preparation of (8R,10S,21S)- and (8S,10R,21R)-Heptanoate of 7,9,11-trioxatetraspiro[5.1.1.1.5¹².2¹⁰.3⁸.2⁶]tetracosa-1,4,13,16-dien-3,15-on-21-yl (16a)

DMAP (9.8 mg, 0.08 mmol), heptanoyl chloride (14.3 mg, 0.10 mmol) then triethylamine (9.7 mg, 0.10 mmol) are added, at 0° C. and under argon, to a solution of the alcohol 4a (29.7 mg, 0.08 mmol) in 2 mL of anhydrous CH₂Cl₂. After stiffing for 0.5 h at 0° C. and for 4 h at ambient temperature, the reaction medium is quenched by the addition of a 1N aqueous solution of HCl. After extraction with CH₂Cl₂, the organic phases are combined, dried over MgSO₄, filtered and concentrated under vacuum. Purification is carried out on silica gel (cyclohexane/AcOEt 7:3) in order to produce the expected ester (21.6 mg, 0.04 mmol, 56%) in the form of a colourless oil.

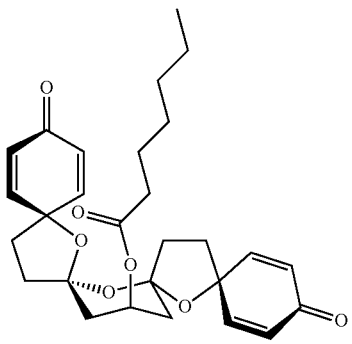

16a $C_{28}H_{34}O_7$
M=482.6 g.mol⁻¹

NMR ¹H (400 MHz, CDCl₃): δ=0.88 (t, J=6.2 Hz, 3H); 1.22-1.36 (m, 6H); 1.55-1.65 (m, 2H); 1.94-2.38 (m, 12H); 2.52 (ddd, J=12.8, 7.2, 3.6 Hz, 1H); 2.76-2.83 (m, 1H); 5.18-5.26 (m, 1H); 6.11-6.21 (m, 4H); 6.72-6.78 (m, 2H); 6.85 (dd, J=10.0, 2.8 Hz, 1H); 6.92 (dd, J=10.0, 2.8 Hz, 1H).

NMR ¹³C (100 MHz, CDCl₃): δ=14.2; 22.7; 25.1; 29.0; 31.6; 34.7; 35.5; 38.4; 39.8; 39.9; 66.1; 78.9; 79.6; 109.2; 110.1; 127.6; 127.8; 127.9; 128.2; 148.8; 149.9; 151.0; 173.4; 185.3; 185.5.

Example 29

Preparation of (8R,10R,21S)-Heptanoate of 7,9,11-trioxatetraspiro[5.1.1.1.5¹².2¹⁰.3⁸.2⁶]tetracosa-1,4,13,16-dien-3,15-on-21-yl (16b)

DMAP (6 mg, 0.05 mmol), heptanoyl chloride (8 mg, 0.06 mmol) then triethylamine (6 mg, 0.06 mmol) are added, at 0° C. and under argon, to a solution of the alcohol 4b (17 mg, 0.05 mmol) in 1 mL of anhydrous CH₂Cl₂. After stiffing for 0.5 h at 0° C. and for 4 h at ambient temperature, the reaction medium is quenched by the addition of a 1N aqueous solution of HCl. After extraction with CH₂Cl₂, the organic phases are combined, dried over MgSO₄, filtered and concentrated under vacuum. Purification is carried out on silica gel (cyclohexane/AcOEt 7:3) in order to produce the expected ester (7 mg, 14 μmol, 30%) in the form of a colourless oil.

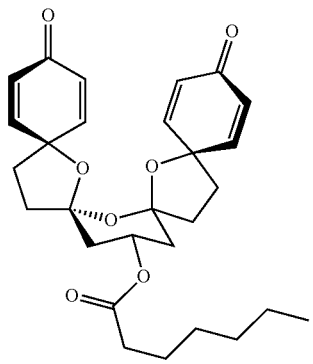

$C_{28}H_{34}O_7$
M=482.6 g.mol$^{-1}$
NMR $^1$H (400 MHz, CDCl$_3$): δ=0.88 (t, J=6.8 Hz, 3H); 1.22-1.37 (m, 6H); 1.55-1.65 (m, 2H); 1.87 (dd, J=13.5, 8.0 Hz, 2H); 2.04-2.19 (m, 4H); 2.26-2.38 (m, 6H); 2.49 (dd, J=13.5, 5.4 Hz, 2H); 5.32-5.40 (m, 1H); 6.09-6.17 (m, 4H); 6.75 (dd, J=10.0, 2.8 Hz, 2H, H1); 7.03 (dd, J=10.2, 2.8 Hz, 2H).
NMR $^{13}$C (100 MHz, CDCl$_3$): δ=14.2; 22.7; 25.1; 29.0; 31.6; 34.8; 35.4; 39.6; 40.2; 65.4; 79.6; 109.3; 127.6; 127.7; 149.2; 150.7; 173.1; 185.4.
Mass (ESI+): m/z (%) 521 [M+K]$^+$ (14), 505 [M+Na]$^+$ (100).
HRMS (ESI+): m/z calculated for $C_{28}H_{34}O_7$Na 505.2202, found 505.2204.

Example 30

Preparation of (8R,10S,21S)- and (8S,10R,21R)-Tetradecanoate of 7,9,11-trioxatetraspiro [5.1.1.1.5$^{12}$.2$^{10}$.3$^{8}$.2$^{6}$]tetracosa-1,4,13,16-dien-3,15-on-21-yl (16c)

DMAP (10.0 mg, 0.08 mmol), tetradecanoyl chloride (25.0 mg, 0.10 mmol) then triethylamine (10.1 mg, 0.10 mmol) are added, at 0° C. and under argon, to a solution of the alcohol 4a (31.0 mg, 0.08 mmol) in 3 mL of anhydrous CH$_2$Cl$_2$. After stirring for 0.5 h at 0° C. and for 4 h at ambient temperature, the reaction medium is quenched by the addition of a 1N aqueous solution of HCl. After extraction with CH$_2$Cl$_2$, the organic phases are combined, dried over MgSO$_4$, filtered and concentrated under vacuum. Purification is carried out on silica gel (cyclohexane/AcOEt 7:3) in order to produce the expected ester (26.7 mg, 0.05 mmol, 55%) in the form of a colourless oil.

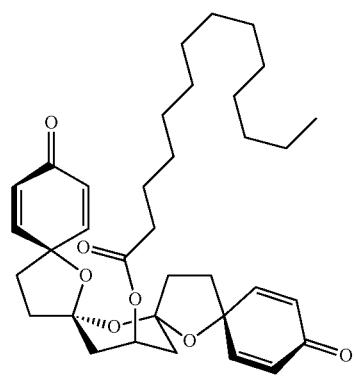

$C_{35}H_{48}O_7$
M=580.8 g.mol$^{-1}$
NMR $^1$H (400 MHz, CDCl$_3$): δ=0.88 (t, J=6.8 Hz, 3H); 1.23-1.34 (m, 20H); 1.55-1.65 (m, 2H); 1.94-2.38 (m, 12H); 2.52 (ddd, J=12.8, 7.6, 3.6 Hz, 1H); 2.80 (ddd, J=12.8, 7.2, 2.0 Hz, 1H); 5.18-5.27 (m, 1H); 6.11-6.20 (m, 4H); 6.72-6.77 (m, 2H); 6.85 (dd, J=10.0, 3.0 Hz, 1H); 6.92 (dd, J=10.0, 3.0 Hz, 1H).
NMR $^{13}$C (100 MHz, CDCl$_3$): δ=14.3; 22.9; 25.1; 29.3-29.9; 32.1; 34.6; 35.4; 38.3; 39.8; 39.9; 66.1; 78.9; 79.6; 109.2; 110.1; 127.6; 127.7; 127.9; 128.2; 148.7; 148.8; 149.9; 151.0; 173.4; 185.3; 185.4.
Mass (ESI+): m/z (%) 619 [M+K]$^+$ (15), 603 [M+Na]$^+$ (100).
HRMS (ESI+): m/z calculated for $C_{35}H_{48}O_7$Na 603.3298, found 603.3295.

Example 31

Preparation of the (8R,10R,21S)-Tetradecanoate of 7,9,11-trioxatetraspiro[5.1.1.1.5$^{12}$.2$^{10}$.3$^{8}$.2$^{6}$]tetracosa-1,4,13,16-dien-3,15-on-21-yl (16d)

DMAP (3.9 mg, 0.03 mmol), tetradecanoyl chloride (10 mg, 0.04 mmol) then triethylamine (4.0 mg, 0.04 mmol) are added, at 0° C. and under argon, to a solution of the alcohol 4b (12.1 mg, 0.03 mmol) in 1 mL of anhydrous CH$_2$Cl$_2$. After stiffing for 0.5 h at 0° C. and for 4 h at ambient temperature, the reaction medium is quenched by the addition of a 1N aqueous solution of HCl. After extraction with CH$_2$Cl$_2$, the organic phases are combined, dried over MgSO$_4$, filtered and concentrated under vacuum. Purification is carried out on silica gel (cyclohexane/AcOEt 7:3) in order to produce the expected ester (13.7 mg, 0.02 mmol, 72%) in the form of a colourless oil.

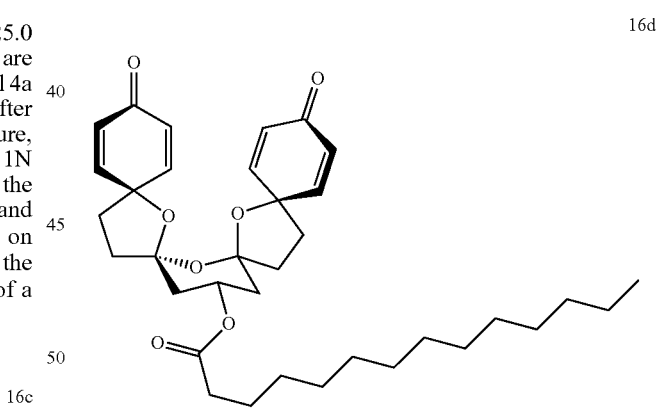

$C_{35}H_{48}O_7$
M=580.8 g.mol$^{-1}$
NMR $^1$H (400 MHz, CDCl$_3$): δ=0.88 (t, J=6.8 Hz, 3H); 1.22-1.35 (m, 20H); 1.55-1.65 (m, 2H); 1.87 (dd, J=13.5, 8.2 Hz, 2H); 2.03-2.18 (m, 4H); 2.26-2.36 (m, 6H); 2.49 (dd, J=13.5, 5.2 Hz, 2H); 5.33-5.40 (m, 1H); 6.09-6.16 (m, 4H); 6.75 (dd, J=10.0, 2.8 Hz, 2H); 7.03 (dd, J=10.0, 2.8 Hz, 2H).
NMR $^{13}$C (100 MHz, CDCl$_3$): δ=14.3; 22.9; 25.1; 29.0-29.9; 32.1; 34.7; 35.4; 39.6; 40.2; 65.4; 79.6; 109.3; 127.6; 127.7; 149.2; 150.7; 173.1; 185.5.
Mass (ESI+): m/z (%) 619 [M+K]$^+$ (14), 603 [M+Na]$^+$ (100).
HRMS (ESI+): m/z calculated for $C_{35}H_{48}O_7$Na 603.3298, found 603.3299.

Example 32

Preparation of (8R,10S,21S)- and (8S,10R,21R)-3-Oxohexadecanoate of 7,9,11-trioxatetraspiro[5.1.1.1.5$^{12}$.2$^{10}$.3$^8$.2$^6$]tetracosa-1,4,13,16-dien-3,15-on-21-yl (16e)

1) Preparation of Intermediate Compound 17

5-(1-Hydroxytridecylidene)-2,2-dimethyl-[1,3]dioxane-4,6-dione (17)

14.3 mL of pyridine is added at 0° C., to a solution of Meldrum's acid (10.60 g, 73.5 mmol) in 70 mL of anhydrous CH$_2$Cl$_2$. After stirring for 15 min at this temperature, commercial tetradecanoyl chloride (18.16 g, 73.5 mmol) is added dropwise, so that the temperature remains below 10° C. After stirring for 2 h at 0° C. and for 1 h at ambient temperature, the reaction medium is washed with 50 mL of a 2N solution of HCl then 2×50 mL of water. After a last washing with a saturated aqueous solution of NaCl, the organic phase is dried over MgSO$_4$, filtered and concentrated under vacuum. The oil obtained is crystallized by the addition of absolute ethanol then left overnight in the refrigerator. The solid is then filtered then rinsed with cold absolute ethanol before being dried in order to produce compound 17 (21.25 g, 59.9 mmol, 81%) in the form of a white solid.

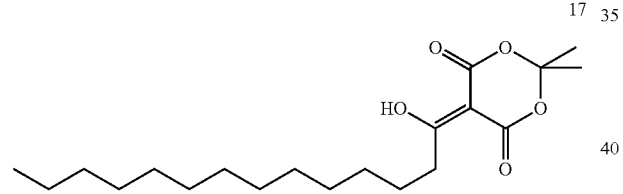

17

C$_{20}$H$_{34}$O$_5$
M=354.5 g.mol$^{-1}$

NMR $^1$H (400 MHz, CDCl$_3$): δ=0.88 (t, J=7.2 Hz, 3H, 3×H14'); 1.24-1.43 (m, 20H, 2×H4', 2×H5', 2×H6', 2×H7', 2×H8', 2×H9', 2×H10', 2×H11', 2×H12', 2×H13'); 1.65-1.72 (m, 2H, 2×H3'); 1.74 (s, 6H, 2×CH$_3$); 3.07 (t, J=7.6 Hz, 2H, 2×H2').

NMR $^{13}$C (100 MHz, CDCl$_3$): δ=14.1 (C14'); 22.7 (C13'); 26.1 (C3'); 26.8 (2×-CH$_3$); 29.2-29.6 (C4', C5', C6', C7', C8', C9', C10', C11'); 31.9 (C12'); 35.7 (C2'); 91.2 (C5); 104.7 (C2); 160.2; 170.6 (C4 and C6); 198.3 (C1').

Mass (FAB+, NBA): m/z (%) 355 [M+H]$^+$ (5), 297 (100).

2) Preparation of Compound 16e

A solution of the alcohol 4a (50 mg, 0.14 mmol) and derivative 17 (48 mg, 0.14 mmol) in 2 mL of anhydrous THF is taken to reflux for 6 h. The reaction medium is concentrated under vacuum. Purification is carried out on silica gel (cyclohexane/AcOEt 8:2) in order to produce the expected ester 16e (30.4 mg, 0.05 mmol, 36%) in the form of a colourless oil.

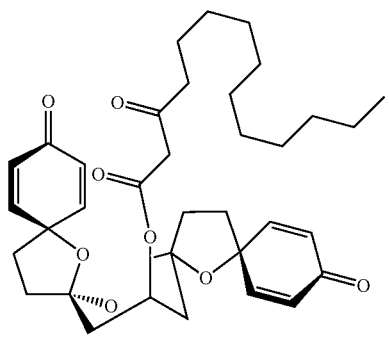

16e

C$_{37}$H$_{50}$O$_8$
M=622.8 g.mol$^{-1}$

NMR $^1$H (400 MHz, CDCl$_3$): δ=0.88 (t, J=6.8 Hz, 3H); 1.22-1.32 (m, 20H); 1.53-1.62 (m, 2H); 1.97-2.27 (m, 10H); 2.45-2.54 (m, 3H); 2.75-2.82 (m, 1H); 3.44 (s, 2H); 5.25-5.34 (m, 1H); 6.11-6.21 (m, 4H); 6.72-6.78 (m, 2H); 6.84 (dd, J=9.6, 3.0 Hz, 1H); 6.92 (dd, J=10.0, 3.0 Hz, 1H).

NMR $^{13}$C (100 MHz, CDCl$_3$): δ=14.3; 22.9; 23.7; 29.2-29.8; 32.1; 35.4; 38.4; 39.6; 39.9; 43.5; 49.4; 67.3; 78.9; 79.7; 109.1; 109.9; 127.6; 127.8; 127.9; 128.2; 148.7; 148.8; 149.8; 150.9; 166.8; 185.2; 185.4; 202.9.

Example 33

Preparation of (8R,10S,21S)- and (8S,10R,21R)-1-(7,9,11-trioxatetraspiro[5.1.1.1.5$^{12}$.2$^{10}$.3$^8$.2$^6$]tetracosa-1,4,13,16-tetraen-3,5-dion-21-yl)-pentadecan-2-one 23c and (8R,10R,21R)-1-(7,9,11-trioxatetraspiro[5.1.1.1.5$^{12}$.2$^{10}$.3$^8$.2$^6$]tetracosa-1,4,13,16-tetraen-3,5-dion-21-yl)-pentadecan-2-one (meso-23d)

1) Preparation of Compound

3-[4-(Tetrahydro-pyran-2-yloxy)-phenyl]-propionic acid ethyl ester (18)

3,4-dihydro-2H-pyran (1.95 g; 23.2 mmol) and the catalyst PPTS (774 mg; 3.02 mmol) are added to a solution of the ester 4'-1 (3.0 g; 15.5 mmol) in CH$_2$Cl$_2$ (25 mL). The reaction is left under stirring while monitoring it on a TLC plate with an (AcOEt/cyclohexane 1:9) eluent system. After stirring for 3 h at ambient temperature, washing with NaCl and extraction with AcOEt is carried out. The organic phase is dried over MgSO$_4$, filtered and concentrated under vacuum. After column chromatography (AcOEt/cyclohexane 1.5:8.5), the protected ester 18 (3.99 g; 14.4 mmol; 93%) is isolated in the form of a yellow oil.

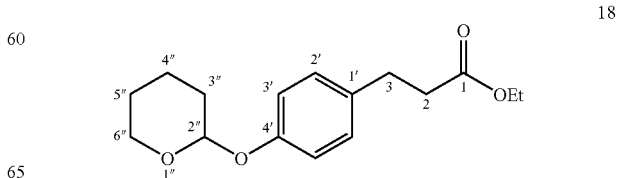

18

$C_{16}H_{22}O_4$
M=278 g.mol$^{-1}$
$R_f$=0.29 (1:9 ethyl acetate/cyclohexane)
UV: 280, 273, 222, 202 nm.
IR $\nu_{max}$ (film, cm$^{-1}$): 2943, 1735, 1510, 1235, 1202, 1038, 969, 921.
$^1$H NMR (400 MHz, CDCl$_3$): δ=1.23 (t, J=7.1 Hz, 3H, —OCH$_2$CH$_3$), 1.55-1.69 (m, 3H, H5a", H4a", H4b"), 1.81-1.88 (m, 2H, H5b", H3a"), 1.99 (m, 1H, H3b"), 2.57 (t, J=7.9 Hz, 2H, 2×H3), 2.88 (t, J=7.9 Hz, 2H, 2×H2), 3.60 (m, 1H, H6a"), 3.90 (m, 1H, H6b"), 4.12 (q, J=7.1 Hz, 2H, —OCH$_2$CH$_3$), 5.37 (brs, 1H, H2"), 6.97 (d, J=8.5 Hz, 2H, 2×H2'), 7.10 (d, J=8.5 Hz, 2H, 2×H3').
$^{13}$C NMR (100 MHz, CDCl$_3$): δ=14.3 (—OCH$_2$CH$_3$), 19.0 (C5"), 25.4 (C4"), 30.3 (C3"), 30.5 (C3), 36.3 (C2), 60.5 (—OCH$_2$CH$_3$), 62.2 (C6"), 96.6 (C2"), 116.6 (2×C2'), 129.3 (2×C3'), 133.8 (C1'), 155.7 (C4'), 173.1 (C1).
LRMS (ESI+): m/z (%) 301 (100) [M+Na]$^+$, 195 (43).

2) Preparation of Compound

{2-Oxo-4-[4-hydroxy-phenylyran-2-yloxy]-butyl}-phosphonic acid diethyl ester (19)

2.5 M n-BuLi in hexane (15 mL, 36.5 mmol) is added at −78° C. to a solution of diethylmethylphosphonate (4.79 g; 37.8 mmol) in anhydrous THF (20 mL). During this addition a white cloudiness is observes. After stirring for 45 min, a solution of the ester 18 (3.5 g; 12.6 mmol) prepared in THF (15 mL) is added. After stirring for 2 h the reaction is neutralized by the addition of 30 mL of NH$_4$Cl, followed by extraction with AcOEt (3×50 mL). The organic phase recovered is then dried over MgSO$_4$, filtered and concentrated under vacuum. Purification is carried out on silica gel (AcOEt/cyclohexane 1:1) in order to produce the ester 19 (3.33 g; 8.67 mmol; 69%) in the form of a yellow oil.

$C_{19}H_{29}O_6P$
M=384 g.mol$^{-1}$
$R_f$=0.16 (1:1 ethyl acetate/cyclohexane)
UV: 280, 274, 222, 202 nm.
IR $\nu_{max}$ (film, cm$^{-1}$): 2942, 2872, 1715, 1510, 1392, 1236, 1023, 968.
$^1$H NMR (400 MHz, CDCl$_3$): δ=1.32 (t, J=7.1 Hz, 6H, 2×-OCH$_2$CH$_3$), 1.56-1.72 (m, 3H, H5a", H4a", H4b"), 1.83-1.88 (m, 2H, H3a", H5b"), 2.00 (m, 1H, H3b"), 2.85 (m, 2H, 2×H3), 2.93 (m, 2H, 2×H4), 3.06 (d, J=22.8 Hz, 2H, 2×H1), 3.59 (m, 1H, H6a"), 3.91 (m, 1H, H6b"), 4.12 (q, J=7.1, 4H, 2×-OCH$_2$CH$_3$), 5.37 (brs, 1H, H2"), 6.96 (d, J=8.6 Hz, 2H, 2×H2'), 7.09 (d, J=8.6 Hz, 2H, 2×H3').
$^{13}$C NMR (100 MHz, CDCl$_3$): δ=16.1 (2×-OCH$_2$CH$_3$), 18.6 (C5"), 25.0 (C4"), 28.4 (C4), 30.1 (C3"), 42.2 (d, J=126 Hz, C1), 45.4 (C3), 61.7 (2×-OCH$_2$CH$_3$), 62.2 (C6"), 96.2 (C2"), 116.3 (2×C2'), 129.0 (2×C3'), 133.4 (C1'), 155.2 (C4'), 200.9 (d, J=6 Hz, C2).
LRMS (ESI+): m/z (%) 407 (100) [M+Na]$^+$, 301 (72).

3) Preparation of Compound (2-{2-[4-(Tetrahydro-pyran-2-yloxy)-phenyl]-ethyl]-[1,3]dithian-2-yl)-acetaldehyde (20)

3,4-dihydro-2H-pyran (1.17 mL; 12.8 mmol) and PPTS (318 mg; 1.28 mmol) is added to a solution of the aldehyde 1 (1.80 g; 6.38 mmol) in anhydrous CH$_2$Cl$_2$ (40 mL). The reaction is left to complete at ambient temperature, while monitoring its progress on a TLC plate with an (AcOEt/cyclohexane 2:8) eluent system. After stirring for 90 min, washing with 30 mL of NaHCO$_3$ and extraction with AcOEt is carried out. The organic phase is dried over MgSO$_4$, filtered and concentrated under vacuum. After column chromatography (AcOEt/cyclohexane 8:92), the protected aldehyde 20 (1.98 g; 5.41 mmol; 85%) is isolated in the form of a yellow oil.

$C_{19}H_{26}O_3S_2$
M=366 g mol$^{-1}$
$R_f$=0.24 (1:9 ethyl acetate/cyclohexane)
UV: 280, 222, 218, 201 nm.
IR $\nu_{max}$ (film, cm$^{-1}$): 2943, 2851, 1718, 1510, 1440, 1234, 1110, 1037, 968, 921.
$^1$H NMR (400 MHz, CDCl$_3$): δ=1.56-1.72 (m, 3H, H4a"", H5a"", H4b""), 1.82-1.88 (m, 2H, H3a"", H3b""), 1.94-2.08 (m, 3H, —SCH$_2$CHH—, —SCH$_2$CHH—, H5b""), 2.24-2.31 (m, 2H, 2×H1"), 2.74-2.81 (m, 2H, 2×H2"), 2.86-2.95 (m, 46H, 2×-SCHH—, 2×-SCHH—, 2×H6""), 3.59 (m, 1H, H6a""), 3.91 (m, 1H, H6b""), 5.39 (brs, 1H, H2""), 6.98 (d, J=8.5 Hz, 2H, 2×H3'), 7.10 (d, J=8.5 Hz, 2H, 2×H2'"), 9.82 (t, J=2.8 Hz, 1H, H1).
$^{13}$C NMR (100 MHz, CDCl$_3$): δ=19.0 (C5""), 24.8 (—SCH$_2$CH$_2$—), 25.4 (C4""), 26.4 (2×-SCH$_2$—), 30.1 (C2"), 30.6 (C3""), 42.6 (C1'), 49.3 (C2'), 50.6 (C2), 62.2 (C6""), 96.7 (C2""), 116.8 (2×C2""), 129.5 (2×C3'"), 134.2 (C1'"), 155.7 (C4'"), 199.8 (C1).
LRMS (ESI+): m/z (%) 389 (100) [M+Na]$^+$, 107 (28).

4) Preparation of Compound

1-[4-(Tetrahydro-pyran-2-yloxy)-phenyl]-6-(2-{2-[4-(tetrahydro-pyran-2-yloxy)-phenyl]-ethyl}-[1,3]dithian-2-yl)-hex-4-in-3-one (21)

Wittig-Horner reagent 19 (964 mg; 2.51 mmol) in anhydrous CH$_3$CN (10 mL) is introduced into a 50 mL flask. Then, LiCl (106 mg; 2.51 mmol) and diisopropyl amine (3.24 g; 25.1 mmol) are added. After stirring for 30 min at ambient temperature, the aldehyde 20 (600 mg; 1.64 mmol), in anhydrous CH$_3$CN (10 mL), is injected. The reaction is left under stirring overnight. Then the solvent is evaporated off and the residue is diluted in 30 mL of AcOEt, which is then washed with a saturated solution of NH$_4$Cl and extracted with AcOEt. The solution is dried over MgSO$_4$ and concentrated under vacuum, then purified on a chromatographic column (AcOEt/cyclohexane 1:9) in order to produce the enone 21 (795 mg; 1.33 mmol; 81%).

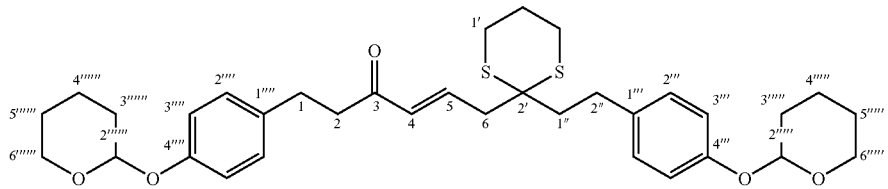

21

$C_{34}H_{44}O_5S_2$

M=596 g.mol$^{-1}$ $R_f$=0.23 (15:85 ethyl acetate/cyclohexane)

UV: 274, 222, 200 nm.

IR $\nu_{max}$ (film, cm$^{-1}$): 2942, 1671, 1627, 1509, 1234, 1202, 1110, 1037, 1022, 968, 921, 830.

$^1$H NMR (400 MHz, CDCl$_3$): δ=1.56-1.68 (m, 6H, H5a''''', H5a'''''', 2×H4''''', 2×H4''''''), 1.81-1.91 (m, 4H, H3a''''', H3b''''', H5b''''', H5b''''''), 1.93-2.02 (m, 4H, —SCH$_2$CH$_2$, H3b''''', H3b''''''), 2.08 (m, 4H, 2×H1'', 2×H1), 2.72 (m, 2H, 2×H2''), 2.69-2.92 (m, 8H, 2×-SCH$_2$CH$_2$, 2×H6, 2×H2), 3.57 (m, 2H, H6a''''', H6a''''''), 3.89 (m, 2H, H6b''''', H6b''''''), 5.36 (m, 2H, H2''''', H2''''''), 6.16 (d, J=16.0 Hz, 1H, H4), 6.88 (td, J=16.0, 7.2 Hz, 1H, H5), 6.94-7.17 (m, 8H, 2×H2''', 2×H2'''', 2×H3''', 2×H3'''').

$^{13}$C NMR (100 MHz, CDCl$_3$): δ=18.9 (C5''''', C5''''''), 25.0 (—SCH$_2$CH$_2$), 25.3 (C4''''', C4''''''), 26.2 (2×-SCH$_2$CH$_2$), 29.4 (C2''), 29.9 (C2), 30.5 (C3''''', C3''''''), 41.5 (C1''), 41.6 (C1), 41.9 (C6), 52.1 (C2'), 62.1 (C6'', C6''''''), 96.5 (C2''''', C2''''''), 116.6 (2×C2''', 2×C2''''), 129.3 (2×C3''', 2×C3''''), 133.1 (C4), 134.3 (C1''', C1''''), 141.8 (C5), 155.5 (C4''', C4''''), 199.3 (C3).

LRMS (ESI+): m/z (%) 619 (100) [M+Na]$^+$, 413 (57), 282 (52).

5) Preparation of Compound 5-((2-(4-(tetrahydro-2H-pyran-2-yloxy)phenethyl)-1,3-dithian-2-yl)methyl)-1-(4-(tetrahydro-2H-pyran-2-yloxy)phenyl)icosane-3,7-dione 22

Trimethyl-(1-methylene-tetradecyloxy)-silane (176 mg, 0.6 mmol) and the enone 21 (176 mg, 0.3 mmol) are dissolved in 2 mL of anhydrous THF and the solution is cooled down to −78° C. Two drops of tetrabutylammonium fluoride (1 M in THF) are injected. The mixture is stirred for 1 h at this temperature, then the solution is left to return to ambient temperature under stirring. After the addition of water and extraction with ethyl acetate, the product is dried and the solvent is evaporated off. The residue is purified by flash chromatography in order to produce compound 22.

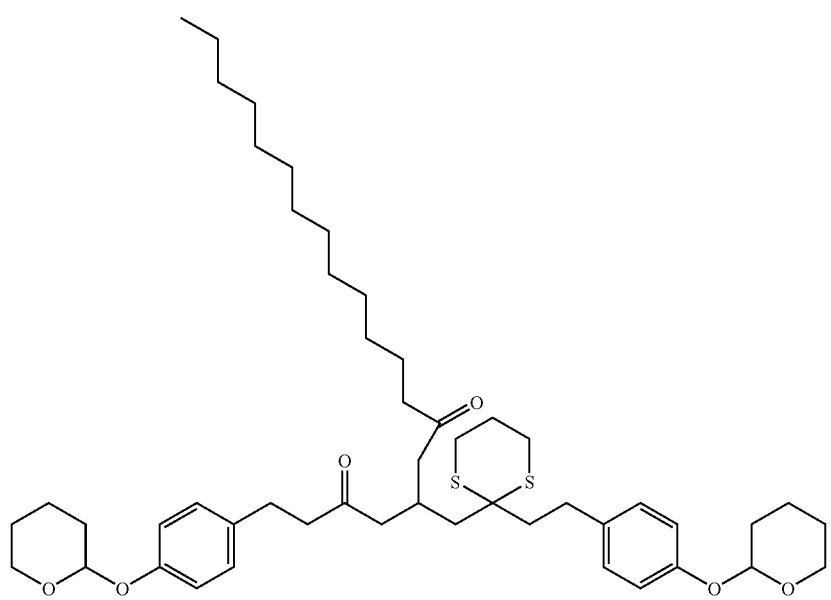

22

6) Preparation of the Compounds (±)-(8S,10R,21R)-1-(7,9,11-trioxatetraspiro
[5.1.1.1.5$^{12}$.2$^{10}$.3$^{8}$.2$^{6}$]tetracosa-1,4,13,16-tetraen-3,
5-dion-21-yl)-pentadecan-2-one 23c and (8R,10R,
21R)-1-(7,9,11-trioxatetraspiro[5.1.1.1.5$^{12}$.2$^{10}$.3$^{8}$.2$^{6}$]
tetracosa-1,4,13,16-tetraen-3,5-dion-21-yl)-
pentadecan-2-one (meso-23d)

Compound 22 in an acetone/H$_2$O mixture (10:1, 0.04 M) is added in the dark and at ambient temperature to PIFA (6.2 equiv). After stirring overnight, the reaction medium is treated with a saturated solution of NaHCO$_3$, before being extracted with AcOEt. After drying (MgSO$_4$), the solvent is evaporated off. Two products 23c and 23d are isolated by flash chromatography.

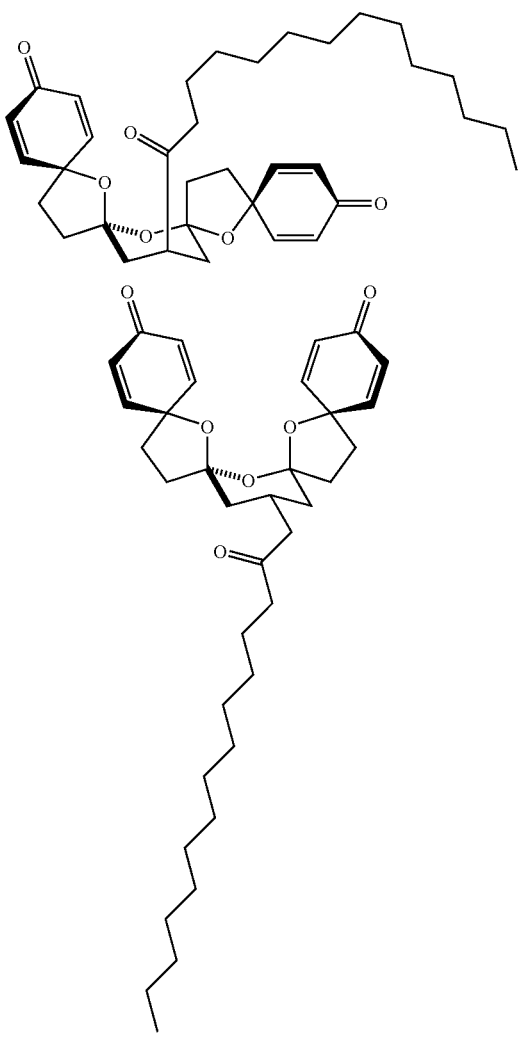

II) Activity of the Compounds

II-1) Antitoxoplasmic Activity In Vitro

The test implemented here is a colorimetric microtitre test. A monolayer of HFF (Human Foreskin Fibroblast) cells is infected, in a synchronous manner, by the parasite (10$^4$ parasites per well, RH-β1 strain). After washing, increasing doses (from 50 nM to 100 μM) of compound are added, except to the control well (addition, or no addition, of DMSO). After incubation for 48 hours, the β-galactosidase activity is measured by the addition of a substrate of the enzyme, chlorophenol red β-D-galactopyranoside (CPRG). The plates are again incubated (from 30 min to 16 h at 37° C.) before being read at 570 and 630 nm. The results are shown in Table I below.

II-2) Antimalarial Activity In Vitro

Before experimentation, parasites of the 3D7 strain (chloroquine-sensitive, Delemarre-Van de Waal H. A. and F. C. de Waal, Ned. Tijdschr. Geneeskd 1981, 125, 375-377; ATCC no.: MRA-102) of *Plasmodium falciparum* are maintained in culture according to the Trager and Jansen method (Trager and Jansen, 1976).

The antimalarial activity is measured in vitro on an asynchronous culture of erythrocytes infected with *Plasmodium falciparum* according to a modified method (Ancelin et al., 2003) based on the Desjardins isotopic microtest (Desjardins et al., 1979). The suspensions of infected erythrocytes (1.5% final haematocrit, 0.6% parasitaemia) were cultured in complete medium (RPMI 1640 supplemented with 0.5% Albumax I) either in the absence of the compound to be tested (control) or in contact with variable concentrations (from $1.5.10^{-5}$ to $4.6.10^{-9}$ M) established by serial dilutions in complete medium from a highly concentrated solution (10 mM in DMSO) of the compound to be tested. After incubation for 48 hours, 0.5 μCi [$^3$H]-hypoxanthine (a precursor necessary for the synthesis of the radiolabelled nucleic acids of the parasite) are added to each microtitre plate well. After incubation for 18 hours, the hypoxanthine incorporation reaction is stopped and the cells lysed by direct freezing at −80° C. After thawing, the parasitic macromolecules, including the radiolabelled nucleic acids, are collected on a filter by means of a cell collector. A scintillation cocktail is added to the filter and the incorporated radioactivity is then measured with a scintillation counter.

The radioactive background noise is measured starting from non-infected erythrocytes and subtracted from each filter measurement. The viability of the parasites treated with the compound to be tested is measured by their ability to synthesize nucleic acids from a radiolabelled precursor ([H$^3$]-hypoxanthine) in comparison with the control parasites cultured in the absence of the compound and is expressed as a percentage of the control. The measurements are analyzed by means of the Graphpad Prism software and the IC$_{50}$ (concentration of compound able to inhibit 50% of the parasites' growth in vitro) is determined graphically. The results obtained appear in the form of IC$_{50}$ in the table and are the result of two experiments carried out independently (different parasite cultures, different dilutions) in duplicate.

The results are shown in Table I below:

TABLE I

| Name or number of the products | Toxoplasma Proliferation test (IC 50) | Plasmodium Proliferation test 3D7 strain (IC 50) |
|---|---|---|
| Chloroquine | not tested | 8-9 nM |
| Natural aculeatin A | 0.309 μM | 0.288 μM |
| Natural aculeatin B | 0.365 μM | 0.454 μM |
| 6-epi-aculeatin D | 0.377 μM | 0.451 μM |
| 10a | 0.500 μM | 1.842 μM |
| 10b | 0.341 μM | 0.654 μM |
| 11b | 1.636 μM | 1.364 μM |
| 10c | 2.4 μM | 0.770 μM |
| 12c | 3.54 μM | 1.031 μM |
| 13c | 3.525 μM | 1.133 μM |

TABLE I-continued

| Name or number of the products | Toxoplasma Proliferation test (IC 50) | Plasmodium Proliferation test 3D7 strain (IC 50) |
| --- | --- | --- |
| 12d | 4.45 µM | 1.151 µM |
| 4b | 1.5 µM | 0.584 µM |
| 4a | 0.173 µM | 0.414 µM |
| 16c | 0.346 µM | 0.0815 µM |
| 16d | 0.636 µM | 0.0917 µM |
| 10e | not tested | 0.899 µM |
| 16a | not tested | 0.343 µM |
| 16b | not tested | 0.331 µM |
| 16e | not tested | 0.122 µM |

The compounds of the invention have a strong activity on both the genus *Plasmodium* and the genus *Toxoplasma*.

II-3) Biological Cycles of *Plasmodium* spp

FIG. 10 shows the different biological cycles of *Plasmodium* Spp. (Robert V & Boudin C. Bull Soc Path Exo 2003; 96: 6-20)

Parasitic Life Cycle in Humans:

The term "exoerythrocytic phase" designates the sporozoite and the hepatic stage. These stages do not seem to have any pathological effect on humans.

The parasitic life cycle in humans begins when an infectious female anopheline mosquito gorges itself on the blood of an individual. The sporozoites, mobile parasitic forms approximately 10 µm long and 1 µm wide which are concentrated in the salivary glands, are transmitted at the site of the bite when the mosquito injects its saliva before and during the blood meal.

Once injected into the human, the sporozoites reach the liver, where they penetrate the hepatocytes. The sporozoite is rapidly converted into a trophozoite, surrounded by a plasma membrane (the plasmalemma) inside a parasitophorous vacuole. A period of intense replication then begins: hepatic schizogony. During this period of the order of 5 to 6 days in the case of *P. falciparum* and 15 days in the case of *P. malariae*, several thousand hepatic merozoites will be formed. The distended, swollen hepatic cell will burst, thus discharging merozoites into the bloodstream. These merozoites cannot however invade the hepatocytes. In infections with *P. vivax* or *P. ovale* certain intrahepatocytic forms do not divide immediately but remain inactive for months before this multiplication begins. These dormant forms or hypnozoites are probably responsible for the relapses which characterize infection by these two parasites.

Blood Stage:

The erythrocytic cycle alone is responsible for the disease.

After their release into the bloodstream, the hepatic merozoites will rapidly invade the erythrocytes and initiate the blood stage. Once it has entered, the merozoite will be transformed into a ring, characterized by very fine cytoplasm surrounding the parasitophorous vacuole. Then the cytoplasm thickens and the parasite increases in size. At this so-called trophozoite stage, grains of pigment appear in the cytoplasm, as a result of the degradation of the haemoglobin to haemozoin. This trophozoite initiates a series of mitoses until a mature schizont (rosette) is formed which bursts, breaking the membrane of the erythrocyte in order to release, depending on the species, from 8 to 32 merozoites. The latter can then invade other erythrocytes. This erythrocytic cycle is 48 hours in the case of *P. falciparum*, *P. vivax* and *P. ovale* and 72 hours in the case of *P. malariae*. A few parasites will have a different development (gametocytogenesis) resulting in gametocytes, sexual forms of the parasite in humans.

II-4) Determination of the Minimum Contact Time Necessary for Cytotoxicity as a Function of the Parasitic State (Time-Course).

A culture of *Plasmodium falciparum* parasites is synchronized with VarioMACS (which retains the mature forms, which synthesize a pigment: haemozoin). After the culture has been passed through a VarioMACS column for 6 h, the synchronization range of the parasites is restricted by a second synchronization with 5% sorbitol (which retains only the young, so-called ring stage) at time $t_0$, i.e. a short time after the invasion of healthy erythrocytes by the merozoites originating from the schizonts obtained by synchronization with the VarioMACS. The parasites are then brought into contact during each stage (ring, then trophozoite then schizont) with a fixed concentration of compound (20×$IC_{50}$ previously defined by the above protocol) and for variable periods of time (30 min, 1 h 30 min, 3 h, 5 h, 7 h and 9 h in the case of parasites treated in the ring stage; 30 min, 1 h 30 min, 3 h, 5 h and 7 h in the case of parasites treated in the trophozoite and schizont stage). At the end of the defined period of contact, the erythrocyte mat is washed twice in complete medium. At $t_{0+44h}$, (i.e. at the start of the subsequent parasitic life cycle), the erythrocyte mats are resuspended and redistributed into 96-well plates (in sextuplicate), 0.5 µCi of tritiated [$^3$H]-hypoxanthine is then added to the culture medium. From then on, the treatment is the same as that of the abovementioned experiment with one difference: the results obtained appear in the form of a graph which represents the viability of the parasites expressed as a control percentage as a function of the time for which the culture is in contact with the compound to be tested.

FIG. 11 shows the results obtained with the compounds 16c and 16d which show that these molecules are active on the different blood stages (rings, trophozoites and schizonts). The action of these molecules is extremely rapid and is not reversible, thus allowing sustained activity.

The invention claimed is:

1. A method for treating malaria or toxoplasmosis, comprising administering to a subject in need thereof at least one polyspirane compound, or physiologically acceptable salts thereof, of formula (I):

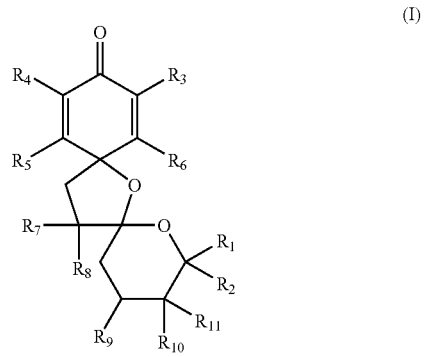

wherein, $R_1$ represents hydrogen and $R_2$ represents a —$CH_2COX$— R' group, in which X=N, O or $CH_2$, when X=O, then R' represents a linear or branched, saturated or unsaturated alkyl of 1 to 20 carbon atoms or a cycloalkyl of 3 to 8 carbon atoms, when X=CH$_2$, then R' represents hydrogen, a linear or branched, saturated or unsaturated alkyl of 1 to 20 carbon atoms or a cycloalkyl of 3 to 8 carbon atoms, and when X=N, then N can be monosubstituted by R' or disubstituted by R' and R" which represent, independently of each other, hydrogen or a linear or branched, saturated or unsaturated alkyl of 1 to 20 carbon atoms or a cycloalkyl of 3 to 8 carbon atoms; and R$_9$ represents:
an OH group,
an O-allyl group, an O-benzyl group, an O—CO-alkyl group, an O—COCH$_2$CO-alkyl group, said alkyl residue being saturated or unsaturated, linear or branched with 1 to 20 carbon atoms, or an O—CO-cycloalkyl group comprising 3 to 8 carbon atoms, or R$_1$ and R$_2$ together represent a G-1 group:

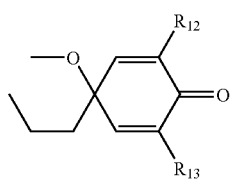

G-1 in which,
R$_{12}$ and R$_{13}$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, or a halogen atom; and R$_9$ represents:
an OH group,
a linear or branched, saturated or unsaturated alkyl group of 1 to 20 carbon atoms, a cycloalkyl group of 3 to 8 carbon atoms,
an S(O)—R" group in which R" is a linear or branched, saturated or unsaturated alkyl of 1 to 20 carbon atoms or a cycloalkyl group of 3 to 8 carbon atoms,
an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group or an O—CH$_2$—CCH group,
an

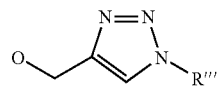

group in which R''' is a linear or branched, saturated or unsaturated alkyl of 1 to 20 carbon atoms, or
an N(R")(R''') group, R" and R''' being as defined above, and whatever R$_1$ and R$_2$ may be:
R$_2$, R$_4$, R$_5$, R$_6$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, or a halogen atom;

R$_7$ and R$_8$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of to 8 carbon atoms, a linear or branched, saturated or unsaturated NH-alkyl group of 1 to 6 carbon atoms, an NH-cycloalkyl group of 3 to 8 carbon atoms, an NHCO—R group, in which R can be a linear or branched, saturated or unsaturated alkyl group of 1 to 6 carbon atoms, or a cycloalkyl group of 3 to 8 carbon atoms; and R$_{10}$ and R$_{11}$ represent independently of each other hydrogen, a hydroxyl group, an O-alkyl group, the alkyl residue being saturated or unsaturated, linear or branched with 1 to 8 carbon atoms, an O-cycloalkyl group of 3 to 8 carbon atoms, or a tertiary amine.

2. The method according to claim 1, wherein the polyspirane compound has general formula (II):

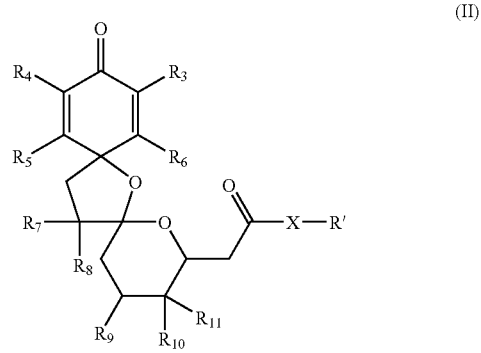

(II)

wherein,
R$_3$ to R$_8$, R$_{10}$ to R$_{11}$, X and R' are as previously defined, and
R$_9$ represents an OH group, an O-allyl group, an O-benzyl group, an O—CO-alkyl group, an O—COCH$_2$—CO-alkyl group, said alkyl residue being saturated or unsaturated, linear or branched with 1 to 20 carbon atoms, or an O—CO-cycloalkyl group comprising 3 to 8 carbon atoms.

3. The method according to claim 1, wherein the polyspirane compound has general formula (III):

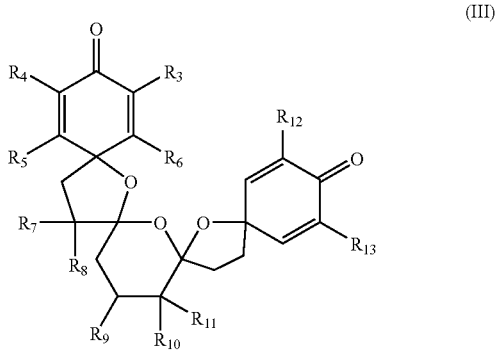

(III)

wherein,
R$_3$ to R$_8$ and R$_{10}$ to R$_{13}$ are as previously defined when R$_1$ and R$_2$ form together the G-1 group, and
R$_9$ represents:
an OH group,
a linear or branched, saturated or unsaturated alkyl group of 1 to 20 carbon atoms, or a cycloalkyl group of 3 to 8 carbon atoms,
an S(O)—R" group in which R" is a linear or branched, saturated or unsaturated alkyl of 1 to 20 carbon atoms or a cycloalkyl group of 3 to 8 carbon atoms,
an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group or an O—CH$_2$—CCH group,
an

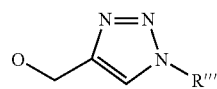

group in which R'" is a linear or branched, saturated or unsaturated alkyl of 1 to 20 carbon atoms, or
an N(R")(R'") group, R" and R'" being as defined above.

4. The method according to claim 1, wherein the subject is infected with *Plasmodium malariae, Plasmodium vivax, Plasmodium ovale* or *Plasmodium falciparum*.

5. The method according to claim 1, wherein the subject is infected with *Toxoplasma gondii*.

6. A polyspirane compound of formula (I):

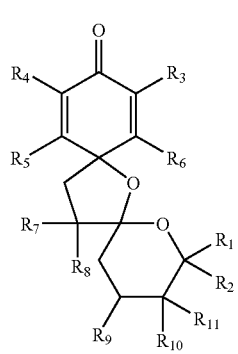

(I)

wherein,
R$_1$ represents hydrogen and R$_2$ represents a —CH$_2$COX—R' group, in which X=N, O or CH$_2$,
when X=O, then R' represents a linear or branched, saturated or unsaturated alkyl of 1 to 20 carbon atoms or a cycloalkyl of 3 to 8 carbon atoms,
when X=CH$_2$, then R' represents hydrogen, a linear or branched, saturated or unsaturated alkyl of 1 to 20 carbon atoms or a cycloalkyl of 3 to 8 carbon atoms, and
when X=N, then N can be monosubstituted by R' or disubstituted by R' and R" which represent, independently of each other, hydrogen or a linear or branched, saturated or unsaturated alkyl of 1 to 20 carbon atoms or a cycloalkyl of 3 to 8 carbon atoms; and R$_9$ represents:
an OH group, or
an O-allyl group, an O-benzyl group, an O—CO-alkyl group, an O—COCH$_2$CO-alkyl group, said alkyl residue being saturated or unsaturated, linear or branched with 1 to 20 carbon atoms, or an OCO-cycloalkyl group of 3 to 8 carbon atoms, or
R$_1$ and R$_2$ together represent a G-1 group:

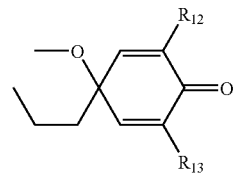

G-1 in which,
R$_{12}$ and R$_{13}$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, or a halogen atom; and
R$_9$ represents:
an OH group,
a linear or branched, saturated or unsaturated alkyl group of 1 to 20 carbon atoms, or a cycloalkyl group of 3 to 8 carbon atoms,
an S(O)—R" group in which R" is a linear or branched, saturated or unsaturated alkyl of 1 to 20 carbon atoms or a cycloalkyl group of 3 to 8 carbon atoms,
an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group or a O—CH$_2$—CCH group,
an

group in which R'" is a linear or branched, saturated or unsaturated alkyl of 1 to 20 carbon atoms, or
an N(R")(R'") group, R" and R'" being as defined above,
and whatever R$_1$ and R$_2$ may be:
R$_3$, R$_4$, R$_5$, R$_6$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of 3 to 8 carbon atoms, or a halogen atom;
R$_7$ and R$_8$ represent independently of each other hydrogen, a linear or branched, saturated or unsaturated alkyl group of 1 to 6 carbon atoms, a cycloalkyl group of 3 to 8 carbon atoms, a linear or branched, saturated or unsaturated, O-alkyl group of 1 to 6 carbon atoms, an O-cycloalkyl group of to 8 carbon atoms, a linear or branched, saturated or unsaturated NH-alkyl group of 1 to 6 carbon atoms, an NH-cycloalkyl group of 3 to 8 carbon atoms, an NHCO—R group, in which R can be a linear or branched, saturated or unsaturated alkyl group of 1 to 6 carbon atoms, or a cycloalkyl group of 3 to 8 carbon atoms; and $R_{10}$ and $R_{11}$ represent independently of each other hydrogen, a hydroxyl group, an O-alkyl group, the alkyl residue being saturated or unsaturated, linear or branched with 1 to 8 carbon atoms, an O-cycloalkyl group of 3 to 8 carbon atoms, or a tertiary amine.

7. The polyspirane compound according to claim 6, of general formula (II):

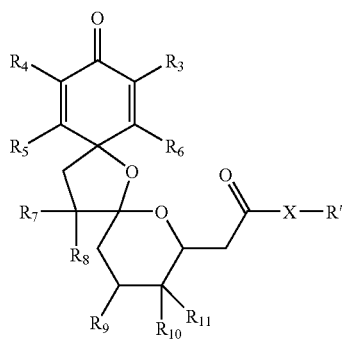

wherein, $R_3$ to $R_8$, $R_{10}$ to $R_{11}$, X and R' are as previously defined and, $R_9$ represents an OH group, an O-allyl group, an O-benzyl group, an O—CO-alkyl group, said alkyl being saturated or unsaturated, linear or branched with 1 to 20 carbon atoms, or an O-CO-cycloalkyl group comprising 3 to 8 carbon atoms.

8. The polyspirane compound according to claim 7, of general formula (III):

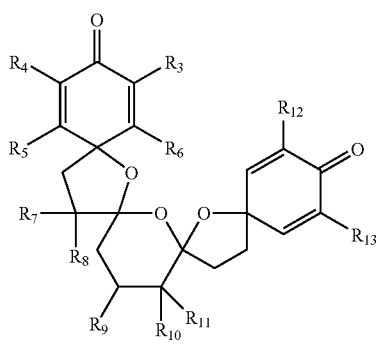

wherein, $R_3$ to $R_8$ and $R_{10}$ to $R_{13}$ are as previously defined when $R_1$ and $R_2$ form together the G-1 group, and $R_9$ represents:

an OH group, a linear or branched, saturated or unsaturated alkyl group of 1 to 20 carbon atoms, a cycloalkyl group of 3 to 8 carbon atoms, an S(O)—R'' group in which R'' is a linear or branched, saturated or unsaturated alkyl of 1 to 20 carbon atoms or a cycloalkyl group of 3 to 8 carbon atoms, an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group; an O—CH$_2$—CCH group, an

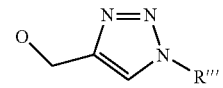

group in which R''' is a linear or branched, saturated or unsaturated alkyl of 1 to 20 carbon atoms, or an N(R'')(R''') group, R'' and R''' being as defined above.

9. The polyspirane compound of general formula (II) according to claim 7, wherein, $R_3$ to $R_8$ and $R_{10}$ to $R_{11}$ represent hydrogen, $R_9$ represents OH, X=O, and R' is a linear, saturated alkyl with 3 carbon atoms, 10 carbon atoms or 18 carbon atoms.

10. The polyspirane compound of general formula (III) according to claim 8, wherein, $R_3$ to $R_8$ and $R_{10}$ to $R_{13}$ represent hydrogen, and $R_9$ is an OH group, or O—CO-alkyl in which the alkyl is linear and has 7 carbon atoms, 14 carbon atoms or 16 carbon atoms.

11. The polyspirane compound of general formula (III) according to claim 10, comprising a mixture of (8R,10S,21S) and (8S, 10R,21R) enantiomers.

12. The polyspirane compound of general formula (III) according to claim 10, comprising at least one of an (8R,10R, 21S) enantiomer, an (8R,10S,21S) enantiomer or an (8S,10R, 21R) enantiomer.

13. A pharmaceutical composition comprising as active ingredient at least one polyspirane compound of general formula I according to claim 6, in combination with a pharmaceutically acceptable excipient.

14. The pharmaceutical composition according to claim 13, presented in a form which can be administered to a subject by oral route at a rate of from 0.1 mg/kg/d to 100 mg/kg/d of active ingredient.

15. A method for preparing the polyspirane compound of formula I as defined in claim 6, comprising:

conducting phenolic oxidation of a compound of formula (I-Z) with an oxidizing agent

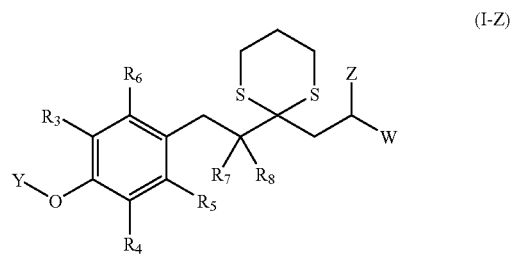

wherein,
either W represents a group of formula (II-W):

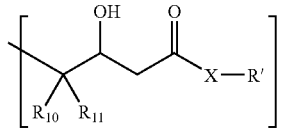

X=O or N,

Y represents hydrogen,

Z represents an OH group, and $R_3$ to $R_8$, $R_{10}$, $R_{11}$, X, R' and R''' are as defined in claim 1, in order to obtain a compound of general formula II in which X=O or N and $R_9$ represents an OH group, and then optionally conducting a stage of acylation or alkylation of said compound of general formula II in which $R_9$ represents an OH group in order to obtain a compound of general formula II in which $R_9$ is an O—CO-alkyl group, an O-allyl group, an O-benzyl group, an O—COCH$_2$CO-alkyl group, said alkyl residue being saturated or unsaturated, linear or branched with 1 to 20 carbon atoms, or an O—CO-cycloalkyl group comprising 3 to 8 carbon atoms;

or W represents a group of formula II'-W:

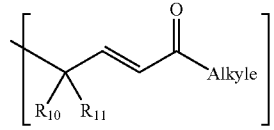

said alkyl being saturated or unsaturated, linear or branched with 1 to 17 carbon atoms or a cycloalkyl of 3 to 8 carbon atoms, and X=CH$_2$;

Y represents a (Pr$_3$)Si— group, and

Z represents a (Pr$_3$)Si—O— group, in order to obtain a compound of general formula II in which X=CH$_2$ and $R_9$ represents an OH group, and then optionally conducting a stage of acylation or alkylation of the obtained compound of general formula II in which $R_9$ represents an OH group in order to obtain a compound of general formula II in which $R_9$ is an O—CO-alkyl group, an O-allyl group, an O-benzyl group, an O—COCH$_2$CO-alkyl group, said alkyl residue being saturated or unsaturated, linear or branched with 1 to 20 carbon atoms, or an O—CO-cycloalkyl group comprising 3 to 8 carbon atoms, or W represents a III-W group:

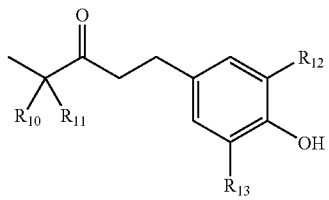

and Z represents:

O-cycloalkyl group of 3 to 8 carbon atoms, an O—CH$_2$—CH$_2$—N(CH$_3$)$_2$ group or an O—CH$_2$—CCH group, or an N(R")(R''') group, R" and R''' being as defined above, and, when Z is an OH group, optionally conducting an acylation or alkylation in order to obtain a compound of general formula III in which $R_9$ is an O-alkyl group, an O-cycloalkyl group, an O—CO-alkyl group, an O—COCH$_2$CO-alkyl group, an O—CH$_2$—CH$_2$—N(CH$_3$)$_2$ group or an O—CH$_2$—CCH group, and/or, when Z represents an —O—CH$_2$—CCH group, optionally conducting an addition reaction with N$_3$—R''' in order to obtain a compound of general formula III in which $R_9$ is an

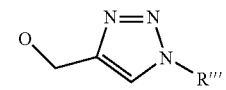

group, R''' being as previously defined.

16. The method according to claim 15, wherein the polyspirane compound is of formula II,

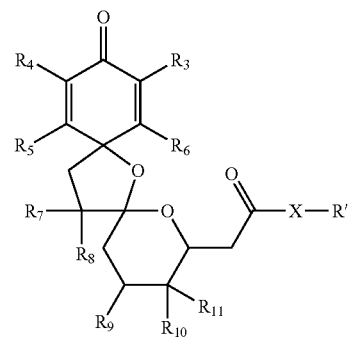

an OH group, a linear or branched, saturated or unsaturated alkyl group of 1 to 20 carbon atoms, a cycloalkyl group of 3 to 8 carbon atoms, a group S—R" in which R" is a linear or branched, saturated or unsaturated alkyl of 1 to 20 carbon atoms or a cycloalkyl group of 3 to 8 carbon atoms, an O-alkyl group, the alkyl being saturated or unsaturated, linear or branched with 1 to 20 carbon atoms, an O-cycloalkyl group of 3 to 8 carbon atoms, an O—CH$_2$—CH$_2$—N(CH$_3$)$_2$ group or an O—CH$_2$—CCH group, or an N(R")(R''') group, R" and R''' being as defined above, and $R_3$ to $R_8$ and $R_{10}$ to $R_{13}$ being as defined in claim 1, in order to obtain a compound of general formula III in which $R_9$ represents:

an OH group,
a linear or branched, saturated or unsaturated alkyl group of 1 to 20 carbon atoms, or a cycloalkyl group of 3 to 8 carbon atoms,
an S(O)—R" group in which R" is a linear or branched, saturated or unsaturated alkyl of 1 to 20 carbon atoms or a cycloalkyl group of 3 to 8 carbon atoms,
an O-alkyl group, the alkyl being saturated or unsaturated, linear or branched with 1 to 20 carbon atoms, an in which,
X=O or N,
$R_3$ to $R_8$, $R_{10}$ to $R_{11}$, X and R' are as previously defined, and
$R_9$ represents an OH group, an O-allyl group, an O-benzyl group, an O—CO-alkyl group, said alkyl being saturated or unsaturated, linear or branched with 1 to 20 carbon atoms, or an O—CO-cycloalkyl group comprising 3 to 8 carbon atoms, the method comprising:
reacting an aldehyde of formula (IV):

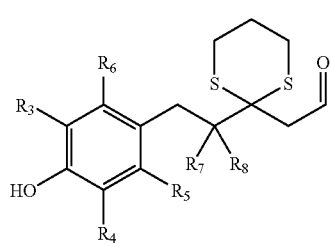

(IV)

$R_3$ to $R_8$ being as previously defined,
with a compound of formula VII:

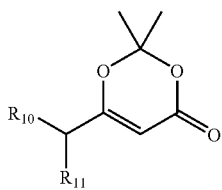

(VII)

in order to obtain the compound of formula (V):

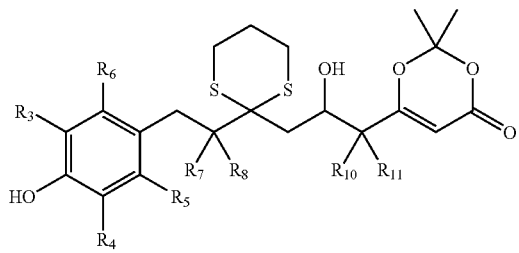

(V)

$R_3$ to $R_8$ and $R_{10}$ to $R_{11}$ being as previously defined;
reacting the obtained compound of formula (V) with a compound R'—X—H, (X=O) or (R')(R")—X—H (X=N), R' and R" being as previously defined, then reducing with a reducing agent, in order to obtain a compound of formula (I-Z) in which W represents the group of formula II-W; and conducting phenolic oxidation of the obtained compound of formula (I-Z) with an oxidizing agent in order to obtain a compound of formula II in which $R_9$ is OH; and optionally,
conducting an acylation or alkylation reaction of the obtained compound of formula II in which $R_9$ is OH, in order to obtain a compound of formula II in which $R_9$ represents an O-allyl group, an O-benzyl group, an O—CO-alkyl group, or an O—CO-cycloalkyl group as previously defined.

17. The method according to claim 15, wherein the polyspirane compound is of formula II:

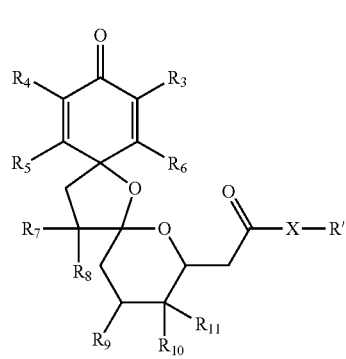

(II)

in which X=CH$_2$,
the method comprising:
reacting an ester of formula (VIII):

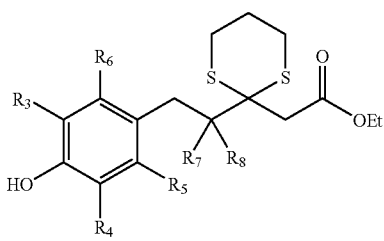

(VIII)

$R_3$ to $R_8$ being as previously defined,
with an acetate of tert-butyl

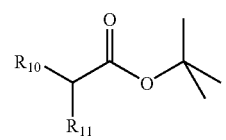

in the presence of a base, in order to obtain the compound of formula (IX):

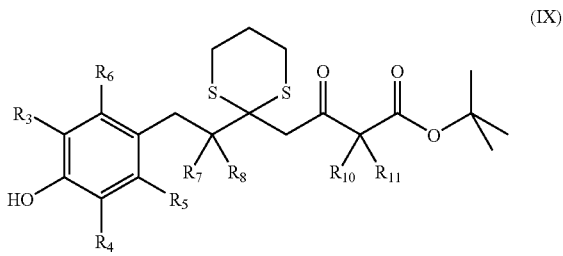

(IX)

$R_3$ to $R_8$ being as previously defined;

reducing the obtained compound of formula (IX) and then reacting the reduced compound with tri-propyl silyl chloride in order to produce the compound of formula (X):

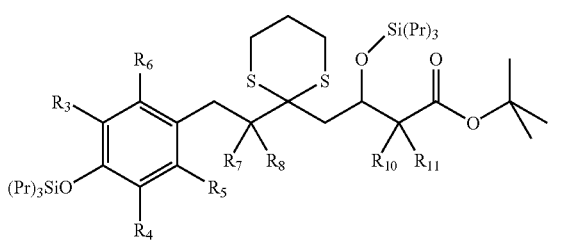

(X)

reducing the produced compound of formula (X) with a reducing agent in order to produce the compound of formula (XI):

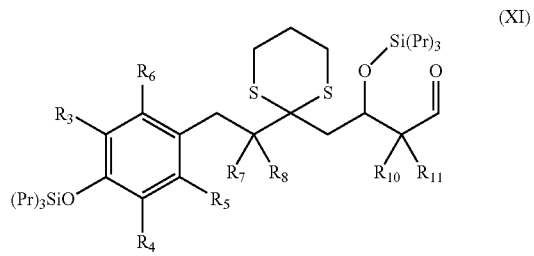

(XI)

conducting a Wittig reaction on the produced compound of formula (XI) in order to obtain a compound of formula (I-Z) in which W represents the group of formula II'-W; and conducting a phenolic oxidation of the obtained compound of formula (I-Z) with an oxidizing agent in order to obtain the compound of formula II in which $R_9$ is OH and $X=CH_2$; and optionally, conducting an acylation or alkylation reaction of the obtained compound of formula II in which $R_9$ is OH and $X=CH_2$, in order to obtain a compound of general formula II in which $X=CH_2$ and $R_9$ represents an O-allyl group, an O-benzyl group, an O—CO-alkyl group, or an O—CO-cycloalkyl group as previously defined.

18. The method according to claim 15, wherein the polyspirane compound is of formula III,

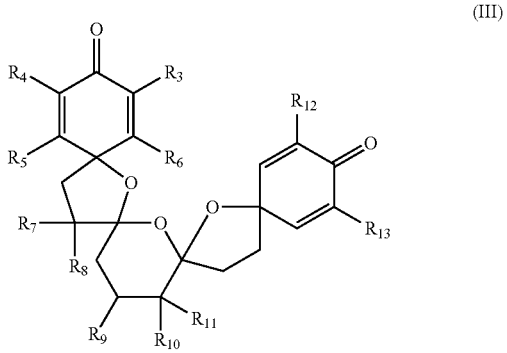

(III)

in which, $R_3$ to $R_8$ and $R_{10}$ to $R_{13}$ are as previously defined when $R_1$ and $R_2$ form together the G-1 group, and $R_9$ represents:
an OH group,
a linear or branched, saturated or unsaturated alkyl group of 1 to 20 carbon atoms, a cycloalkyl group of 3 to 8 carbon atoms,
an S(O)—R'' group in which R'' is a linear or branched, saturated or unsaturated alkyl of 1 to 20 carbon atoms or a cycloalkyl group of 3 to 8 carbon atoms,
an O-alkyl group, an O—CO-alkyl group, an O—COCH$_2$CO-alkyl group, said alkyl residue being saturated or unsaturated, linear or branched with 1 to 20 carbon atoms, an O-cycloalkyl group of 3 to 8 carbon atoms, an O—CH$_2$—CH$_2$—N(CH$_3$)$_2$ group; an O—CH$_2$—CCH group, or
an N(R'')(R''') group, R'' and R''' being as defined above, said compound III-3 being obtained by dehydration of a compound I-Z in which Z=OH of formula (III-1) below:

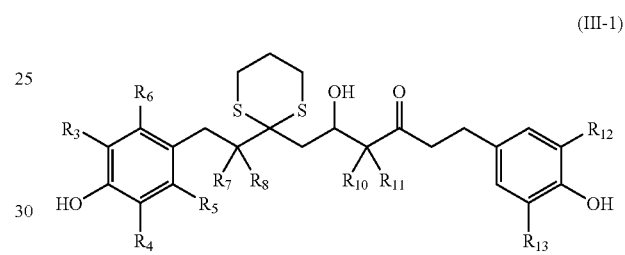

(III-1)

in which $R_{11}$ represents hydrogen and $R_3$ to $R_8$, $R_{10}$ to $R_{13}$, R'' and R''' being as previously defined.

19. The method according to claim 15, wherein the polyspirane compound is of formula III,

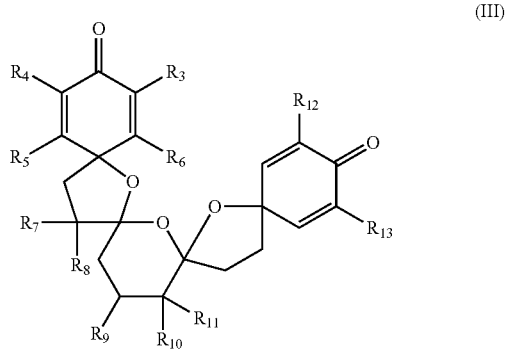

(III)

in which, $R_3$ to $R_8$ and $R_{10}$ to $R_{13}$ are as previously defined when $R_1$ and $R_2$ form together the G-1 group, and an

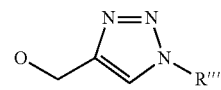

group in which R''' is a linear or branched, saturated or unsaturated alkyl of 1 to 20 carbon atoms, or an N(R'')(R''') group, R'' and R''' as defined above, in which wherein the compound I-Z is obtained by adding a nucleophile by Michael-type addition to a compound of formula III-3:

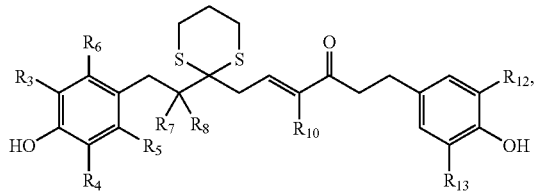

(III-3)

W representing the III-W group and Z representing:
- a linear or branched, saturated or unsaturated alkyl group of 1 to 20 carbon atoms, or a cycloalkyl group of 3 to 8 carbon atoms,
- an S—R" group in which R" is a linear or branched, saturated or unsaturated alkyl of 1 to 20 carbon atoms or a cycloalkyl group of 3 to 8 carbon atoms,
- an O-alkyl group as previously defined, an O-cycloalkyl group of 3 to 8 carbon atoms, or an O—$CH_2$—$CH_2$—$N(CH_3)_2$ group,
- an O—$CH_2$—CCH group, or $R_9$ represents:
- an OH group,
- a linear or branched, saturated or unsaturated alkyl group of 1 to 20 carbon atoms, a cycloalkyl group of 3 to 8 carbon atoms,
- an S(O)—R" group in which R" is a linear or branched, saturated or unsaturated alkyl of 1 to 20 carbon atoms or a cycloalkyl group of 3 to 8 carbon atoms,
- an O-alkyl group, an O—CO-alkyl group, an O—$COCH_2$CO-alkyl group, said alkyl residue being saturated or unsaturated, linear or branched with 1 to 20 carbon atoms, an O-cycloalkyl group of 3 to 8 carbon atoms, an O—$CH_2$—$CH_2$—$N(CH_3)_2$ group; an O—$CH_2$—CCH group, or
- an

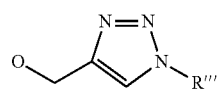

group in which R'" is a linear or branched, saturated or unsaturated alkyl of 1 to 20 carbon atoms, or an N(R")(R'") group, R" and R'" as defined above, wherein the compound I-Z, where Z is an OH group, is obtained by reacting an aldehyde of formula (IV):

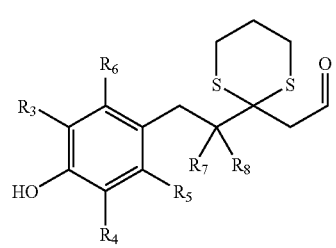

(IV)

$R_3$ to $R_8$ being as previously defined, with a compound of formula (VI):

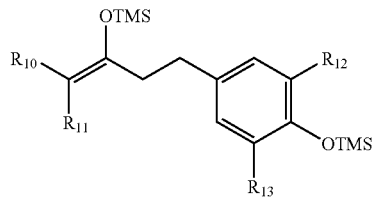

(VI)

$R_{10}$ to $R_{13}$ being as previously defined.

20. The method according to claim 15, wherein the polyspirane compound is of formula III,

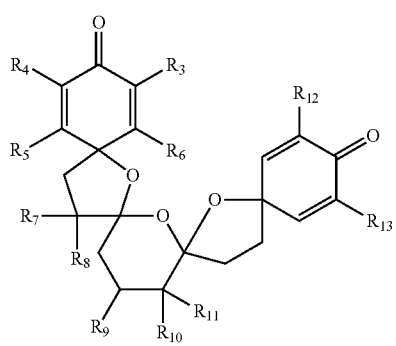

(III)

in which $R_9$ represents an OH group, an O-alkyl group, an O—CO-alkyl group, an O—$COCH_2$CO-alkyl group, said alkyl being saturated or unsaturated, linear or branched with 1 to 20 carbon atoms, or an O—CO-cycloalkyl group of 3 to 8 carbon atoms, the method comprising:

reacting an aldehyde of formula (IV):

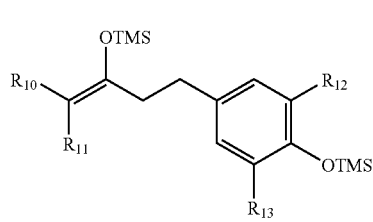

(IV)

$R_3$ to $R_8$ being as previously defined, with a compound of formula (VI):

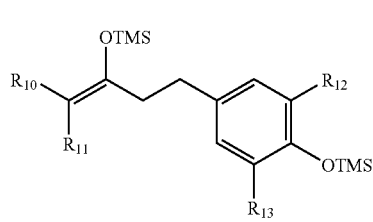

(VI)

$R_{10}$ to $R_{13}$ being as previously defined, in order to obtain a compound I-Z in which Z=OH of formula (III-1):

(III-1)

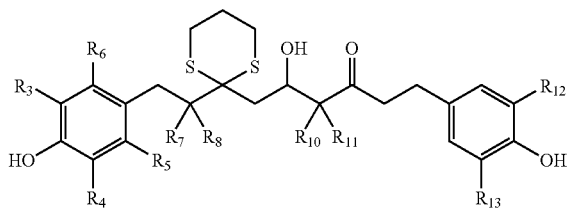

conducting phenolic oxidation with an oxidizing agent such of the obtained compound (III-1), in order to obtain a compound III, in which $R_9$ is OH; and optionally, conducting an acylation or alkylation reaction of obtained compound III in which $R_9$ is an OH group, in order to obtain a desired compound of formula III in which $R_9$ is an O—allyl group, an O-benzyl group, an O—CO-alkyl group, an O—COCH$_2$CO-alkyl group, or an O—CO-cycloalkyl group.

21. The method according to claim 18, for preparing compounds of formula III where $R_9$ is an alkyl group as previously defined, comprising:

conducting an addition of a CuXRa nucleophile by Michael-type addition, Ra representing an alkyl group as previously defined, to the obtained compound of formula III-3, in order to produce the compound I-Z in which Z=Ra of formula (III-4):

(III-4)

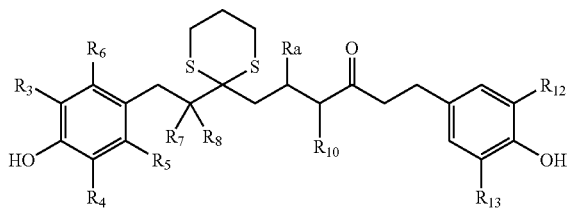

in which $R_3$ to $R_8$, $R_{10}$, $R_{12}$ and $R_{13}$ are as previously defined and Ra represents an alkyl group as previously defined; and conducting phenolic oxidation with an oxidizing agent of the obtained compound (III-4), in order to obtain a compound III in which $R_9$ is an alkyl group as previously defined.

22. The method according to claim 18, for preparing compounds of formula III in which $R_9$ is an N(R")(R''') group, R" and R''' being as defined above, comprising:

conducting an addition of an HN(R")(R''') nucleophile by hetero-Michael type addition to the obtained compound of formula III-3 in order to produce the compound I-Z in which Z=N(R")(R''') of formula (III-5) below:

(III-5)

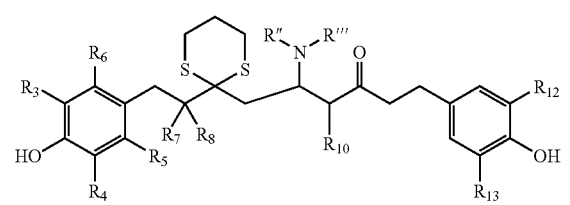

in which $R_3$ to $R_8$, $R_{10}$, $R_{12}$ and $R_{13}$ are as previously defined; and conducting phenolic oxidation with an oxidizing agent such as PIFA and PIDA, in particular PIFA, of the obtained compound (III-5), in order to obtain the compound III in which $R_9$ is an N(R")(R''') group as defined above.

23. The method according to claim 18, for preparing compounds of formula III in which $R_9$ is an S(O)—R" group, R" being as defined above, comprising:

conducting an addition of an R"SH nucleophile by hetero-Michael type addition, R" being as defined above, to the obtained compound III-3 in order to produce the compound I-Z in which Z=SR" of formula (III-6):

(III-6)

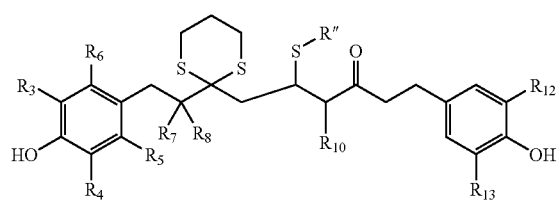

in which $R_3$ to $R_8$, $R_{10}$, $R_{12}$, $R_{13}$ and R" are as previously defined; and conducting a phenolic oxidation with an oxidizing agent such as PIFA and PIDA, in particular PIFA, of the obtained compound (III-6), in order to obtain the compound of formula III in which $R_9$ is an —S(O)R" group, R" being as previously defined.

24. The method according to claim 18, for preparing compounds of formula III in which $R_9$ is an O-alkyl group as previously defined, an O—CH$_2$—CH$_2$—N(CH$_3$)$_2$ group, an O—CH$_2$—CCH group, or an

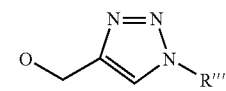

group, R''' being as previously defined, comprising:

conducting an addition of an ROH nucleophile by hetero-Michael type addition, R being an alkyl as previously defined, an —CH$_2$—CH$_2$—N(CH$_3$)$_2$ group or a —CH$_2$—CCH group, to the obtained compound III-3 in order to produce compound I-Z in which Z=OR of formula (III-2):

(III-2)

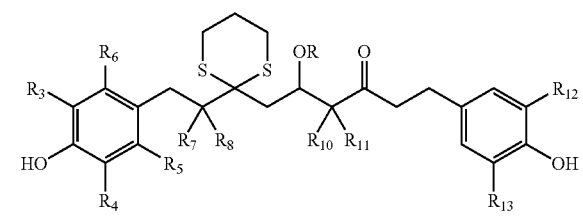

in which $R_3$ to $R_8$ and $R_{10}$, $R_{12}$ and $R_{13}$ are as previously defined and $R_{11}$ represents hydrogen; and conducting a phenolic oxidation with an oxidizing agent such as PIFA and PIDA, in particular PIFA, of the obtained compound (III-2), in order to obtain a compound III in which $R_9$ is an O-alkyl group as previously defined, a group O-$CH_2$—$CH_2$—$N(CH_3)_2$ or a group O—$CH_2$—CCH, and optionally, conducting an addition reaction of the obtained compound III in which $R_9$ is an O—$CH_2$—CCH group, with $N_3$—R''' in order to obtain the compound of formula III in which $R_9$ is a

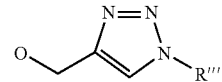

group, R''' being as previously defined.

* * * * *

UNITED STATES PATENT AND TRADEMARK OFFICE
CERTIFICATE OF CORRECTION

PATENT NO. : 8,389,569 B2  Page 1 of 1
APPLICATION NO. : 12/681485
DATED : March 5, 2013
INVENTOR(S) : Wong et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 436 days.

Signed and Sealed this
First Day of September, 2015

Michelle K. Lee
*Director of the United States Patent and Trademark Office*